(12) United States Patent
Kanderian

(10) Patent No.: US 8,412,466 B2
(45) Date of Patent: Apr. 2, 2013

(54) RAPID METHOD OF PATTERN RECOGNITION, MACHINE LEARNING, AND AUTOMATED GENOTYPE CLASSIFICATION THROUGH CORRELATION ANALYSIS OF DYNAMIC SIGNALS

(75) Inventor: Sami Kanderian, Rockville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 135 days.

(21) Appl. No.: 12/759,415

(22) Filed: Apr. 13, 2010

(65) Prior Publication Data

US 2011/0010103 A1    Jan. 13, 2011

Related U.S. Application Data

(60) Provisional application No. 61/168,649, filed on Apr. 13, 2009.

(51) Int. Cl.
*G06F 19/00*      (2011.01)
*G06F 15/00*      (2006.01)
*C12Q 1/68*       (2006.01)

(52) U.S. Cl. ................... 702/20; 435/6.1; 700/1

(58) Field of Classification Search .............. None
See application file for complete search history.

(56) References Cited

U.S. PATENT DOCUMENTS

| | | | |
|---|---|---|---|
| 6,154,707 | A | 11/2000 | Livak et al. |
| 6,884,583 | B2 | 4/2005 | Livak et al. |
| 6,960,437 | B2 | 11/2005 | Enzelberger et al. |
| 2002/0177153 | A1 | 11/2002 | Apffel, Jr. et al. |
| 2002/0197630 | A1 | 12/2002 | Knapp et al. |
| 2004/0053302 | A1 | 3/2004 | Livak et al. |
| 2004/0061616 | A1 | 4/2004 | Fischer et al. |
| 2005/0042639 | A1 | 2/2005 | Knapp et al. |
| 2005/0233335 | A1 | 10/2005 | Wittwer et al. |
| 2006/0019253 | A1 | 1/2006 | Wittwer et al. |
| 2007/0003939 | A1 | 1/2007 | Wang et al. |
| 2007/0020665 | A1 | 1/2007 | Gupta et al. |
| 2007/0020672 | A1 | 1/2007 | Wittwer et al. |
| 2007/0026421 | A1 | 2/2007 | Sundberg et al. |
| 2007/0072211 | A1 | 3/2007 | Newton et al. |
| 2007/0134706 | A1 | 6/2007 | Matsumoto et al. |
| 2007/0177841 | A1 | 8/2007 | Danziger |
| 2007/0231799 | A1 | 10/2007 | Knight et al. |
| 2008/0082273 | A1 | 4/2008 | Glanowski et al. |
| 2008/0163824 | A1 | 7/2008 | Moser et al. |
| 2008/0176230 | A1 | 7/2008 | Owen et al. |

FOREIGN PATENT DOCUMENTS

| | | |
|---|---|---|
| WO | 2004/097577 A2 | 11/2004 |
| WO | 2005/075683 A1 | 8/2005 |
| WO | 2008/025093 A1 | 3/2008 |

OTHER PUBLICATIONS

Teo et al. Single-Step Scalable-Throughput Molecular Screening for Huntington Disease Clinical Chemistry vol. 54, pp. 964-972 (2008).*
Allawi et al., "Thermodynamics of internal C.T mismatches in DNA," Nucleic Acids Res vol. 26, pp. 2694-2701 (1998).
Allawi et al., "Nearest-neighbor thermodynamics of internal A.C mismatches in DNA: sequence dependence and pH effects," Biochemistry, vol. 37, pp. 9435-9444 (1998) (abstract).
Allawi et al., "Thermodynamics and NMR of internal G.T mismatches in DNA," Biochemistry, vol. 36, pp. 10581-10594 (1997) (abstract).
Allawi et al., "Nearest neighbor thermodynamic parameters for internal G.A mismatches in DNA." Biochemistry, vol. 37, pp. 2170-2179 (1998) (abstract).
Anne et al., "Dynamics of Electron Transport by Elastic Bending of Short DNA Duplexes. Experimental Study and Quantitative Modeling of the Cyclic Voltammetric Behavior of 3'-Ferrocenyl DNA End-Grafted on Gold," J. Am. Chem. Soc., vol. 128, pp. 542-547 (2006) (abstract).
Bommarito et al., "Thermodynamic parameters for DNA sequences with dangling ends," Nucleic Acids Res, vol. 28, No. 9, pp. 1929-1934 (2000).
Erdem et al., "Novel hybridization indicator Methylene Blue for the electrochemical detection of short DNA sequences related to the Hepatitis B Virus," Anal. Chim. Acta, vol. 422, pp. 139-149 (2000) (abstract).
Fan et al., "Electrochemical interrogation of conformational changes as a reagentless method for the sequence-specific detection of DNA," Proc. Natl. Acad. Sci. U.S.A., vol. 100, pp. 9134-9137 (2003).
Gooding et al., "Electrochemical DNA Hybridization Biosensors" Electroanalysis, vol. 14, pp. 1149-1156 (2002) (abstract).
Gooding et al., "The ion gating effect: using a change in flexibility to allow label free electrochemical detection of DNA hybridisation," Chem. Commun., vol. 15, pp. 1938-1939 (2003).
Herrmann et al. "Amplicon DNA Melting Analysis for Mutation Scanning and Genotyping: Cross-Platform Comparison of Instruments and Dyes" Clinical Chemistry 52(3):494-503 (2006).

(Continued)

*Primary Examiner* — John S Brusca
(74) *Attorney, Agent, or Firm* — Rothwell, Figg, Ernst & Manbeck, P.C.

(57) ABSTRACT

The present invention relates to methods and systems for the analysis of the dissociation behavior of nucleic acids and the identification of determining whether a genotype is present in a biological sample. This includes methods and systems for determining whether a genotype is present in a biological sample, through generating a dynamic profile an unknown genotype, correlating the dynamic profile to an average profile for a known genotype to generate a correlation value, and determining whether the correlation value falls within an acceptable threshold to determine if the unknown genotype is the known genotype. The present invention also relates to methods and systems for generating a training set to allow a machine to recognize a known genotype from within a class of known genotypes. The training set generated by these methods and systems may be used to assist in identification of unknown genotypes.

53 Claims, 30 Drawing Sheets

OTHER PUBLICATIONS

Ihara et al., "Ferrocene-oligonucleotide conjugates for electrochemical probing of DNA," Nucleic Acids Research, vol. 24, No. 21, pp. 4273-4280 (1996).

Kopp et al., "Chemical Amplification: Continuous-Flow PCR on a Chip," Science, 280(15), pp. 1046-1048 (1998).

Lagally et al., "Single-Molecule DNA Amplification and Analysis in an Integrated Microfluidic Device," Analytical Chemistry, 73(3), pp. 565-570 (2001).

Lai et al., "Rapid, sequence-specific detection of unpurified PCR amplicons via a reusable, electrochemical sensor," Proc. Natl. Acad. Sci. U.S.A., vol. 103, pp. 4017-4021 (2006).

Lee et al., "In vitro cytotoxicity of GC sequence directed alkylating agents related to distamycin," J. Med. Chem., col. 36, No. 7, pp. 863-870 (1993) (abstract).

Liew, M., et al. "Genotyping of Single-Nucleotide Polymorphisms by High-Resolution Melting of Small Amplicons," Clin.Chem. vol. 50, No. 7, pp. 1156-1164 (2004).

Mearns et al., "DNA Biosensor Concepts Based on a Change in the DNA Persistence Length upon Hybridization," Electroanalysis, vol. 18, pp. 1971-1981 (2006) (abstract).

Mikkelsen, "Electrochemical biosensors for DNA sequence detection," Electroanalysis, vol. 8, pp. 15-19 (1996) (abstract).

Montgomery, J., et al. "Simultaneous mutation scanning and genotyping by high-resolution DNA melting analysis," Nat.Protoc. 2(1) (2007): 59-66. (abstract).

Odenthal et al. "An introduction to electrochemical DNA biosensors," Analyst, vol. 132, pp. 603-610 (2007).

Palecek et al., "From polarography of DNA to microanalysis with nucleic acid-modified electrode," Electroanalysis, vol. 8(1), pp. 7-14 (1996) (abstract).

Park et al., "Cylindrical compact thermal-cycling device for continuous-flow polymerase chain reaction," Analytical Chemistry, 75, pp. 6029-6033 (2003).

Paterlini et al., "High performance clustering with differential evolution," Proceedings of the 2004 Congress on Evolutionary Computation, pp. 2004-2011 (2004).

Peyret et al., "Nearest neighbor thermodynamics and NMR of DNA sequences with internal A.A, C.C, G.G, and T.T mismatches," Biochemistry 1999; 38:3468-77 (abstract).

Poser et al., "Chip elements for fast thermocycling," Sensors and Actuators A, vol. 62, pp. 672-675 (1997) (abstract).

Ririe et al., "Product Differentiation by Analysis of DNA Melting Curves During the Polymerase Chain Reaction," Analytical Biochemistry 245:154-160 (1997) (abstract).

Santalucia et al., "Improved nearest-neighbor parameters for predicting DNA duplex stability," Biochemistry, vol. 35, pp. 3555-3562 (1996).

Schneegass et al., "Flow-through Polymerase chain Reactions in Chip Thermocyclers," Reviews in Molecular Biotechnology, vol. 82, pp. 101-121 (2001).

Wittwer et al., "High-Resolution Genotyping by Amplicon Melting Analysis Using LCGreen," Clinical Chemistry, vol. 49, No. 6, pp. 853-860 (2003).

Xiao et al., "Single-step electronic detection of femtomolar DNA by target-induced strand displacement in an electrode-bound duplex," Proc. Natl. Acad. Sci. U.S.A., vol. 103, pp. 16677-16680 (2006).

Zhou, L., et al. "High-resolution DNA Melting Analysis for Simultaneous Mutation Scanning and Genotyping in Solution," Clin. Chem. vol. 51, No. 10, pp. 1770-1777 (2005).

* cited by examiner

RAPID METHOD OF PATTERN RECOGNITION, MACHINE LEARNING, AND AUTOMATED GENOTYPE CLASSIFICATION THROUGH CORRELATION ANALYSIS OF DYNAMIC SIGNALS

CROSS-REFERENCE TO RELATED APPLICATIONS

This application claims the benefit of U.S. Patent Application Ser. No. 61/168,649, filed on Apr. 13, 2009, which is incorporated herein by reference in its entirety.

BACKGROUND

1. Field of the Invention

The present invention relates to methods for the analysis of nucleic acids and the identification of genotypes present in biological samples. More specifically, embodiments of the present invention relate to automated methods for genotyping and analyzing the sequences of nucleic acids.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification in microfluidic devices is usually accomplished in one of two methods. In the first method, the sample solution is loaded into the device and the temperature is cycled in time, much like a conventional PCR instrument. In the second method, the sample solution is pumped continuously through spatially varying temperature zones. See, e.g., Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA). The process of causing DNA to transition from dsDNA to ssDNA with increasing temperature is sometimes referred to as a "high-resolution temperature (thermal) melt (HRTm)" process, or simply a "high-resolution melt" process. Alternatively, the transition from ssDNA to dsDNA may be observed through various electrochemical methods, which generate a dynamic current as the potential across the system is changed.

Melting profile analysis is an important technique for analyzing nucleic acids. In some methods, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is raised, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence. See, e.g., Ririe et al. (*Anal Biochem* 245:154-160, 1997), Wittwer et al. (*Clin Chem* 49:853-860, 2003), Liew et al. (*Clin Chem* 50:1156-1164 (2004), Herrmann et al. (*Clin Chem* 52:494-503, 2006), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253), Sundberg et al. (U.S. Patent Application Publication No. 2007/0026421) and Knight et al. (U.S. Patent Application Publication No. 2007/0231799).

An alternative method for analyzing a nucleic acid uses voltammetry to detect electrochemical biosensors to detect nucleic acid hybridization. Electrochemical technology is miniaturizable, accurate, and sensitive with controlled reaction conditions. Both label-free and labeled approaches exist for detecting nucleic acid hybridization. Label-free approaches generally rely on changes to the electrical properties of an interface when bound to a nucleic acid, changes in flexibility between rigid dsDNA and more flexible ssDNA, or electrochemical oxidation of guanine bases. See, e.g., Gooding (*Electroanalysis* 14:1149-1156, 2002), Gooding et al. (*Chem. Commun.* 2003:1938-1939, 2003), Mearns et al. (*Electroanalysis* 18:1971-1981, 2006); Paleck (*Electroanalysis* 8:7-14, 1996). Labeled approaches for detecting nucleic acid hybridization are more common and well-known than label-free approaches. These approaches generally involve redox active molecules that intercalate between Watson-Crick base pairs of a nucleic acid or in the minor or major grooves of the nucleic acid secondary structure, and thus do not interact with single-stranded nucleic acids. Examples of such redox active molecules include $Co(Phen)_3^{3+}$, $Co(bpy)_3^{3+}$, and Methylene Blue. See, e.g., Mikkelsen (*Electroanalysis* 8:15-19, 1996); Erdem et al. (*Anal. Chim. Acta* 422:139-149, 2000). In some cases, the redox active molecules bind preferentially to either dsDNA or ssDNA. Another alternative method includes attaching a label group, such as a ferrocene group, to the end of a nucleic acid probe, which is immobilized on an electrode surface. See, e.g., Mearns et al. (*Electrochemistry* 18:1971-1981, 2006); Anne et al. (*J. Am. Chem. Soc.* 128:542-547, 2006); Lai et al. (*Proc. Natl. Acad. Sci. U.S.A.* 103:4017-4021, 2006); Fan et al. (*Proc. Natl. Acad. Sci. U.S.A.* 100:9134-9147, 2003); Xiao et al. (*Proc. Natl. Acad. Sci. U.S.A.* 103:16677-16680, 2006). The single-stranded probe molecule is flexible enough that the ferrocene group may come within close enough contact with the electrode surface to be oxidized or reduced. However, upon hybridization, the rigid double-stranded nucleic acid molecule stands normal to the electrode surface, and the ferrocene group is sufficiently far from the electrode that it will not be oxidized or reduced.

These systems may all be interrogated through cyclic voltammetry. By applying an electric potential that increases or decreases over time across the system, a variable electric current is generated as the label or DNA molecule is oxidized or reduced. Complete hybridization of the target molecule to the probe molecule will generate a characteristic dynamic profile of current generated versus voltage applied. Incomplete hybridization, which would occur if the target molecule contained a mutant genotype, would result in a differing dynamic profile of current generated versus voltage applied. Thus, different nucleic acid sequences may be distinguished from one another through examination of their respective voltammograms.

Some nucleic acid assays require differentiation between potential genotypes within a class of known genotypes. Generally, for thermal melt analysis, researchers will visually inspect a thermal melt profile to determine the melting temperature of the nucleic acid in the sample. However, some nucleic acid assays require identification of a single nucleotide change where the difference in melting temperature ($T_m$) between the wild type nucleic acid and a mutant nucleic acid is quite small (e.g. less than 0.25° C.). This level of temperature resolution is difficult to achieve in a visual inspection. Furthermore, visual inspection of thermal melt profiles to determine melting temperature ignores significant additional information contained in the profiles, such as the overall shape and distribution of the profile.

Accordingly, what are desired are methods and systems for high resolution melt analysis that are capable of more accurately discriminating thermal melt curves and obtaining DNA sequence information from these melting curves, especially where these thermal melt curves are differentiated by a small temperature range. Also desired are methods and systems for high resolution melt analysis that more accurately identify thermal melt curves that facilitate detection of sequence information for DNA that contain one or more peaks or mutations. Also desired are methods and systems for that are capable of more accurately identifying a nucleic acid sequence and discriminating between similar sequences while taking into account both features of the profile as well as the overall shape. Also desired are methods that are capable of rapidly identifying a genotype with minimal intervention and decision-making from the user.

SUMMARY OF THE INVENTION

The present invention relates to methods and systems for the analysis of nucleic acids and the identification of genotypes present in biological samples. More specifically, embodiments of the present invention relate to automated methods and systems to analyze the sequences of nucleic acids and to classify their genotypes that are useful for determining the identity of the genotype of a nucleic acid that is present in a biological sample.

Thus, in one aspect, the present invention provides a method of determining the identity of the genotype of a nucleic acid present in a biological sample. According to this aspect, the method comprises the steps of generating a dynamic profile of an unknown genotype contained in the biological sample. The dynamic profile comprises measurements of a signal representing a physical change of a nucleic acid containing the unknown genotype relative to an independent variable. The method also comprises correlating the dynamic profile of the unknown genotype with an average dynamic profile of each known genotype in a class of known genotypes to generate a correlation vector. The average dynamic profile of each known genotype comprises average measurements of the signal representing the physical change of a nucleic acid containing the known genotype relative to the independent variable. The correlation vector comprises correlation coefficients between the dynamic profile of the unknown genotype and the average dynamic profile for each known genotype in the class of known genotypes. The method further comprises determining whether the correlation vector or a transformation thereof falls within an acceptable range to classify the unknown genotype as one of the known genotypes, whereby the identity of the genotype in the biological sample is determined.

In one embodiment, the average profiles for the known genotypes are obtained from a training set which can be prepared as described herein. In another embodiment, the independent variable can be temperature. In a further embodiment, physical change can be denaturation of the nucleic acid. In another embodiment, the signal representing denaturation of the nucleic acid is fluorescence. In a further embodiment, the independent variable is electric potential. In another embodiment, the physical change is oxidation of a redox-active molecule in the biological sample. In a further embodiment, the signal representing oxidation of the redox-active molecule is current. In another embodiment, a posterior probability that the unknown genotype is a known genotype is calculated for each known genotype from the correlation coefficients. In another embodiment, the method is automated. In a further embodiment, the method uses a computer.

In a further embodiment, the determination step comprises determining whether the largest posterior probability and the correlation coefficient against the average dynamic profile for the corresponding genotype fall within acceptable predefined thresholds to classify the unknown genotype and thereby identify it. In another embodiment the correlation step includes calculating a likelihood of the unknown genotype being a known genotype for each of the known genotypes in the class of known genotypes using class conditional densities of each known genotype. The correlation step also comprises calculating the posterior probability that the biological sample contains each known genotype from the calculated likelihoods. In one embodiment, the posterior probability is calculated using Bayes' theorem. In another embodiment, the class conditional densities are calculated using mean transformed vectors (also referred to as mean vectors herein) and covariance matrices for each genotype. In one embodiment, the mean transformed vectors and covariance matrices are obtained from a matrix comprising grouped transformed vectors for each genotype obtained from a training set. In another embodiment, the correlation vector is transformed to a vector in which each element of the transformed vector is normally distributed. In a further embodiment, the elements of the transformed vector are expressed as spherical coordinates. In another embodiment, the dynamic profile is normalized to have a predetermined mean and standard deviation.

In another embodiment, the method of determining the identity of the genotype of a nucleic acid present in a biological sample further includes the step of correcting for a shift and scale changes of the independent variable through the use of positive control dynamic profiles. Thus, the method of this first aspect further comprises the steps of (1) generating a positive control dynamic profile of a control genotype, wherein the positive control dynamic profile comprises measurements of a signal representing a physical change of a nucleic acid containing the control genotype relative to an independent variable, (2) comparing the positive control dynamic profile to a standard reference control dynamic profile for the control genotype to determine a shift value for the independent variable, and (3) shifting the independent variable of the dynamic profile of the positive control and the dynamic profile of the unknown genotype by the shift value.

In a second aspect, the present invention provides a method of generating a training set to allow a machine to recognize a known genotype from within a class of known genotypes. This training set is particularly useful in the method of determining the identity of the genotype of a nucleic acid present in a biological sample described herein. The training set allows a machine, e.g., a computer, to recognize a known genotype from within a class of known genotypes so that later an unknown genotype can be classified. According to this second aspect of the invention, the method comprises grouping multiple dynamic profiles of the same genotype for each known genotype in a class of known genotypes. Each dynamic profile comprises measurements of a signal representing a physical change of a nucleic acid containing the known genotype relative to an independent variable. The method also comprises normalizing each of the dynamic profiles and averaging the normalized dynamic profiles of the same genotype to obtain an average normalized dynamic profile for each known genotype in the class of known genotypes. The method further comprises correlating each dynamic profile with the average normalized dynamic profile of each known genotype in the class of known genotypes to generate a correlation vector for each dynamic profile. Each correlation vector comprises correlation coefficients for the dynamic profile against each average normalized dynamic profile of each known genotype in the class of known genotypes.

The method of this second aspect of the invention also comprises transforming the correlation vectors such that when grouped together by genotype, each of the elements of the transformed vector is normally distributed. In addition, the method comprises compiling each transformed vector into a matrix of transformed vectors, such that there is one matrix for each known genotype in the class of known genotypes. The method further comprises (i) generating a mean transformed vector whose elements include an average transformed vector for each known genotype where the transformed vector is the average of each compiled matrix and (ii) calculating a covariance matrix for the known genotypes by calculating the covariance matrix of each of the compiled matrices. Thus, the training set comprises the average normalized dynamic profile for each known genotype, a mean transformed vector for each known genotype and a covariance matrix for each known genotype.

In one embodiment, the method of generating a training set further includes the step of correcting for shift and scale changes in the sensed independent variable through the use of positive control dynamic profiles as described above. In this embodiment, the independent variable of the dynamic profile of the positive control and the dynamic profiles of the known genotypes are shifted by the shift value. In a further embodiment, each dynamic profile is normalized to have a predetermined mean and standard deviation.

In another embodiment, the method further includes the step of translating each correlation vector into n-spherical coordinates, where n is one fewer than the number of genotypes that make up all of the possible mutations. In one embodiment, the method includes the step of translating each correlation vector in to spherical coordinates. In yet another embodiment, each dynamic profile includes measurements of a signal representing a physical change of each nucleic acid containing each known genotype relative to an independent variable measured over a range selected to maximize the separation between dynamic profiles for different known genotypes within the class of known genotypes, while minimizing the separation between dynamic profiles of the same known genotype.

In another aspect, the present invention provides a method of determining the identity of the genotype of a nucleic acid present in a biological sample. In accordance with this aspect, the invention comprises generating a dynamic profile of an unknown genotype contained in a biological sample. The dynamic profile comprises measurements of a signal representing a physical change of a nucleic acid containing the unknown genotype relative to an independent variable. The method also comprises correlating the dynamic profile of the unknown genotype with an average dynamic profile of each known genotype in a class of known genotypes to generate a correlation vector. The average dynamic profile of each known genotype is provided in a training set and comprises average measurements of a signal representing the physical change of a nucleic acid containing the known genotype relative to the independent variable. The correlation vector comprises correlation coefficients between the dynamic profile of the unknown genotype and the average dynamic profile for each known genotype in the class of known genotypes.

The method further comprises calculating a likelihood of the unknown genotype being a known genotype for each of the known genotypes in the class of known genotypes using class conditional densities of each known genotype. The class conditional densities are calculated using mean transformed vectors and covariance matrices for each genotype. The mean transformed vectors and matrices are obtained from a matrix comprising grouped transformed vectors for each genotype obtained from the training set. In addition, the method comprises calculating the posterior probability that the biological sample contains each known genotype from the calculated likelihoods. The method further comprises determining whether the posterior probability that the biological sample contains a genotype falls within an acceptable threshold to determine if the unknown genotype is classified as one of the known genotypes, whereby the identity of the genotype of the nucleic acid in the biological sample is determined.

In one embodiment, the posterior probability is calculated using Bayes' theorem. In another embodiment, the method further comprises the step of correcting for a shift and scale changes of the independent variable through the use of positive control dynamic profiles as described above. In a further embodiment, each dynamic profile is normalized to have a predetermined mean and standard deviation. In another embodiment, the training set utilized in this aspect of the invention is prepared as described herein. In another embodiment, each dynamic profile is normalized to have a predetermined mean and standard deviation. In a further embodiment, the training set is prepared with a step of correcting for a shift and scale changes of the independent variable through the use of positive control dynamic profiles as described above.

In a still further embodiment, the posterior probabilities that fall within the acceptable threshold are greater than 95%. In another embodiment, the method further comprises determining whether the correlation vector falls within an acceptable range to determine if one of the known genotypes is identical to the unknown genotype present in the biological sample. In one embodiment, the acceptable range is an ellipsoid defined by the eigenvectors of the covariance matrix of the training set that contains a predefined threshold percentage of the measurements of the signal relative to the independent variable within the dynamic profile. In another embodiment, the elements of the correlation vector are transformed to a vector with the same number of elements where each element is normally distributed. In another embodiment, the method further comprises translating each correlation vector into n-spherical coordinates, wherein n is one fewer than the number of genotypes that make up all of the possible mutations.

In an additional embodiment, the method further comprises the steps of: (a) calculating a within-class scatter matrix for the class of known genotypes using the mean transformed vector and the parameter matrix for each genotype; calculating a between-class scatter matrix for the class of known genotypes using the mean transformed vector and the parameter matrix for each genotype; (c) determining a separation ratio that is the ratio of the determinant of the within-class scatter matrix to the determinant of the between-class scatter matrix; and determining a separation-maximizing range for the independent variable, wherein the separation-maximizing range is selected to maximize the separation ratio. In this embodiment, each dynamic profile comprises measurements of a signal representing a physical change of each nucleic acid containing each known genotype relative to an independent variable measured over the separation-maximizing range.

In another aspect, the invention provides a system for determining the identity of the genotype of a nucleic acid present in a biological sample. In accordance with this aspect, the system comprises a generation module, a correlation module, a class-conditional density module, a posterior probability module, and a determination module. The generation module is capable of generating a dynamic profile of an unknown genotype contained in a biological sample. The dynamic profile comprises measurements of a signal representing a physical change of a nucleic acid containing the unknown genotype relative to an independent variable. The correlation module is capable of correlating the dynamic profile of the unknown genotype with an average dynamic profile for each known genotype in a class of known genotypes to generate a correlation vector. The average dynamic profile of each known genotype is provided in a training set and comprises average measurements of a signal representing the physical change of a nucleic acid containing the known genotype relative to the independent variable. The correlation vector comprises correlation coefficients between the dynamic profile of the unknown genotype and the average dynamic profile for each known genotype in the class of known genotypes.

The class-conditional density module is capable of calculating the likelihood of the unknown genotype being a known genotype for each of the known genotypes in the class of known genotypes using the class conditional densities of each of the known genotypes. The class conditional densities are calculated using mean transformed vectors and covariance matrices for each genotype. The mean transformed vectors and covariance matrices are obtained from a matrix comprising grouped transformed vectors for each genotype obtained from the training set. The posterior probability module is capable of calculating the posterior probability that the biological sample contains each known genotype from the calculated likelihoods. The determination module is capable of determining whether the known genotype with the largest posterior probability falls within an acceptable threshold to determine if the unknown genotype is classified as the genotype with the largest posterior probability, whereby the identity of the genotype in the biological sample is determined.

In one embodiment, the posterior probability module uses Bayes' theorem to calculate the posterior probability. In another embodiment, the system further comprises an error correction module. The error correction module is capable of comparing a positive control profile to a known profile for a control genotype to determine a shift value for the independent variable. The error correction module is capable of performing a shift of the independent variable in the dynamic profile for the unknown genotype by the shift value.

In a further embodiment, the system also comprises a training set module comprises an average dynamic profile for each known genotype in the class of known genotypes and a parameter matrix. The elements of the parameter matrix are correlation vectors. Each correlation vector includes a correlation coefficient between a dynamic profile and each average dynamic profile for each known genotype in the class of known genotypes. In another embodiment, the average dynamic profile is an average normalized dynamic profile.

In an additional embodiment, the training set module further comprises a mean transformed vector whose elements include average values of the correlation coefficients of each dynamic profile of each known genotype against each average dynamic profile for each known genotype in the class of known genotypes, and a covariance matrix for the known genotypes obtained by calculating the covariance matrix of the parameter matrix. In one embodiment, the average dynamic profile is an average normalized dynamic profile.

In one embodiment, the correlation module further transforms the correlation vector to a transformed vector in which each element of the transformed vector is normally distributed. In another embodiment, the determination module is further capable of determining whether the transformed vector falls within an acceptable threshold within those obtained from the training set for the genotype with the largest posterior probability. In a further embodiment, the acceptable range is an ellipsoid defined by the eigenvectors of the covariance matrix of the training set that contains a predefined threshold percentage of the measurements of the signal relative to the independent variable within a dynamic profile. In another embodiment, the system further comprises a translation module. The translation module is capable of translating a correlation vector into n-spherical coordinates, wherein n is one fewer than the number of genotypes that make up all of the possible mutations. In one embodiment, this translation may generate parameters that are normally distributed. In another embodiment, the translation module is capable of translating a correlation vector into spherical coordinates. In this embodiment, the translation may generate parameters that are normally distributed. In a further embodiment, the system also comprises a separation-maximizing range selection module that is capable of determining a separation-maximizing range for the independent variable as described above.

BRIEF DESCRIPTION OF THE FIGURES

The accompanying drawings, which are incorporated herein and form part of the specification, illustrate various embodiments of the present invention.

DETAILED DESCRIPTION OF PREFERRED EMBODIMENTS

Figure 1A:
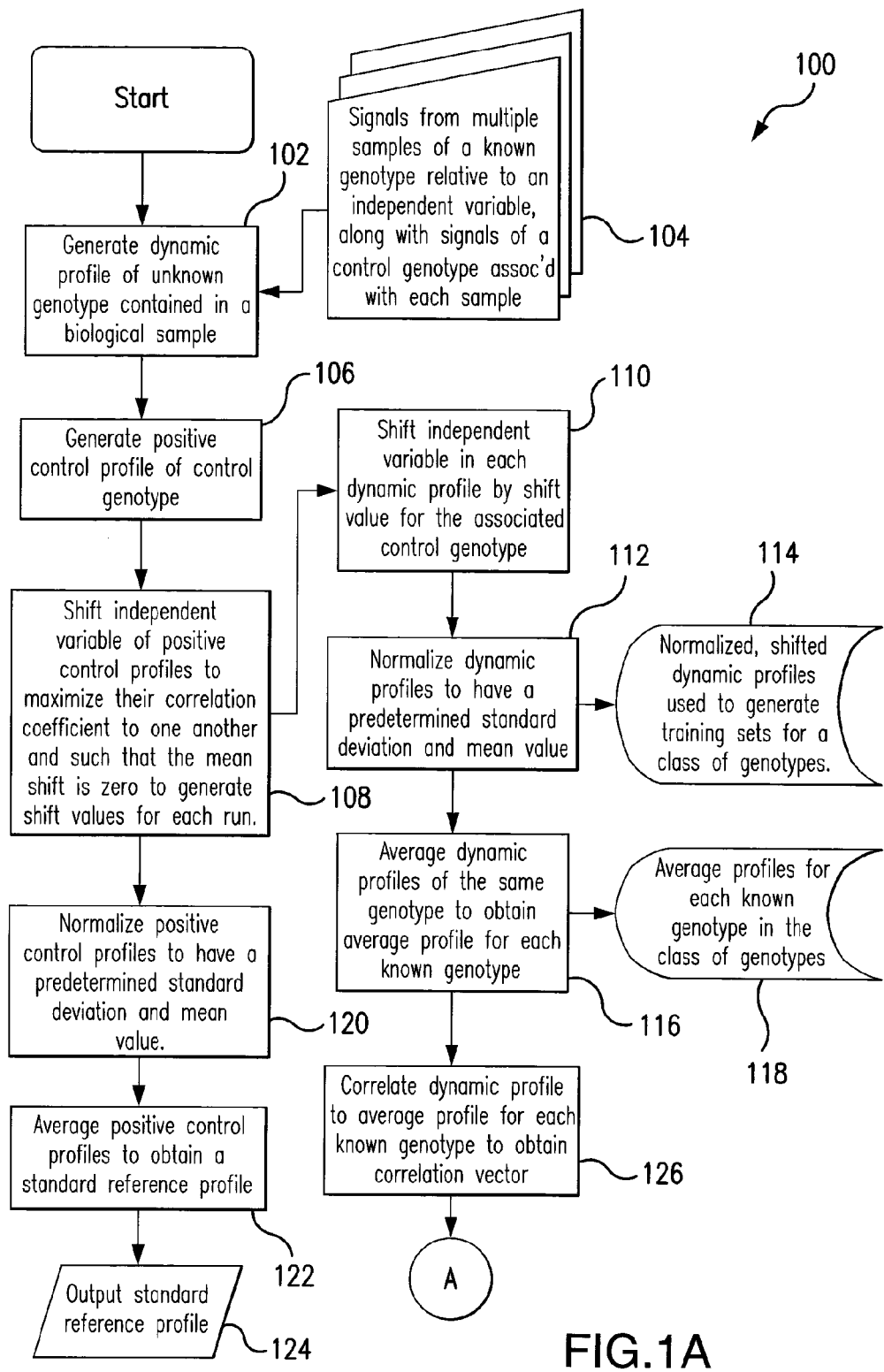
FIGS. 1A and 1B illustrate a flowchart showing a method of generating a training set to recognize a known genotype from within a class of known genotypes in accordance with embodiments of the present invention.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using*

*Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger, *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

Thermal melt curves of fluorescence have been used to determine the melting temperature of a DNA strand when denatured from the duplex state to the two separate single strands via a ramp increase in temperature. Typically, the melting temperature or $T_m$ is defined to be the temperature at which 50% of the paired DNA strands have denatured into single strands. Intercalating dyes that fluoresce when bound to double stranded DNA and lose their fluorescence when denatured are often used in measuring $T_m$. Typically, the negative derivative of fluorescence with respect to temperature ($-dF/dT$) has been used in the determination of $T_m$. In typical systems, the temperature at the peak $-dF/dT$ is used as an estimate of the melting temperature $T_m$.

The $-dF/dT$ derivative curve may be obtained using a Savitsky-Golay (SG) derivative filter which is capable of estimating the derivative of any signal. Savitsky-Golay filters are low pass, Finite Impulse Response (FIR) derivative filters, and their application to any dynamical signal is obtained through the convolution of the FIR filter parameters with the raw signal. When the spacing of the independent variable is uniform, the filtered results can give first order and higher order derivatives of the dependant variable relative to the independent variable equivalent. The effect of such a filter is equivalent to a moving polynomial fit, followed by the evaluation of the derivative of that polynomial evaluated at the center of the window. Other methods for obtaining the $-dF/dT$ derivative curve may be found in U.S. Patent Application Publication No. 2009/0112484, which is incorporated herein by reference.

The present invention relates to methods and systems for the analysis of dynamic profiles of nucleic acids. These dynamic profiles are data sets containing measurements of a signal representing a physical change of a nucleic acid relative to an independent variable. One example of this physical change is the dissociation behavior of nucleic acids. The analysis of the dynamic profiles of nucleic acids of a particular genotype can assist in the identification of nucleic acids and the identification of particular genotypes. More specifically, the present invention relates to methods and systems for determining the identity of the genotype of a nucleic acid present in a biological sample through analysis of dynamic profiles of an unknown genotype in a biological sample.

As stated above, a dynamic profile contains measurements of a signal representing a physical change of a nucleic acid relative to an independent variable. This physical change may be, for example, denaturation of a nucleic acid containing a particular genotype. Such a dynamic profile may be, for instance, a molecular melt curve or a thermal denaturation curve. The signal in such a thermal denaturation curve for nucleic acids may be, for example, measured thermal parameters, fluorescence of indicator dyes/molecules, fluorescence polarization, dielectric properties, or the like. A dynamic profile which is a molecular melt curve or a thermal denaturation curve may be generated by melting curve analysis.

Melting curve analysis is typically carried out either in a stopped flow format or in a continuous flow format. In one example of a stopped flow format, flow is stopped within a microchannel of a microfluidic device while the temperature in that channel is ramped through a range of temperatures required to generate the desired melt curve. In an alternative stopped flow format, melting curve analysis is done in a chamber to which the nucleic acid sample has been added. In one example of a continuous flow format, a melting curve analysis is performed by applying a temperature gradient along the length (direction of flow) of a microchannel of a microfluidic device. If the melting curve analysis requires that the molecules being analyzed be subjected to a range of temperatures extending from a first temperature to a second temperature, the temperature at one end of the microchannel is controlled to the first temperature, and the temperature at the other end of the length is controlled to the second temperature, thus creating a continuous temperature gradient spanning the temperature range between the first and second selected temperatures. An example of an instrument for performing a melting curve analysis is disclosed in U.S. Patent Application Publication No. 2007/0231799, incorporated herein by reference in its entirety. Although the present invention is applicable to the analysis of dynamic profiles obtained in any environment, it is particularly useful for dynamic profiles obtained in the microfluidic environment because of the need for greater sensitivity in this environment.

In accordance with certain aspects of the invention, dynamic profiles are generated by elevating the temperature of a molecule or molecules, e.g., of one or more nucleic acids, for a selected period of time and measuring a signal (i.e. a detectable property) emanating from the molecule or molecules, wherein the signal indicates an extent of denaturation of the nucleic acid. This period of time can range, for example, from about 0.01 second through to about 1.0 minute or more, from about 0.01 second to about 10 seconds or more, or from about 0.1 second to about 1.0 second or more, including all time periods in between. In one embodiment, heating comprises elevating the temperature of the molecule or molecules by continuously increasing the temperature of the molecule or molecules. For example, the temperature of the molecule(s) can be continuously increased at a rate in the range of about 0.1° C./second to about 1° C./second. Alternatively, the temperature of the molecule(s) can be continuously increase at a slower rate, such as a rate in the range of about 0.01° C./second to about 0.1° C./second, or at a faster rate, such as a rate in the range of about 1° C./second to about 10° C./second. The heating can occur through application of an internal or an external heat source, as is known in the art.

The actual detection of one or more physical changes of the molecules can be detected in numerous methods depending on the specific molecules and reactions involved. For example, the denaturation of the molecules can be tracked by following fluorescence or emitted light from molecules in the assay. The degree of, or change in, fluorescence is correlational or proportional to the degree of change in conformation of the molecules being assayed. Thus, in some methods, the detection of a property of the molecule(s) comprises detecting a level of fluorescence or emitted light from the molecules (s) that varies as a function of relative amounts of binding. In one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule.

Dynamic profiles may be generated in a number of different methods. In some methods, the generation of the dynamic profile includes providing one molecule comprising a fluorescence indicator dye or fluorescence indicator molecule, and at least a second molecule comprising, one or more of an enzyme, a ligand, a peptide nucleic acid, a cofactor, a receptor, a substrate, a protein, a polypeptide, a nucleic acid (either double-stranded or single-stranded), an antibody, an antigen, or an enzyme complex. Fluorescence of the first molecule in the presence of the second molecule as a function of temperature is measured and the resulting data constitutes a dynamic profile. In other methods, the generation of the dynamic profile comprises measuring a change in the fluorescence of one molecule that is correlative or proportional to a change in a physical property of another molecule(s) due to a change in temperature. In still other methods, the generation of a dynamic profile comprises measuring the change in the total free energy of the system as a function of temperature without the presence of a second molecule. Typically, the methods also include generating a positive control profile of a control sample, or a known dynamic profile of a known sample, in a similar manner.

Several techniques exist for the measurement of the denaturation of the molecules of interest, and any of these can be used in generating the data to be analyzed in accordance with aspects of the present invention. Such techniques include fluorescence, fluorescence polarization, fluorescence resonance energy transfer, circular dichroism and UV absorbance. Briefly, the fluorescence techniques involves the use of spectroscopy to measure changes in fluorescence or light to track the denaturation/unfolding of the target molecule as the target molecule is subjected to changes in temperature. Spectrometry, e.g. via fluorescence, is a useful method of detecting thermally induced denaturation/unfolding of molecules. Many different methods involving fluorescence are available for detecting denaturation of molecules (e.g. intrinsic fluorescence, numerous fluorescence indicator dyes or molecules, fluorescence polarization, fluorescence resonance energy transfer, etc.) and are optional embodiments of the present invention. These methods can take advantage of either internal fluorescent properties of target molecules or external fluorescence, i.e. the fluorescence of additional indicator molecules involved in the analysis.

A method of measuring the degree of denaturation/unfolding of the target molecule is through monitoring of the fluorescence of dyes or molecules added to the microfluidic device along with the target molecule and any test molecules of interest. A fluorescence dye or molecule refers to any fluorescent molecule or compound (e.g., a fluorophore) which can bind to a target molecule either once the target molecule is unfolded or denatured or before the target molecule undergoes conformational change by, for example, denaturing and which emits fluorescent energy or light after it is excited by, for example, light of a specified wavelength.

One dye type used in the microfluidic devices is one that intercalates within strands of nucleic acids. The classic example of such a dye is ethidium bromide. An exemplary use of ethidium bromide for binding assays includes, for example, monitoring for a decrease in fluorescence emission from ethidium bromide due to binding of test molecules to nucleic acid target molecules (ethidium bromide displacement assay). See, e.g., Lee, M. et al. (*J Med Chem* 36(7):863-870 (1993)). The use of nucleic acid intercalating agents in measurement of denaturation is known to those in the art. See, e.g., Haugland (*Handbook of Fluorescent Probes and Research Chemicals*, Molecular Probes, Inc., Eugene, Oreg. (1996)).

Dyes that bind to nucleic acids by mechanisms other than intercalation can also be employed in embodiments of the invention. For example, dyes that bind the minor groove of double stranded DNA can be used to monitor the molecular unfolding/denaturation of the target molecule due to temperature. Examples of suitable minor groove binding dyes are the SYBR Green family of dyes sold by Molecular Probes Inc. (Eugene, Oreg., USA). See, e.g., Haugland (*Handbook of Fluorescent Probes and Research Chemicals*, Molecular Probes, Inc., Eugene, Oreg., USA (1996)). SYBR Green dyes will bind to any double stranded DNA molecule. When a SYBR Green dye binds to double stranded DNA, the intensity of the fluorescent emissions increases. As more double stranded DNA are denatured due to increasing temperature, the SYBR Green dye signal will decrease. Another suitable dye is LCGreen Plus sold by Idaho Technology, Inc. (Salt Lake City, Utah, USA).

Fluorescence polarization (FP) provides a useful method to detect hybridization formation between molecules of interest. This method is especially applicable to hybridization detection between nucleic acids, for example, to monitor single nucleotide polymorphisms (SNPs). Generally, FP operates by monitoring, the speed of rotation of fluorescent labels, such as fluorescent dyes or molecular beacons, e.g. before, during, and/or after binding events between molecules that comprise the test and target molecules. In short, binding of a test molecule to the target molecule ordinarily results in a decrease in the speed of rotation of a bound label on one of the molecules, resulting in a change in FP.

Fluorescence resonance energy transfer (FRET) can be used to track the conformational changes of the target molecule (and interactions with test molecules which can bind with the target molecule) as a function of temperature. FRET relies on a distance-dependent transfer of energy from a donor fluorophore to an acceptor fluorophore. If an acceptor fluorophore is in close proximity to an excited donor fluorophore, then the emission of the donor fluorophore can be transferred to the acceptor fluorophore. This causes a concomitant reduction in the emission intensity of the donor fluorophore and an increase in the emission intensity of the acceptor fluorophore. Since the efficiency of the excitation transfer depends, inter alia, on the distance between the two fluorophores, the technique can be used to measure extremely small distances such as would occur when detecting changes in conformation. This technique is particularly suited for measurement of binding reactions, protein-protein interactions, e.g., such as a protein of interest binding to an antibody and other biological events altering the proximity of two labeled molecules. Many appropriate interactive labels are known. For example, fluorescent labels, dyes, enzymatic labels, and antibody labels are all appropriate.

Circular dichroism (CD) can be used to follow the conformational changes of the target molecules/text molecules as a function of temperature and can be used to construct molecular melt curves. CD is a type of light absorption spectroscopy which measures the difference in absorbance by a molecule between right-circularly polarized light and left-circularly polarized light. CD is quite sensitive to the structure of polypeptides and proteins.

UV absorbance can also be used to detect and/or track denaturation of nucleic acid molecules, and/or to quantify the total amount of nucleic acid. UV can be employed to measure the extent of denaturation because the UV absorbance value of single stranded nucleic acid molecules is greater than the absorbance value of double stranded nucleic acid molecules.

An alternative method of measuring the degree of denaturation/unfolding of the target molecule is through monitoring of the current generated by a sample relative to the voltage applied across the sample to generate a voltammetry curve. In some methods, the generation of a voltammetry curve includes providing one molecule comprising one or more of an enzyme, a ligand, a peptide nucleic acid, a cofactor, a receptor, a substrate, a protein, a polypeptide, a nucleic acid (either double-stranded or single-stranded), an antibody, an antigen, or an enzyme complex. In addition, at least one second molecule comprising a redox-active molecule that preferentially binds to either a single-stranded nucleic acid or a double-stranded nucleic acid is provided. Generally, a probe molecule is provided which represents a particular protein or nucleic acid of interest; the probe molecule may be a ligand, a peptide nucleic acid, a substrate, a protein, a polypeptide, a nucleic acid (either double-stranded or single-stranded, and may be an oligonucleotide which is capable of hybridizing to a specific sequence of interest), an antibody, an antigen, or an enzyme complex. Preferably, the redox-active molecule interacts with a double-stranded nucleic acid in such a way that its oxidation or reduction potential is different than when it does not interact with a double-stranded nucleic acid. Such redox-active molecules often intercalate between Watson-Crick base pairs of a nucleic acid or in the minor or major grooves of the nucleic acid secondary structure, and thus do not interact with single-stranded nucleic acids. Alternatively, the redox-active molecule may bind preferentially to a sequence of interest. A non-limiting example of such a redox-active molecule is a probe molecule containing a sequence of interest to be interrogated and a ferrocene label attached at a free end of the probe.

Application of an electric potential across a sample containing such a redox-active molecule will generate an electric current, which will vary with the application of different electric potentials. By applying a range of electric potential across the sample, various measurements of electric current generated may be obtained in order to create a dynamic profile. For example, if the first molecule has completely hybridized to the probe molecule, the dynamic profile will differ from one generated if the first molecule incompletely hybridizes to the probe molecule, or does not hybridize at all. The dynamic profile may then be plotted as a curve representing current versus voltage in order to generate a voltammetry curve. The processes and flow charts described herein for the dynamic profile in the case of high resolution thermal melt would apply to the dynamic profile in the case of electrochemical voltammetry.

The dynamic profile generated through these methods may be plotted on any available medium used for plotting data to generate a signature curve. Signature curves are useful because they allow a person to visually match one dynamic profile to another, which may allow a researcher to discriminate between different genotypes in a biological sample. An initial signature curve may also be mathematically modified or operated upon in order to generate a second signature curve, which may allow a researcher to more easily compare a signature curve representing an unknown genotype to one representing a known genotype. A signature curve may be, for instance, a thermal melt curve. Thermal melt curves are generally plots of the negative derivative of fluorescence with respect to temperature (−dF/dT), which are generated from thermal melt data. Researchers may 'visually' look at these curves in order to distinguish between different genotypes based on the differences in the appearance of their thermal melt curves, which represent differences in the dynamic profiles between the two genotypes. This visual inspection requires a high degree of user intervention in the identification of a particular genotype, since a researcher must match the signature curve generated from the dynamic profile of the unknown genotype to a known signature curve generated from a dynamic profile of a known genotype. Furthermore, subtle differences in the shape of the curve may not be detected by human inspection, and may lead to misidentification of the genotype.

Quantitative methods for analyzing the differences in thermal melt curves of an unknown genotype also exist. One quantitative method includes determining the temperature at the peak −dF/dT. This temperature is used as an estimate of the melting temperature of the nucleic acid $T_m$. This estimate of the $T_m$ of the nucleic acid may be used to classify the genotype of the nucleic acid by comparing its value to a distribution of melting temperatures for a known genotype. However, this method also presents potential shortcomings. Fore example, this method uses only one point of the entire thermal melt curve—the peak of the derivative—in order to determine the genotype. This possibly ignores the overall shape of the thermal melt curve, including the width of the curve and the height of the peak, which may be useful in determining the genotype of the sample. Further, two single nucleotide polymorphisms may have differences in melting temperature that are less than 0.5° C. apart. In this case, the resolution of the two thermal melt curves generated from data obtained in a microfluidic device may be too low in order to allow one to identify differences between the melting temperatures of the two genotypes, and thus between the genotypes.

In accordance with one aspect of the present invention, dynamic profiles generated by the above methods may be used to determine the identity of the genotype of a nucleic acid present in a biological sample, also referred to herein as an unknown genotype. In accordance with another aspect of the present invention, dynamic profiles generated by the above methods may be used to generate a training set to allow a machine to recognize a known genotype from within a class of known genotypes. In accordance with further aspects of the invention, the above method may be used to generate positive dynamic control profiles of control genotypes, which are used to account for and correct errors introduced by differences between instrumentation, initial conditions, ambient conditions, and other variations between experimental runs. Various embodiments of the invention will be described in greater detail below, along with reference to the figures.

In one aspect, the present invention provides a method of generating a training set to allow a machine to recognize a known genotype from within a class of known genotypes. In accordance with this aspect, a training set of a class of known genotypes is generated using the following steps: (a) grouping multiple dynamic profiles of the same genotype for each known genotype in a class of known genotypes; (b) normalizing each of the dynamic profiles; (c) averaging the normalized dynamic profiles of the same genotype to obtain an average normalized dynamic profile for each known genotype in the class of known genotypes; (d) correlating each dynamic profile with the average normalized dynamic profile of each known genotype in the class of known genotypes to generate a correlation vector for each dynamic profile; (e) transforming the correlation vectors such that when grouped together by genotype, each of the elements of the transformed vector are normally distributed; (f) compiling each transformed vector into a matrix of transformed vectors, such that there is one matrix for each known genotype in the class of known genotypes; (g) generating a mean transformed vector whose elements include an averaged transformed vector for each known genotype where the transformed vector is the average of each compiled matrix; and (h) calculating a covariance matrix for the known genotypes by calculating the covariance matrix of each of the compiled matrices.

In one embodiment, each dynamic profile comprises measurements of a signal representing a physical change of a nucleic acid containing the known genotype relative to an independent variable as described herein. As such, the dynamic profile is derived from the signal measurements representing the physical change of the nucleic acid. Multiple dynamic profiles for each known genotype of the class of known genotypes may be generated. In one embodiment, multiple dynamic profiles may be normalized so that they all have the same mean and standard deviation. In another embodiment, each correlation vector comprises correlation coefficients for the dynamic profile against each average normalized dynamic profile of each known genotype in the class of known genotypes. That is, each of the individual dynamic curves that make up the training set are correlated against each of the average normalized profiles to yield a correlation vector for each dynamic curve in the training set. In a further embodiment, the transformed vectors belonging to the same genotype are grouped together into a stacked matrix, and a mean vector (whereby each row of the matrix is averaged) and a covariance matrix of the stacked matrix is obtained. In one embodiment, this method produces a training set which comprises an average normalized dynamic profile, a mean transformed vector for each known genotype and a covariance matrix for each known genotype in the class of known genotypes.

In one embodiment, the method of generating the training set further comprises: (i) generating a positive control dynamic profile of a control genotype, wherein the positive control dynamic profile comprises measurements of a signal representing a physical change of a nucleic acid containing the control genotype relative to an independent variable taken concurrently with the measurements that comprise the dynamic profile of the unknown genotype; (ii) comparing the positive control dynamic profile to a standard positive control dynamic profile for the control genotype to determine a shift value for the independent variable; and (iii) shifting the independent variable of the dynamic profile of the positive control and the dynamic profiles of the known genotypes by the shift value. In a further embodiment, each dynamic profile comprises measurements of a signal representing a physical change of each nucleic acid containing each known genotype relative to an independent variable measured over a range selected to maximize the separation between dynamic profiles for different known genotypes within the class of known genotypes (between class scatter), while minimizing the separation between dynamic profiles of the same known genotype (within class scatter) such as described herein.

In another embodiment, the elements of the correlation vector are transformed to a new vector where each element belongs to a Gaussian distribution according to its genotype. In another embodiment, the method further includes the step of translating each correlation vector into a vector of n-coordinates, where n is less than or equal to the number of possible classes or genotypes. The number of classes or genotypes is equal to the number of different combinations of base pairs that are possible in the amplified DNA segment. The transformation vector can be constructed in such a way that when grouped by class, each of the elements are normally distributed. This allows the use of equations that describe multivariate Gaussian distributions to compute likelihoods and probabilities that a DNA sample belongs to each possible class. One such way to do this is to transform each correlation vector into spherical coordinates with the number of elements, n equaling the number of possible genotypes. This transforms the correlation vector where not all the elements are normally distributed to a vector where each of the elements is normally distributed when grouped by class. Alternatively, a transformation can be used where n is less than the number of classes, yielding a transformed vector with a lower number of elements than the correlation vector.

Figure 1B:
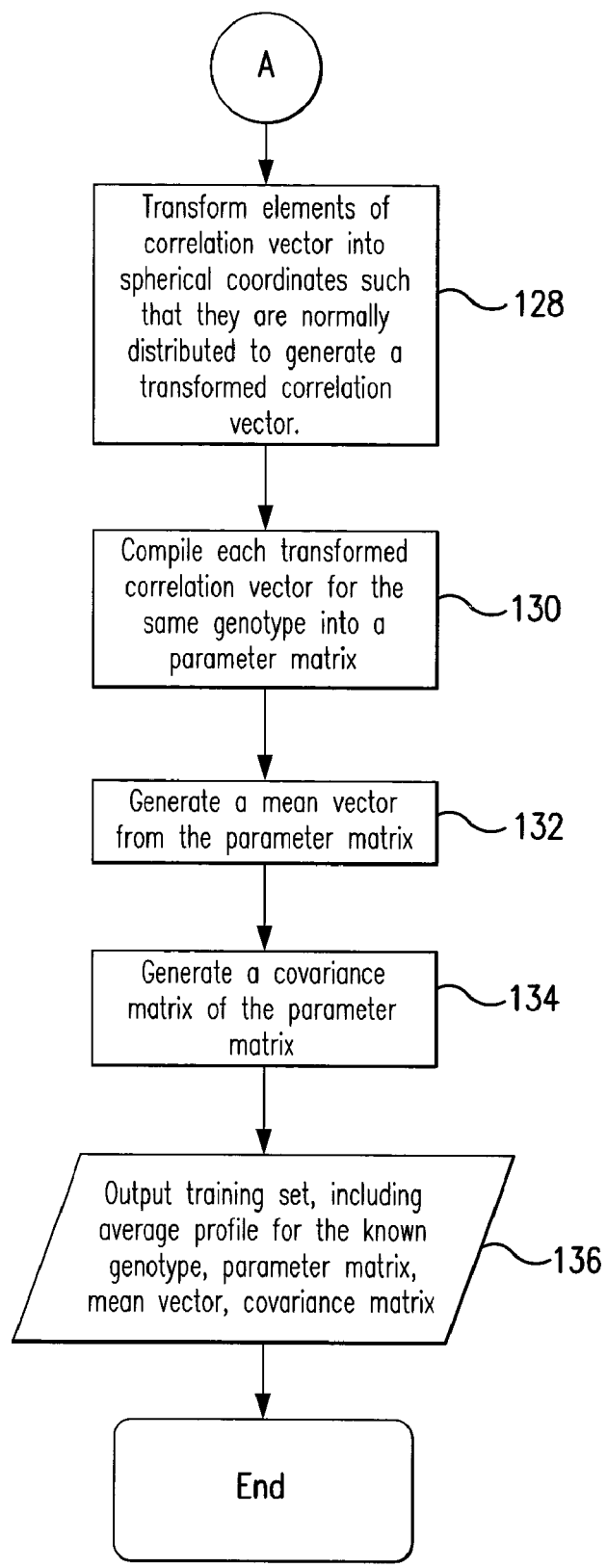

FIGS. 1A-1B illustrate a flow chart for method 100 for generating a training set in accordance with embodiments of the present invention. Step 102 in method 100 includes generating a plurality of dynamic profiles of a known genotype contained in a plurality of biological samples. The dynamic profiles may be generated from data generated in step 104. The data in step 104 may be generated by any of the methods described above for generating data for dynamic profiles or signature curves. The dynamic profiles each contain measurements of a signal, y(t), which represents a physical change of a nucleic acid containing the known genotype. These measurements of the signal are recorded relative to an independent variable, x(t). The parameter t may be any parameter over which both the independent variable and the signal are measured. In the case that the measurements in the dynamic profile is generated through thermal melting of a nucleic acid containing the known genotype with intercalating dyes, x(t) is the temperature T(t), and y(t) is the fluorescence, F(t), or the derivative of the fluorescence relative to temperature, $-dF/dT$. Alternatively, in the case that the dynamic profile is generated through voltammetry of a nucleic acid with a redox-active molecule, x(t) is the electric potential V(t) and y(t) is the electric current I(t). As a non-limiting example, a plot of several dynamic profiles for the three different genotypes in the Warfarin VKORC1 polymorphism is shown in the form of fluorescence versus temperature curves in FIG. 2 and as the derivative of the fluorescence relative to temperature in FIG. 3.

Step 106 of FIG. 1A includes generating an associated positive control dynamic profile of a control genotype. In one embodiment, the associated positive control dynamic profile is generated at the same time each of the plurality of dynamic profiles of the known genotype is generated. Each positive control dynamic profile of the positive control genotype is also comprised of measurements of the same signal relative to the same independent variable as the dynamic profile for the known genotype, though the measurements are taken from a positive control sample rather than the sample containing the known genotype. The measurements of the signal for the positive control genotype preferably are generated concurrently in step 104 with the measurements of the signal for the known genotype. This positive control dynamic profile may be compared to a standard reference dynamic profile for the control genotype. Alternatively, the independent variable of each of the positive control dynamic profiles may be shifted by a shift value $\Delta x$ such that the positive control dynamic profiles match up, and such that the mean of the shift values $\Delta x$ for all positive control dynamic profiles that are shifted is 0, as is shown in step 108. In step 110, the independent variable of the dynamic profile associated with a positive control dynamic profile is also shifted by the same shift value $\Delta x$ as the associated positive control dynamic profile. In order to shift an independent variable in a positive control dynamic profile or dynamic profile by the shift value $\Delta x$, $\Delta x$ is subtracted from or added to the independent variable in the positive control dynamic profile or dynamic profile.

Figure 4:
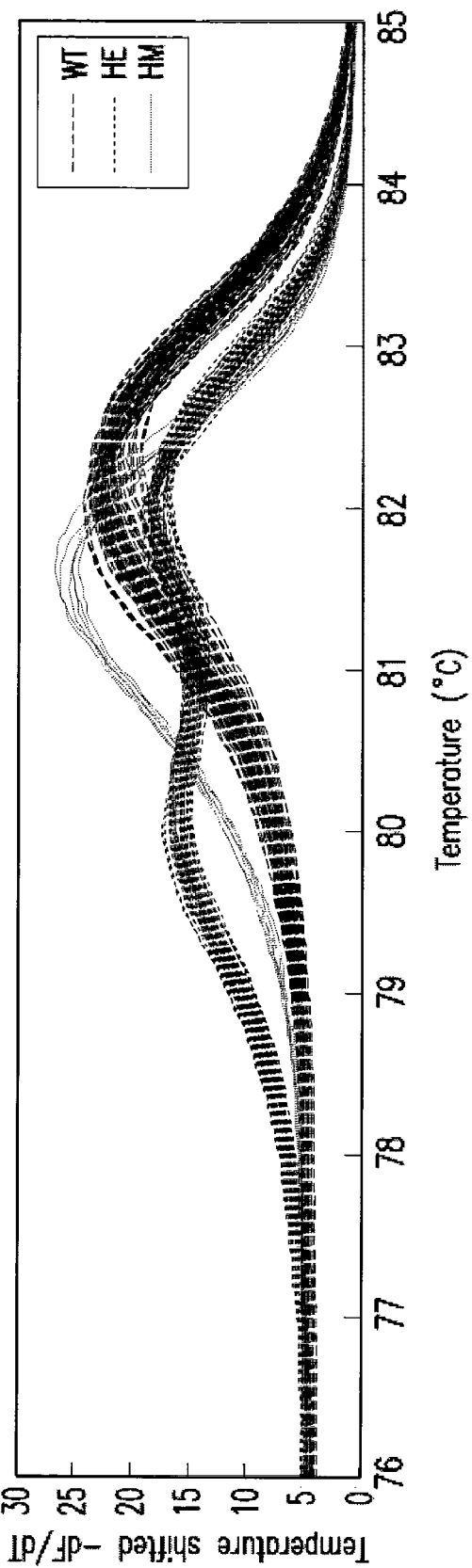
FIG. 4 illustrates the dynamic curves of FIG. 3 after having been horizontally shifted by a shift value determined by correlation of a positive control dynamic profile to a known dynamic profile for a positive control.

The dynamic profile may be normalized in order to have a predetermined standard deviation, as is shown in step 112. Optimally, the shifted dynamic profile is normalized. In some embodiments, the normalization procedure also normalizes the dynamic profile in order to have both a predetermined standard deviation and a predetermined average value. The predetermined average value may be zero, and the predetermined standard deviation may be 1. The normalized dynamic profile y'(x) may be calculated as follows:

$$y'(x) = \frac{y(x) - \mu(y(x))}{\sigma(y(x))}$$

wherein $\mu(y(x))$ is the average value of the dynamic profile and wherein $\sigma(y(x))$ is the standard deviation of the dynamic profile. As an example, several shifted dynamic profiles, in the form of –dF/dT versus temperature curves, are shown for the three different genotypes in the Warfarin VKORC1 polymorphism, as illustrated in FIG. 4.

Referring back to FIG. 1A, after shifting and normalizing all dynamic profiles associated with a known genotype for each genotype within the class of known genotypes, a set of normalized and shifted dynamic profiles 114 is generated. In some embodiments, these may be entered into data storage for use in other aspects of the invention.

The dynamic profile may be averaged with other dynamic profiles corresponding to the same known genotype in step 116. Averaging together several dynamic profiles corresponding to the same known genotype generates an averaged dynamic profile for a known genotype which contains average measurements of the signal representing the physical change of a nucleic acid containing the known genotype relative to the independent variable. In one embodiment of the invention, average dynamic profiles for each known genotype within a class of genotypes 118 are generated and stored for use in other aspects of the invention.

Figure 5:
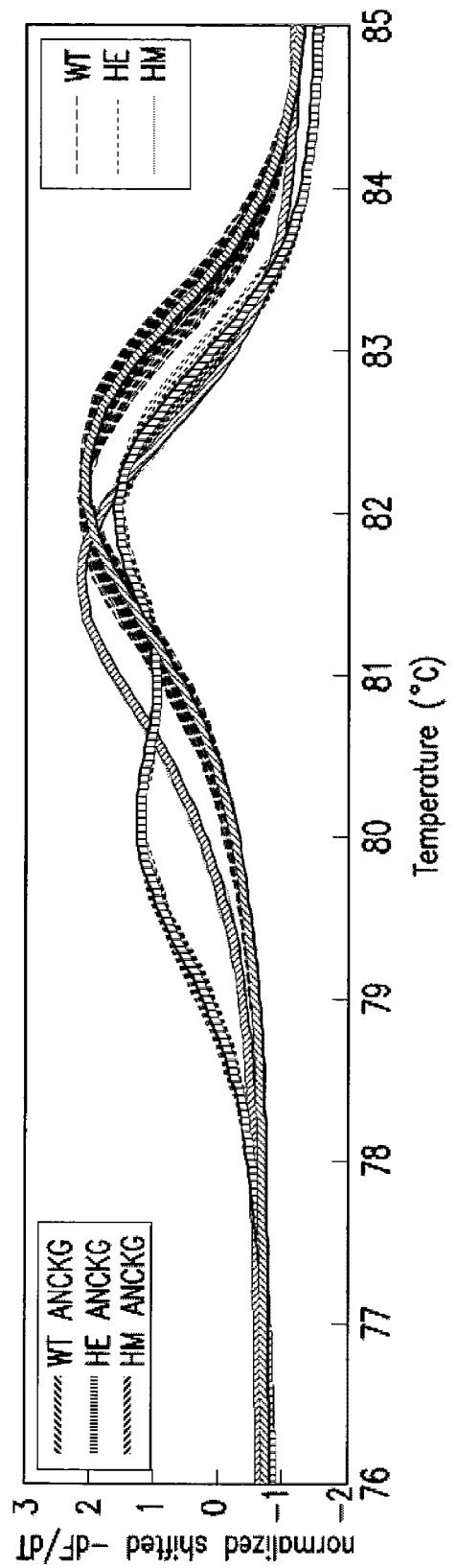
FIG. 5 illustrates the dynamic profiles of FIG. 4 after normalization to a predetermined standard deviation, and the average dynamic profile of each genotype within the Warfarin VKORC1 class according to one embodiment.

To generate an average dynamic profile for a known genotype, dynamic profiles for a known genotype may be averaged together. One way to average the dynamic profiles together is to calculate the mean value of the measurement of the signal for each different value of the independent variable across all of the dynamic profiles that are being averaged to make up the average profile for the known genotype. In some embodiments, some outlying data sets may be excluded at the discretion of an investigator. FIG. 5 shows the average profile for each known genotype in the Warfarin VKORC1 polymorphism class as the large, heavy lines among the thinner lines.

In addition, an average positive control dynamic profile may be generated in a similar manner by averaging together positive control dynamic profiles representing the same positive control genotype. Preferably, the dynamic profiles (or the positive control dynamic profiles) are shifted and normalized, as described above, prior to averaging them together to create an average normalized dynamic profile for the known genotype or the positive control genotype.

As used herein, the class of genotypes may include every genotype to which one would reasonably want to compare the unknown genotype. In some embodiments, the class of genotypes will be those genotypes associated with a particular polymorphism. For example, for the Warfarin VKORC1 polymorphism, there are three possible genotypes associated with the polymorphism: wild type (WT), heterozygous mutant (HE), and homozygous mutant (HM). The class of genotypes in this case would preferably include all three genotypes (WT, HE, and HM), though it may include fewer, and it may include additional genotypes beyond those associated with the Warfarin VKORC1 polymorphism as well. Likewise, for the coagulation factor MTHFR 677 single nucleotide polymorphism, there are three possible genotypes: wild-type (WT), heterozygote (HE), and homozygote (HM). In some embodiments, the class of genotypes may reasonably include the WT, HE, and HM genotypes.

Referring back to FIG. 1A, in step 120, each known dynamic profile for the control genotype is normalized to have a predetermined mean and standard deviation. In some embodiments, this normalization procedure is identical to the normalization procedure used for the dynamic profiles, discussed above. In step 122, the positive control dynamic profiles are averaged to generate a standard reference dynamic profile for the control genotype. The standard reference dynamic profile may be calculated in the same manner as the average dynamic profile for a known genotype is calculated. The standard reference dynamic profile may be output in step 124. In other embodiments, it may be stored in data storage for use in other aspects of the invention.

In step 126, each dynamic profile of a known genotype which has been used in calculating an average dynamic profile for the known genotype is correlated against the average dynamic profile for each known genotype in order to generate a correlation vector r for that dynamic profile:

$$r = \begin{bmatrix} r_1 \\ r_2 \\ \vdots \\ r_{Ng} \end{bmatrix}$$

wherein $r_1, r_2, \ldots, r_{Ng}$ are correlation values between the dynamic profile and each of the average dynamic profiles for each known genotype in the class of known genotypes. The correlation vector r may be an $[N_g \times 1]$ matrix, wherein $N_g$ is the number of genotypes that make up all of the possible mutations. Each element of the correlation vector may be a correlation coefficient of the dynamic profile against a different average dynamic profile of a known genotype.

The correlation coefficient need not be an actual correlation coefficient, but instead may be any value that represents the degree of difference between two sets of data, or two dynamic profiles. Such statistics include, but are not limited to, the sum squared error between the dynamic profile and the average dynamic profile, or the correlation coefficient between the average dynamic profile and the dynamic profile.

Figure 6:
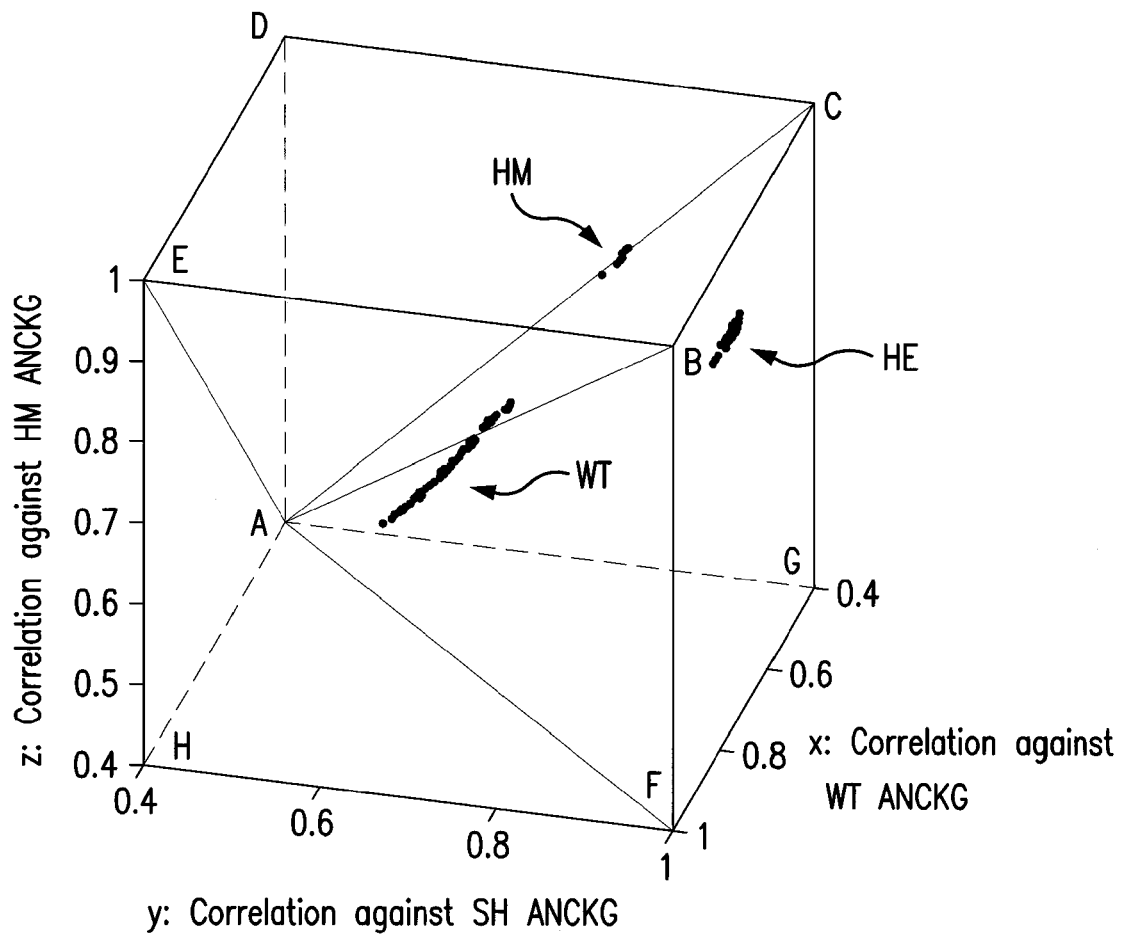
FIG. 6 illustrates a three-dimensional plot of correlation vectors for the Warfarin VKORC1 class in which the elements of the correlation vector are not normally distributed.
Figure 7A:
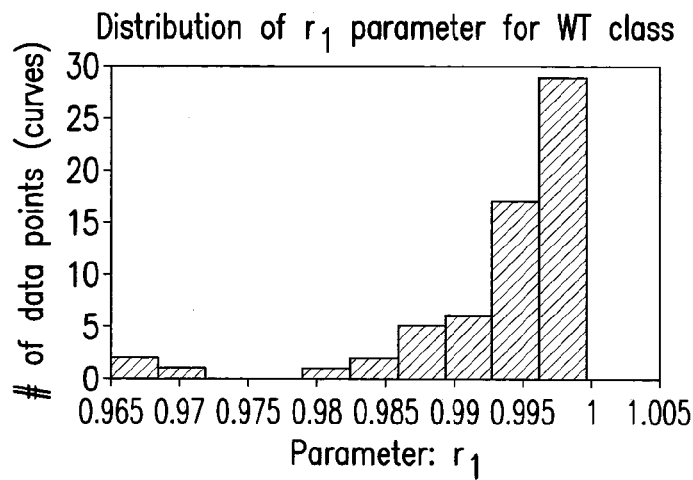
FIG. 7 illustrates plots of the correlation coefficient parameters of wild type dynamic profiles against the average dynamic profile for each genotype in the Warfarin VKORC1 class, in which the correlation coefficients are not normally distributed.
Figure 7B:
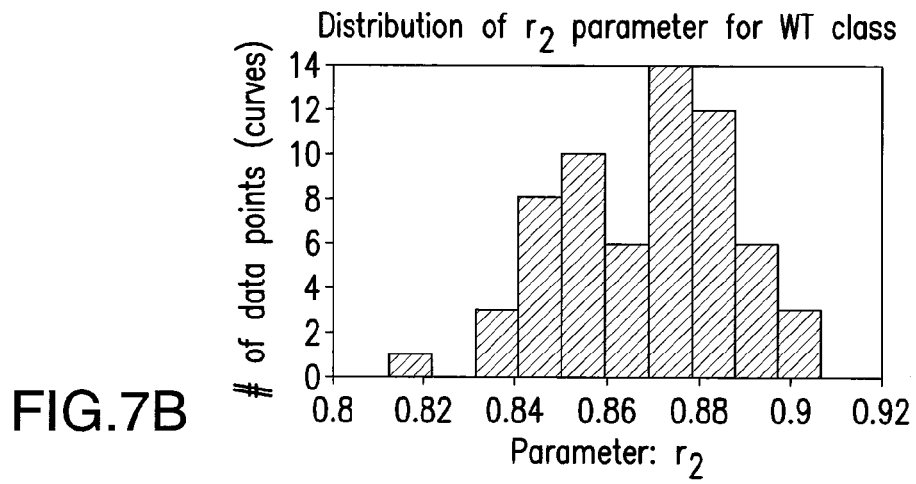
Figure 7C:
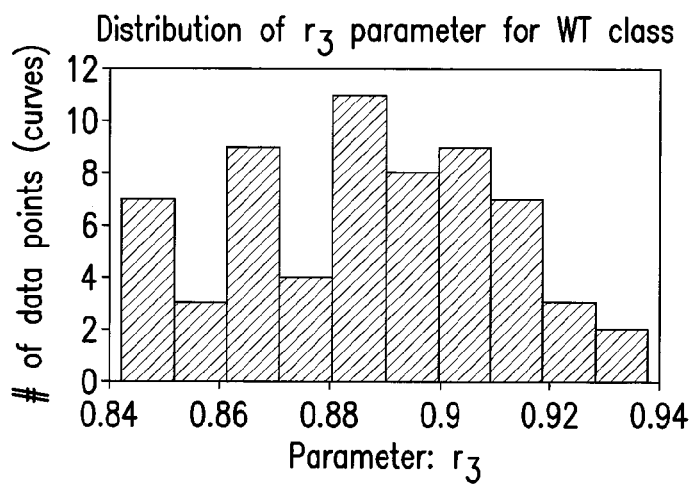

For a given genotype, the correlation coefficients of the various dynamic profiles against the average dynamic profile for a known genotype may not be normally distributed, in that they do not conform to a Gaussian distribution. FIG. 6 shows that, when arranged in 3-dimensional space, the correlation coefficients in the training set for the Warfarin VKORC1 polymorphism are not normally distributed, but instead rail at 1. Likewise, FIG. 7 shows the distribution of correlation coefficients of a group of dynamic profiles of the Warfarin VKORC1 WT genotype against the wild-type average dynamic profile, the heterozygous mutant average dynamic profile, and the homozygous mutant dynamic profile. Inspection of these graphs shows that the distribution of the correlation coefficients does not conform to a normal, or Gaussian, distribution. In order to force a normal distribution of the correlation coefficients, one may transform a correlation vector r of correlation coefficients into a correlation vector v by translating r into n-spherical coordinates, as is shown in step 128 in FIG. 1B. The correlation vector r may be translated into n-spherical coordinates as follows:

Correlation Vector:

$$r = \begin{bmatrix} r_1 \\ r_2 \\ \vdots \\ r_{N_g} \end{bmatrix}$$

Length:

$$l = \sqrt{\sum_{i=1}^{N_g}(r_i)^2}$$

jth angle where j goes from 1 to $N_g-1$:

$$a_j = \tan^{-1}\left(\frac{r_{j+1}}{\sqrt{\sum_{i=1}^{j}(r_i)^2}}\right)$$

Transformed vector:

$$v = \begin{bmatrix} l \\ a_1 \\ \vdots \\ a_j \end{bmatrix}$$

n-spherical coordinates include any coordinate system where, rather than defining a point in reference to an orthogonal Cartesian coordinate system, points are instead defined by their angles on an n-sphere and their radial distance from the origin. Examples of n-spherical coordinates include 1-spherical coordinates (commonly referred to as polar coordinates), or 2-spherical coordinates (commonly referred to simply as spherical coordinates). In one embodiment, transforming a correlation vector obtained from a sample that could be one of $N_g$ possible genotypes into n-spherical coordinates results in a transformed correlation vector with one length coordinate l and $N_g-1$ angular coordinates. As such, in this embodiment, the correlation vector may be transformed into n-spherical coordinates, where $n=N_g-1$.

Figure 8:
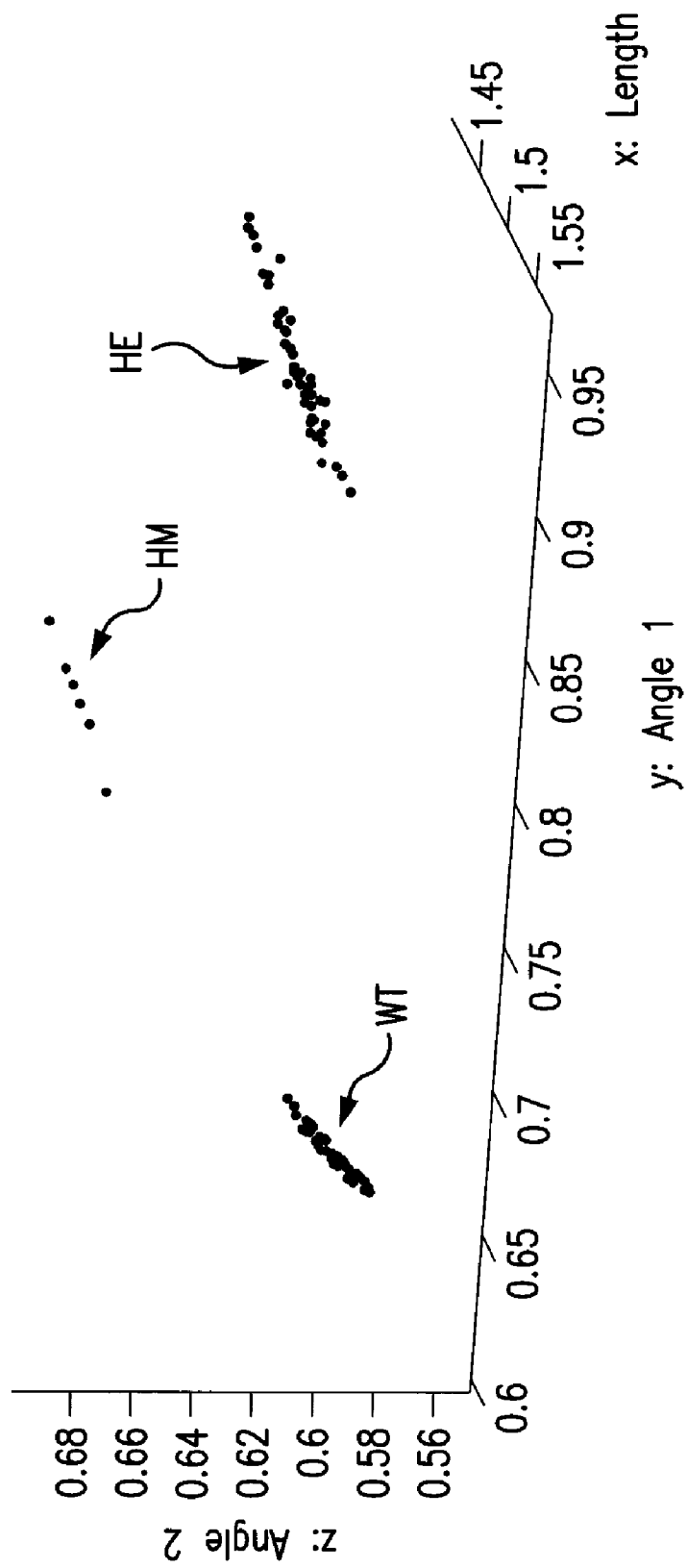
FIG. 8 illustrates a three-dimensional plot of correlation vectors for the Warfarin VKORC1 class in which the correlation vectors have been translated into spherical coordinates and are normally distributed.
Figure 9A:
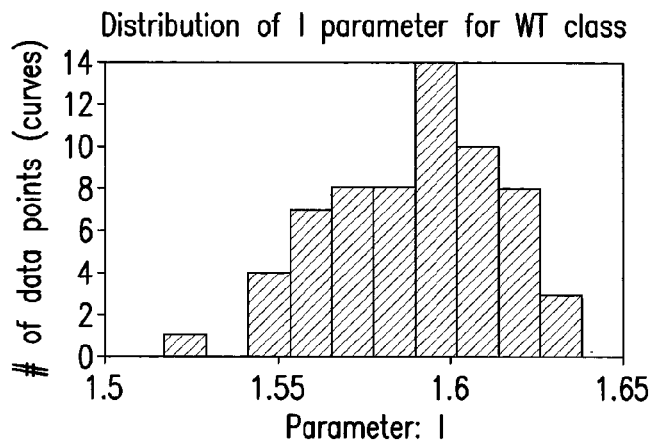
FIG. 9 illustrates plots of the correlation coefficient parameters of wild type dynamic profiles, after the correlation vectors have been translated to spherical coordinates, against the average dynamic profile for each genotype in the Warfarin VKORC1 class, in which the correlation coefficients are normally distributed.
Figure 9B:
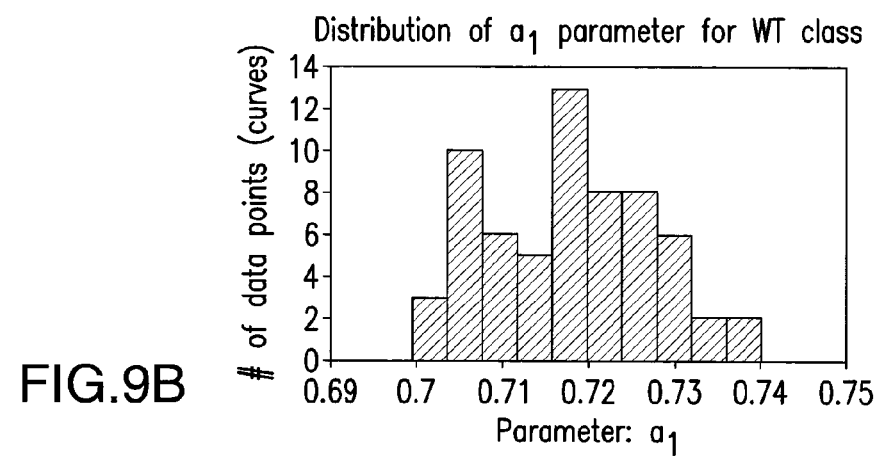
Figure 9C:
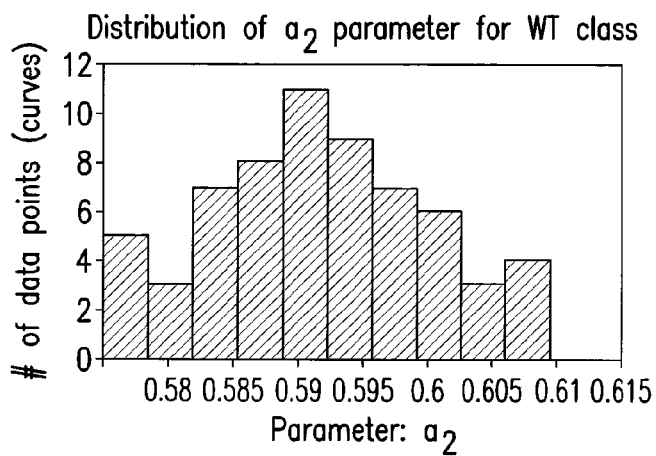

Transforming the correlation vector into n-spherical coordinates results in a set of correlation coefficients of the various dynamic profiles against an average dynamic profile for a known genotype that are normally distributed and do conform to a Gaussian distribution. FIG. 8 shows the transformed correlation coefficients for each of the three possible genotypes in the Warfarin VKORC1 class plotted on a three-dimensional grid, which shows that the correlation coefficients are roughly normally distributed. Likewise, FIG. 9 shows the distribution of correlation coefficients of the group of dynamic profiles of the Warfarin VKORC1 WT genotype against the wild-type average dynamic profile, the heterozygous mutant average dynamic profile, and the homozygous mutant average dynamic profile after the correlation vectors have been translated into spherical coordinates. Inspection of these graphs shows that the distribution of the correlation coefficients roughly conforms to a bell curve, i.e. a Gaussian distribution.

Referring back to FIG. 1B, in an aspect of the present invention, at least two correlation vectors for a known genotype may be compiled into a parameter matrix V for the known genotype, which is shown as step 130. Preferably, the transformed correlation vectors v are compiled into the parameter matrix for the known genotype. Preferably all correlation vectors for a known genotype are compiled into the parameter matrix for the known genotype, i.e. if $N_k$ dynamic profiles of a particular $k^{th}$ genotype are averaged together to generate the average dynamic profile for the particular genotype, and each dynamic profile has a correlation vector associated with it, then the parameter matrix V should include n correlation vectors. This may be expressed mathematically as follows:

$$V_k=[v_1 v_2 \ldots v_{N_j}],$$

where $V_k$ is the parameter matrix for the kth genotype in the class of genotypes, and $N_k$ is the number of dynamic profiles of the ith averaged together to generate the average dynamic profile for the $k^{th}$ genotype. In this embodiment, the dimensions of $V_k$ are $[N_g \times N_k]$. For this embodiment, each row is a parameter (e.g. l, $a_1$, $a_2$, etc.) and each column is a correlation vector for a dynamic profile of a known genotype with reference to the average normalized profile of each known genotype in the class of known genotypes.

In another aspect of the present invention, the parameter matrix V for a known genotype is used to generate a mean vector $\mu_k$ for a known genotype, as is shown in step 132 in FIG. 1B. The elements of the mean vector $\mu_k$ include the averages of each row of the parameter matrix $V_k$, i.e. each element of the mean vector is the average of the correlation values of each dynamic profile for a known genotype against an average dynamic profile for the same, or a different, known genotype within the class of genotypes. In step 134, the covariance matrix $C_k$ of the parameter matrix $V_k$ is calculated for a known genotype. The covariance matrix, $C_k$ is a square matrix whose elements are calculated as follows:

$$C_k(i,j) = \frac{\sum_{m=1}^{N_k}[(V_k(i,m)-\mu_k(i))(V_k(j,m)-\mu_k(j))]}{N_k-1}$$

where $N_k$ is the number of dynamic profiles compiled to make up the average profile of the $k^{th}$ genotype. In this embodiment, $C_k$ is an $[N_k \times N_k]$ matrix. In these aspects of the invention, the mean vector for a known genotype, the covariance matrix for the known genotype, and the average normalized profile for the known genotype are included in the training set 136 for the known genotype. The training set may additionally include a standard positive control dynamic profile 124 for the positive control genotype. The training set may be used to determine the probability and/or level of confidence that a biological sample containing an unknown genotype matches one of the possible known genotypes.

Figure 10:
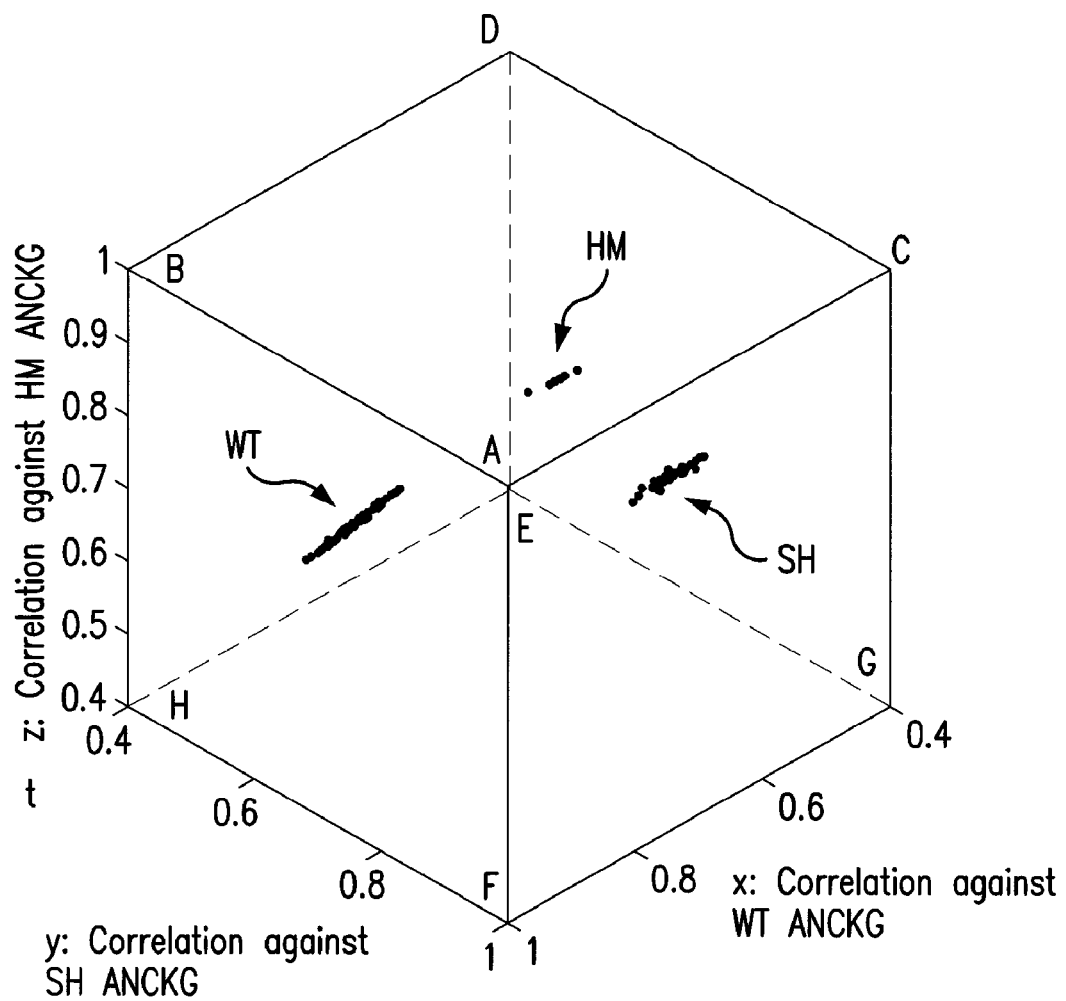
FIG. 10 illustrates a three-dimensional plot of correlation vectors for the Warfarin VKORC1 class projected on to the plane x+y+z=0, wherein the correlation vectors are normally distributed.

Transforming the correlation vector into n-spherical coordinates preserves the same number of parameters between the correlation vector r and the correlation vector v, resulting in a transformation that has no information loss. FIGS. 8 and 9 illustrate such a transformation. In an alternate embodiment, the correlation vector r may be transformed in order to normalize the distribution of the correlation values, while also reducing the number of dimensions in the correlation vector. FIG. 10 shows the distribution of correlation coefficients of a group of dynamic profiles of the Warfarin VKORC1 WT, HE, and HM genotypes against the wild-type average dynamic profile, the heterozygous mutant average dynamic profile, and the homozygous mutant dynamic profile after being projected on to the plane x+y+z=0. By reducing the number of dimensions to two, some information may be lost; however, the correlation coefficients become normally distributed. In one embodiment, this transformation can be accomplished by multiplying the correlation vector r by a transformation vector T. If the correlation vector is an $[N_g \times 1]$ matrix, where $N_g$ is the number of genotypes that make up all of the possible mutations, T may be an $[(N_g-h) \times N_g]$ matrix, where h is the reduction in the number of dimensions of the correlation vector.

A transformed correlation vector v may then be calculated by multiplying T by the correlation vector r:

$$v = T \cdot r$$

This results in a transformed correlation vector v that has the dimensions $[(N_g-h) \times 1]$. The parameter matrix $V_k$ containing such transformed correlation vectors is an $[(N_g-h) \times N_k]$ matrix, where $N_k$ is the total number of dynamic profiles for the kth genotype in the training set. The mean vector μ is an $[N_g-h \times 1]$ matrix, and the covariance matrix is an $[N_g-h \times N_g-h]$ matrix. Though this scenario may result in some information loss, T may be derived in such a way as to maximize the ratio of between-class scatter to within-class scatter in order to maximize the separation between different genotypes and minimize the separation between identical genotypes. For instance, to derive the graph in FIG. 10, the following transformation matrix T that projects each r onto the plane x+y+z=0 may be used:

$$T = \begin{bmatrix} -1 & 1 & 0 \\ -1/\sqrt{3} & -1/\sqrt{3} & 2/\sqrt{3} \end{bmatrix}$$

By transforming the correlation vectors into lower dimensions, it is possible to reduce the number of dynamic profiles needed to calculate an average profile of a known genotype that may be used to confidently identify an unknown genotype in a biological sample.

In another aspect, the present invention provides a method of determining the identity of the genotype of an unknown nucleic acid (also referred to as unknown genotype) present in a biological sample. In accordance with this aspect, an unknown genotype is determined by using the following steps: (a) generating a dynamic profile of an unknown genotype contained in the biological sample; (b) correlating the dynamic profile of the unknown genotype with an average dynamic profile of each known genotype in a class of known genotypes to generate a correlation vector; and (c) determining whether the correlation vector or a transformation thereof falls within an acceptable range to classify the unknown genotype as one of the known genotypes in the class of known genotypes, whereby the identity of the genotype of the nucleic acid in the biological sample is determined.

In one embodiment, the dynamic profile comprises measurements of a signal representing a physical change of a nucleic acid containing the unknown genotype relative to an independent variable. As such, the dynamic profile is derived from the signal measurements representing the physical change of the nucleic acid. In another embodiment, the average dynamic profile of each known genotype comprises average measurements of a signal representing the physical change of a nucleic acid containing the known genotype relative to the independent variable as described herein. In some embodiments, each dynamic profile is normalized to have a predetermined mean and standard deviation. In a further embodiment, the correlation vector comprises correlation coefficients between the dynamic profile of the unknown genotype and the average dynamic profile for each known genotype in the class of known genotypes. In some embodiments, the elements of the correlation vector are transformed to a vector with the same number of elements in which each element is normally distributed.

In one embodiment, the average dynamic profiles for the known genotypes are obtained from a training set, such as one prepared as described above. In another embodiment, the method is automated. In an additional embodiment, one or more steps are performed utilizing a computer. In a further embodiment, the method also comprises calculating a likelihood of the unknown genotype being a known genotype for each of the known genotypes in the class of known genotypes using class conditional densities of each known genotype. In this embodiment, the class conditional densities are calculated using mean transformed vectors and covariance matrices for each genotype. In one embodiment, the mean transformed vectors and covariance matrices are obtained from a matrix comprising grouped transformed vectors for each genotype obtained from the training set. In another embodiment, the method further comprises calculating the posterior probability that the biological sample contains each known genotype from the calculated likelihoods. In this embodiment, the determination step also involves determining whether the posterior probability that the biological sample contains a genotype falls within an acceptable threshold to determine if the unknown genotype is classified as one of the known genotypes. In some embodiments, the posterior probabilities that fall within the acceptable threshold are greater than a predefined threshold such as, for example, 95%.

In another embodiment, the determination step also comprises determining whether the correlation vector falls within an acceptable range to classify the unknown genotype, i.e., to determine if one of the known genotypes is identical to the unknown genotype present in the biological sample. In this embodiment, the acceptable range is an ellipsoid defined by the eigenvectors of the covariance matrix of the training set that contains a predefined threshold percentage (e.g. 95%) of the measurements of the signal relative to the independent variable within the dynamic profile. In another embodiment, the method further comprises translating each correlation vector into n-spherical coordinates, wherein n is one fewer than the number of genotypes that make up all of the possible mutations.

In a further embodiment, the method comprises: (i) generating a positive control dynamic profile of a control genotype, wherein the positive control dynamic profile comprises measurements of a signal representing a physical change of a nucleic acid containing the control genotype relative to an independent variable taken concurrently with the measurements that comprise the dynamic profile of the unknown genotype; (ii) comparing the positive control dynamic profile to a standard positive control dynamic profile for the control genotype to determine a shift value for the independent variable; and (iii) shifting the independent variable of the dynamic profile of the positive control and the dynamic profile of the unknown genotype by the shift value. The appropriate shift and/or scale value is the one that yields the maximum correlation between the positive control associated with the experiment and the standard positive control. This procedure can correct for sensitivity changes or shifts in the independent variable for different biological samples between experiments or within experiments. For example, slight shifts in temperature readings collected at different times (different experiments) or from different spatial locations in a chip or well based system can be corrected in this way to minimize the variance in the independent variable thus increasing the genotype classification accuracy.

In another embodiment, each dynamic profile comprises measurements of a signal representing a physical change of each nucleic acid containing each known genotype relative to an independent variable measured over a range selected to maximize the separation between dynamic profiles for different known genotypes within the class of known genotypes, while minimizing the separation between dynamic profiles of the same known genotype. This embodiment can be performed using the following steps: (a) calculating a within-class scatter matrix for the class of known genotypes using the mean vector and the parameter matrix for each genotype; (b) calculating a between-class scatter matrix for the class of known genotypes using the mean vector and the parameter matrix for each genotype; (c) determining a separation ratio that is the ratio of the determinant of the within-class scatter matrix to the determinant of the between-class scatter matrix; and (d) determining a separation-maximizing range for the independent variable, wherein the separation-maximizing range is selected to maximize the separation ratio. Each dynamic profile comprises measurements of a signal representing a physical change of each nucleic acid containing each known genotype relative to an independent variable measured over the separation-maximizing range. The determination step can be performed by determining the region of the dynamic curve defined by bounds on the independent variable (x-axis) that maximizes the separation between different genotypes that can be quantified using the separation ratio defined in (c). Quantification of the degree of separation between different genotypes is also important for scientists that design the assays that produce these dynamic curves. This separation quantifier will help them measure the degree of improvement of their new assay designs to maximize the accuracy of classifying the genotype.

In another embodiment, classifying the dynamic profile of the unknown genotype comprises: (1) correlating the dynamic profile of the unknown genotype with the average normalized profile of a each of the possible genotypes, that all together make up a correlation vector for the sample containing the unknown genotype; (2) mathematically transforming the correlation vector to another vector such that each element of the transformed vector is normally distributed (e.g., Gaussian distribution) according to its class or genotype; (3) calculating the likelihood of each possible genotype with respect to the biological sample of unknown genotype using the class conditional densities of each possible genotype obtained from the training set; and (4) calculating the posterior probability that the biological sample contains the known genotype from the likelihood values for each possible genotype obtained. In one embodiment, the average normalized profile for each possible genotype is obtained from a training set of multiple dynamic profiles derived from multiple nucleic acids of known genotype. In another embodiment, the dynamic profile is normalized to have a predetermined mean and standard deviation. In a further embodiment, the method of classifying the genotype in a biological sample further includes the steps of correcting for shift and scale changes of the sensed independent variable through the use of a positive control dynamic profile as described herein.

Figure 11A:
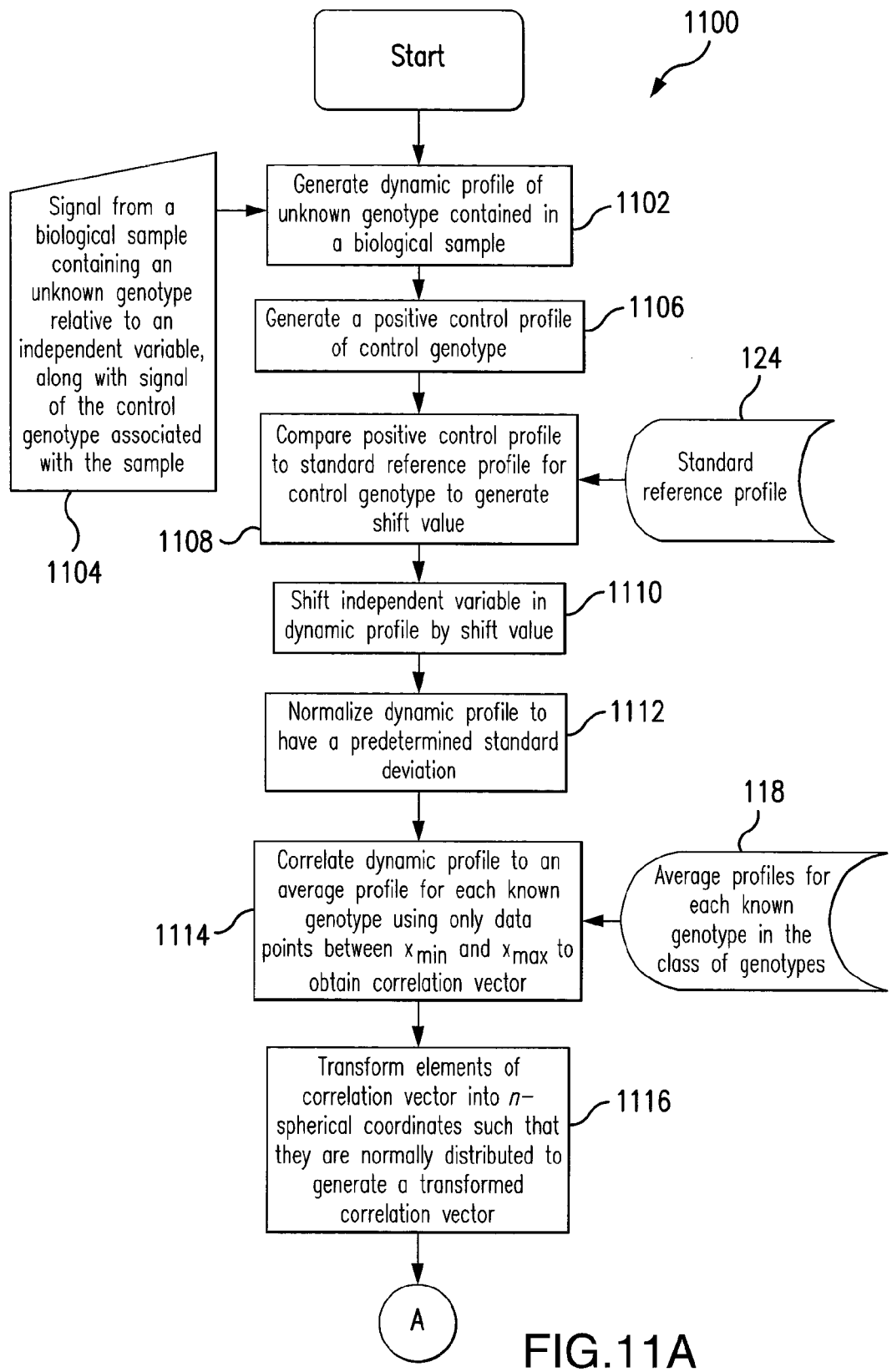
FIGS. 11A and 11B illustrate a flowchart showing a method of determining the identity of the genotype of a nucleic acid present in a biological sample in accordance with aspects of the present invention.
Figure 11B:
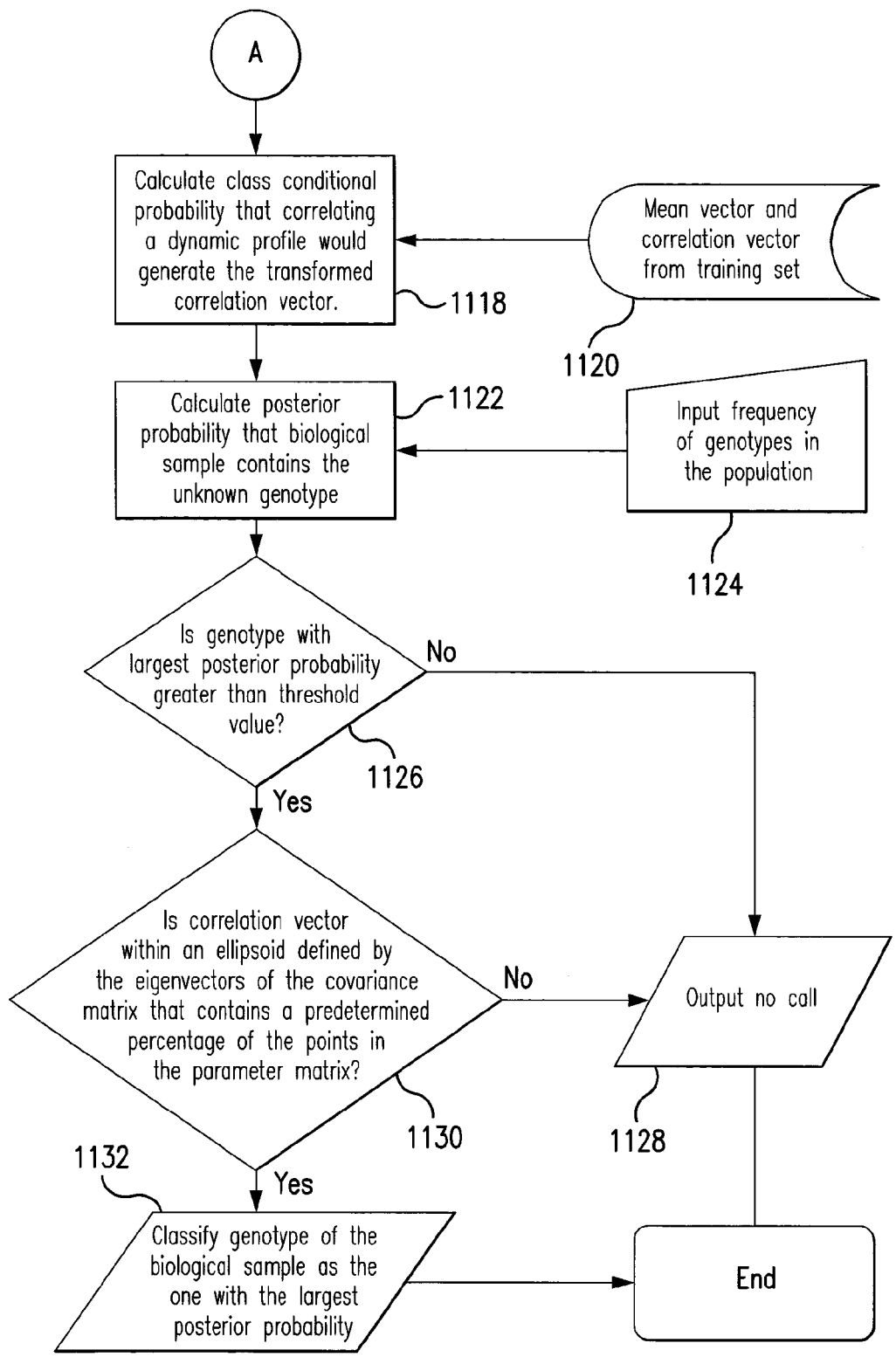

FIGS. 11A-11B illustrate a flow chart for method 1100 for determining the identity of the genotype of a nucleic acid present in a biological sample in accordance with embodiments the present invention. In step 1102, a dynamic profile y(x) of an unknown genotype contained in a biological sample is generated. The dynamic profile may be generated by any of the methods described herein. The dynamic profile contains measurements of a signal, y(t), which represents a physical change of a nucleic acid containing the known genotype. These measurements of the signal are recorded relative to an independent variable, x(t). These measurements are input into the method in step 1104. Depending on how the dynamic profile is generated, y(t) and x(t) may be different physical quantities. For example, in the case that the dynamic profile is generated through of thermal melting of a nucleic acid containing the known genotype with intercalating dyes, x(t) is the temperature T(t), and y(t) is the fluorescence, F(t), or the derivative of the fluorescence relative to temperature, $-dF/dT$. Alternatively, in the case that the dynamic profile is generated through voltammetry of a nucleic acid with a redox-active molecule, x(t) is the electric potential V(t) and y(t) is the electric current I(t).

In step 1104, an associated positive control dynamic profile of a control genotype is also generated at the same time the dynamic profile of the unknown genotype is generated. The associated positive control dynamic profile of the positive control genotype is also comprised of measurements of the same signal relative to the same independent variable as the dynamic profile, though the measurements are taken from a positive control sample rather than the sample containing the unknown genotype. In step 1106, a positive control dynamic profile is generated from the measurements of the positive control sample. In step 1108, the positive control dynamic profile is compared to a standard reference dynamic profile for the control genotype. This is done to generate a shift value $\Delta x$ for the independent variable, and this step is performed in the same manner as was done when determining the shift value $\Delta x$ when generating the training set. The standard reference dynamic profile of the positive control genotype may be the standard reference dynamic profile 124 generated when the training set was generated.

In order to generate the shift value $\Delta x$ as well as a scaling factor $\alpha$, the independent variable in a positive control profile $y_p(x)$ or dynamic profile is shifted by the shift value $\Delta x$ to generate a shifted profile $y_p'(x)$:

$$y_p'(x) = a * y_p(x - \Delta x)$$

Figure 12:
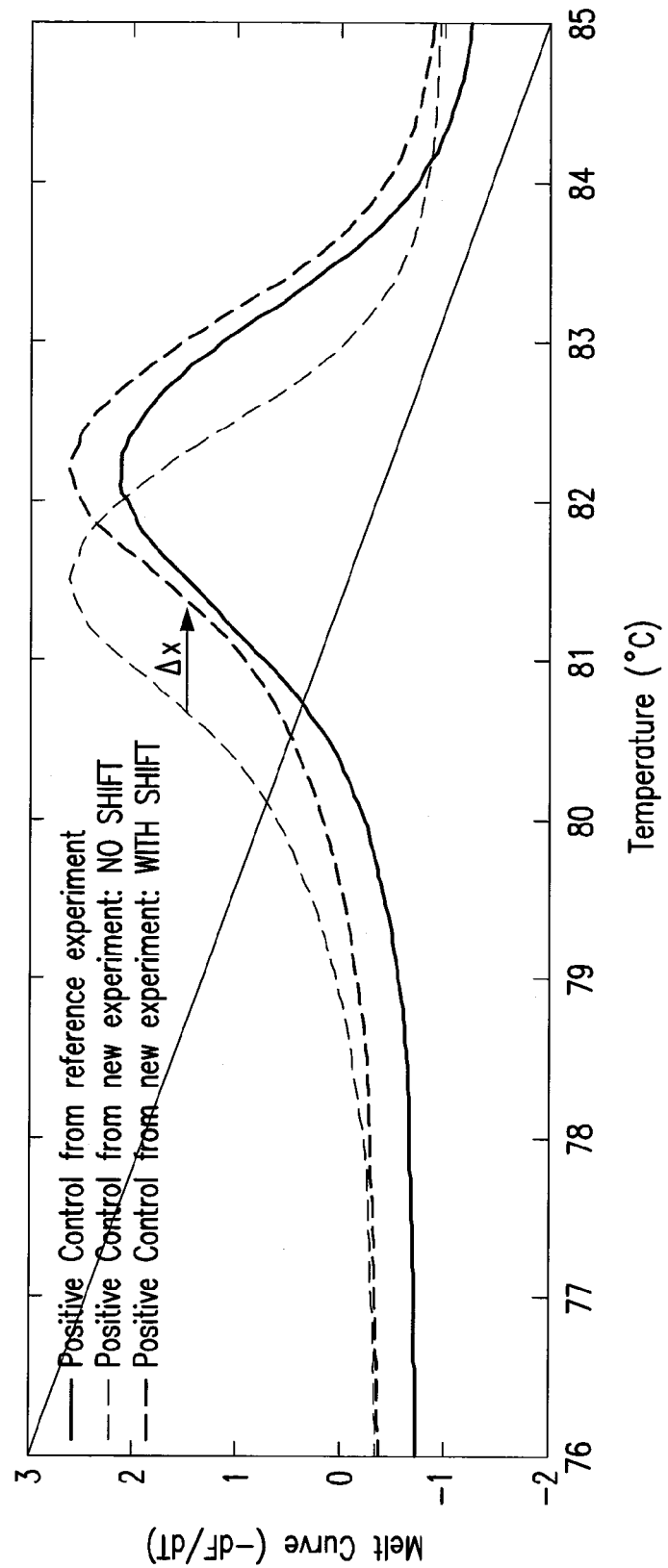
FIG. 12 illustrates a positive control for a control genotype profile being correlated to a known dynamic profile for the control genotype in order to determine a shift value for the independent variable.
Figure 13:
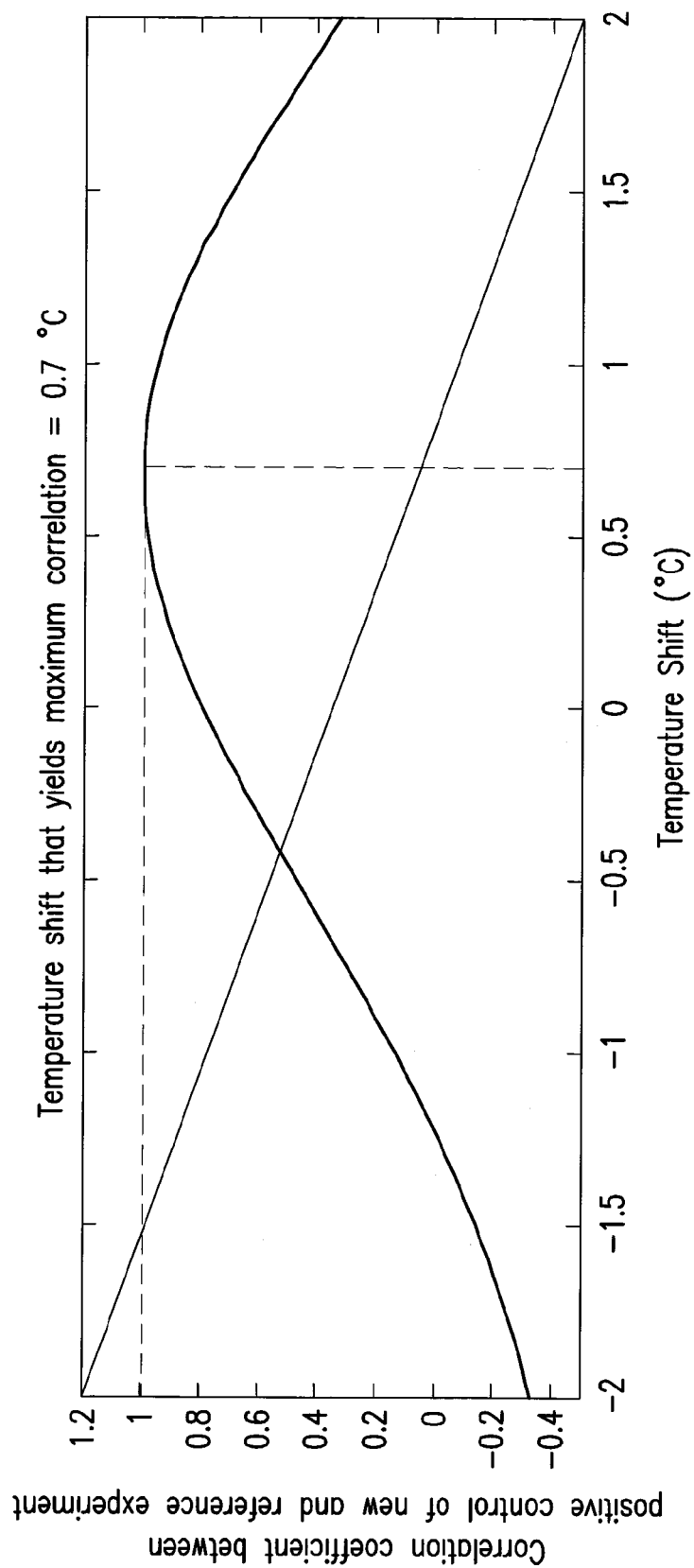
FIG. 13 illustrates a plot of the correlation coefficient of the positive control dynamic profile with the known dynamic profile for the control genotype versus the shift value.

Each of the shifted positive control profiles $y_p'(x)$ are then correlated to the known positive control profile $y_{rs}(x)$ to generate a correlation coefficient r. The correlation coefficient of a dynamic profile $y_1(x)$ against $y_2(x)$ may be calculated as follows:

$$r(y_1, y_2) = \frac{\sum_{i=1}^{n}[(y_1(i) - \mu_{y1})(y_2(i) - \mu_{y2})]}{(n-1)\sigma_{y1}\sigma_{y2}}$$

where n is the number of points that make up the dynamic profiles, $\mu_{y1}$ and $\mu_{y2}$ are the means of their profiles, and $\sigma_{y1}$ and $\sigma_{y2}$ are the respective standard deviations. Values of $\Delta x$ and a may be chosen such that the correlation coefficient r is maximized. FIG. 12 shows a positive control dynamic profile that is shifted in accordance with one aspect of the invention. The positive control dynamic profile, which is a $-dF/dT$ versus T curve, shifted to the right in order to generate the greatest degree of overlap with the known positive control dynamic profile, i.e., the positive control from the reference experiment. FIG. 13 is a plot of the correlation coefficient r versus the shift value $\Delta x$. As can be seen from the figure, the shift value that results in the maximum correlation coefficient, $\Delta x=0.7°$ C., is chosen, and the positive control profile is shifted by that amount.

In step 1110, the independent variable in the dynamic profile of the unknown genotype is shifted by the shift value $\Delta x$. The dynamic profile for the unknown genotype may also be scaled by the scaling factor $\alpha$. All dynamic profiles taken from the same experiment that is associated with a positive control may be shifted and scaled by the same amount, i.e. if more than one dynamic profile of an unknown genotype is generated in a single experiment, only one positive control dynamic profile need be generated, and only one shift value $\Delta x$ need be determined. This shifting and scaling procedure minimizes the variability in the independent variable from one experiment to the next, in order to make sure that results are consistent and reproducible.

In step 1112, the dynamic profile of the unknown genotype is normalized to have a predetermined standard deviation. It is also possible to normalize the dynamic profile of the unknown genotype to have a predetermined mean and a predetermined standard deviation. In one embodiment, the dynamic profile of the unknown genotype is normalized to have the same predetermined standard deviation and/or mean as the dynamic profiles of the known genotypes used to generate any training sets for the known genotypes to which the dynamic profile for the unknown genotype will be compared.

In step 1114, the dynamic profile is correlated to each one of the average dynamic profiles for each known genotype in the class of genotypes 118 in order to obtain correlation values for each known genotype. This correlation value may be the average sum squared error between the dynamic profile for the unknown genotype and the average dynamic profile for the known genotype, the correlation coefficient between the dynamic profile for the unknown genotype and the average dynamic profile for the known genotype, or a posterior probability that the unknown genotype is the genotype represented in an average dynamic profile for a known genotype. The correlation coefficient and the sum squared error may be calculated in a manner identical to that used for calculating correlation coefficients and sum squared error in the method of generating the training set.

Mathematically, the correlation coefficient of the dynamic profile containing the unknown genotype against the average dynamic profile for the known genotype that generates the largest value should indicate that the unknown genotype is that known genotype. Likewise, the average dynamic profile for a known genotype that generates the lowest average sum squared error between the dynamic profile for the unknown genotype and the average dynamic profile for the known genotype should indicate that the unknown genotype is that known genotype.

Statistically, however, the largest correlation coefficient or the lowest sum-squared error may not necessarily correspond to the correct genotype. In one embodiment, in order to statistically calculate the probability or confidence that a biological sample containing an unknown genotype contains a particular known genotype, the posterior probability that the unknown genotype is the known genotype is calculated. First, a correlation vector r is calculated. In one embodiment, the correlation vector r is a vector with dimensions $[N_g \times 1]$ that includes in its elements a correlation coefficient between the dynamic profile of the unknown genotype and each of the average dynamic profiles of a known genotype within the class of genotypes 118. Alternatively, the correlation coefficients may be the average sum squared error between the dynamic profile of the unknown genotype and the average dynamic profile of each known genotype within the class of genotypes. In step 1116, the elements of the correlation vector r are translated into a correlation vector v by translating the elements of the correlation vector r into n-spherical coordinates, which causes the elements of the correlation vector to fall within a normal (or Gaussian) distribution.

In step 1118, the class conditional probability $p(g_i|v)$ that correlating a dynamic profile of a first known genotype to an average normalized dynamic profile for a first known genotype would generate the transformed correlation vector v is calculated. The class conditional probability that a known genotype $g_i$ would generate the correlation vector v may be calculated from the mean vector $\mu_i$ and the covariance matrix $C_i$ included in a training set 1120 for that known genotype by using the following formula:

$$p(v|g_i) = \exp\left(-\frac{1}{2}(v-\mu_i)^T(C_i)^{-1}(v-\mu_i) - \frac{N_g}{2}\log(2\pi) - \frac{1}{2}\log(|C_i|)\right)$$

wherein $|C_i|$ is the determinant of the covariance matrix, and $N_g$ is the number of genotypes that make up all of the possible mutations.

If the occurrence of each possible genotype in the class of genotypes was equally likely in the population, then the unknown genotype could be identified as the genotype with the largest class-conditional probability with a great degree of confidence. However, in one embodiment, the posterior probability that the unknown genotype corresponds to a known genotype is calculated, as is illustrated in step 1122 of FIG. 11B. The user may input the frequency of the known genotype $P(g_i)$ into the algorithm, as illustrated in step 1124, and Bayes's Theorem may be used to calculate the posterior probability $p(v|g_i)$ that the unknown sample is the known genotype:

$$p(g_i|v) = \frac{P(g_i) \cdot p(v|g_i)}{\sum_{i=1}^{N_g}(P(g_i) \cdot p(v|g_i))}$$

In one embodiment of the present invention, a call is made as to when the calculated posterior probability for a genotype is greater than a predetermined threshold value, as shown in step 1126. In one embodiment of the present invention, the threshold value is greater than or equal to 95%. If none of the posterior probabilities is greater than the threshold value, no call is made, and this result is output in step 1128. If the posterior probability is greater than the threshold value, then the unknown genotype may be classified as the known genotype. In some embodiments, if the correlation vector does not fall within an acceptable range, then the unknown genotype may not be classified as the known genotype, even if the posterior probability that the unknown genotype is the known genotype is greater than the predetermined threshold, and thus no call is output, as illustrated in step 1128.

To determine the acceptable range, the eigenvectors and the eigenvalues of the covariance matrix of the known genotype are calculated. The eigenvectors of the covariance matrix define an n-ellipsoid (where n is the number of elements in the transformed correlation vector v) that should contain a predetermined percentage of the transformed correlation vectors $v_i$ generated from each dynamic profile for the known genotype in the training set for the known genotype. In one embodiment, the predetermined percentage is 98%. If the correlation vector v is determined to fall within the acceptable range in step 1130, then the unknown genotype is classified as the known genotype with the largest posterior probability, in step 1132.

Figure 14:
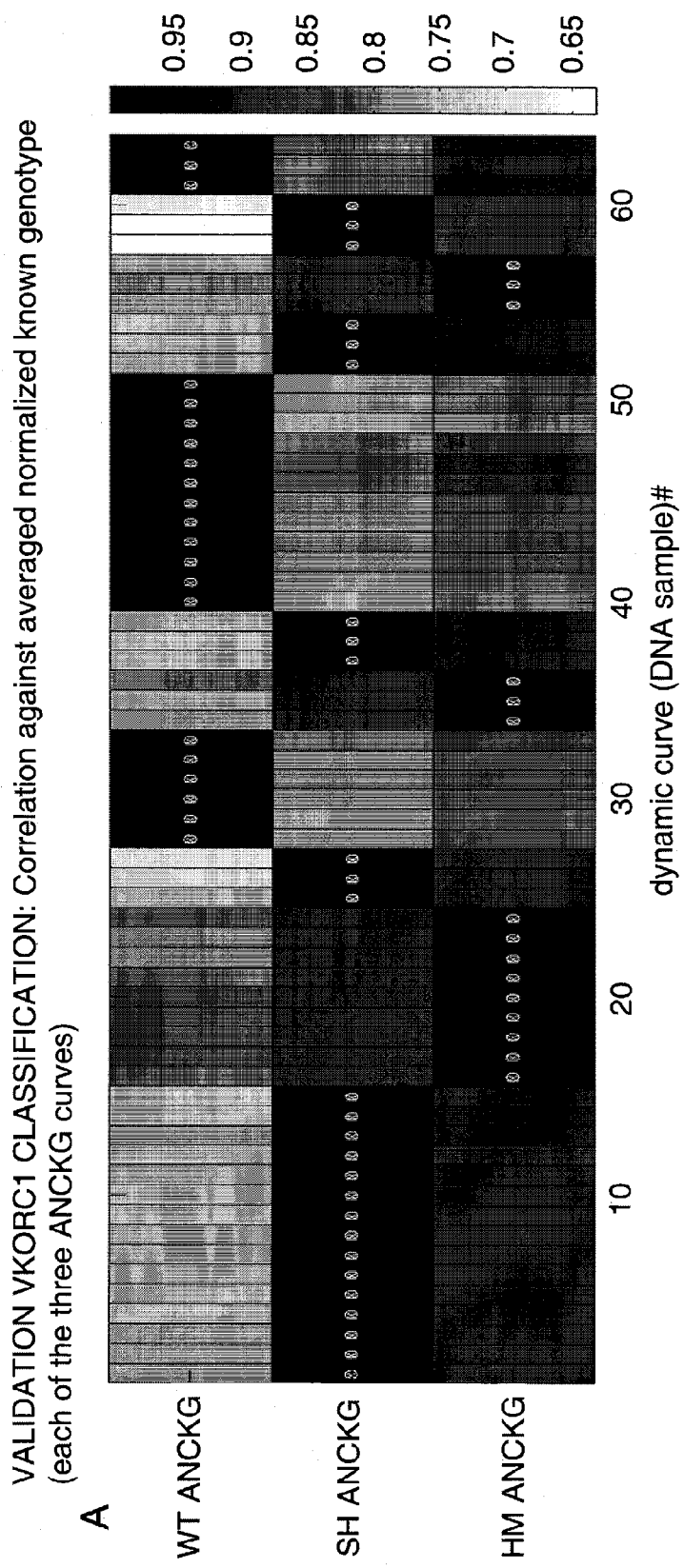
FIG. 14 illustrates a gray scale color map of the correlation coefficients generated by correlating different dynamic profiles of an unknown genotype to the average dynamic profile of a known genotype for each known genotype in the Warfarin VKORC1 class.
Figure 15:
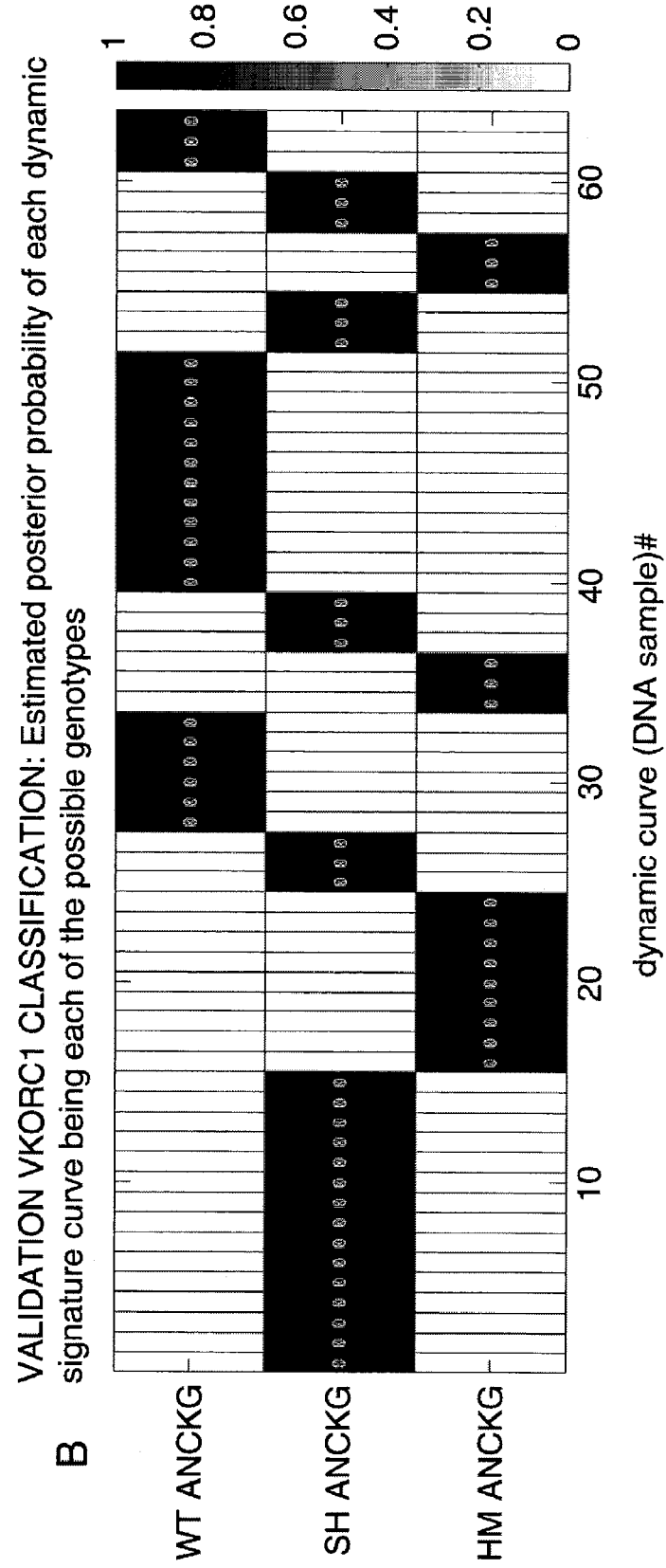
FIG. 15 illustrates a gray scale color map of the posterior probability that each of the different dynamic profiles of an unknown genotype represents a dynamic profile of each known genotype in the Warfarin VKORC1 class.

As stated above, the correlation coefficient of the dynamic profile containing the unknown genotype against the average dynamic profile for the known genotype that generates the largest correlation coefficient may indicate that the unknown genotype is that known genotype. However, to be more certain, it is preferred in some embodiments to calculate the posterior probability that the sample contains a particular known genotype. FIG. 14 shows the correlation coefficients of 63 different dynamic profiles obtained from different samples against the WT average dynamic profile, the HE average dynamic profile, and the HM average dynamic profile. Darker areas represent larger correlation coefficients, and lighter areas represent smaller correlation coefficients. FIG. 15, meanwhile, shows the corresponding posterior probabilities, with darker areas representing larger posterior probabilities and lighter areas represent smaller posterior probabilities. In both figures, the circles represent the actual genotype, while the exes represent the greatest correlation coefficient in FIG. 16 and the greatest posterior probability in FIG. 15. In FIG. 14, it may be seen that the dynamic profile shows significant correlation against the average dynamic profiles for all three genotypes. However, in FIG. 15, the determination of the genotype is nearly 100% certain when the posterior probabilities are used.

In a further embodiment of the present invention, dynamic profiles are obtained within a particular separation-maximizing range of independent variable values. In one embodiment, the separation maximizing range is determined by quantifying the separation between the different genotypes within the class of genotypes. This separation may be quantified as the ratio between the between-class scatter to the within-class scatter. In order to quantify this separation, the parameter matrix $V_k$ is obtained from each of the k training sets for each of the $N_g$ genotypes from within the class of genotypes. One may also calculate the between-class scatter matrix and the within-class scatter matrix for the class of genotypes. The within-class scatter matrix for the class of genotypes may be calculated using the following formula:

$$\tilde{S}_W = \sum_{k=1}^{N_g} \sum_{v \in V_k} (v - \mu_k)(v - \mu_k)^T$$

while the between-class scatter matrix may be calculated using the following formula:

$$\tilde{S}_B = \sum_{k=1}^{N_g} N_i(\mu_k - \mu)(\mu_k - \mu)^T$$

wherein $\mu_i$ is the mean vector for the ith training set and wherein $\mu$ is the mean parameter set of all dynamic profiles that make up all of the training sets for the class of genotypes. A separation ratio q may then be determined by calculating the ratio of the determinant of the between-class scatter matrix to the within-class scatter matrix:

$$q = \frac{|\tilde{S}_B|}{|\tilde{S}_W|}$$

The separation-maximizing range is chosen such that the maximum value of the separation ratio q is obtained. q is maximized for a particular class of genotypes by, first, obtaining training sets from dynamic profiles for each known genotype in the class of known genotypes where only measurements of the signal relative to the independent variable in the range between a minimum value $x_{min}$ and a maximum value $x_{max}$ are included. The separation ratio q is then calculated and recorded. Third, the first and second steps are iterated for a wide variety of different $x_{min}$ and $x_{max}$. The value of $x_{min}$ and $x_{max}$ that results in the maximum value of q is then selected as the separation-maximizing range of independent variable values. Measurements of the signal relative to independent variable values within the separation-maximizing range are included in dynamic profiles of genotypes within that class of genotypes, as well as dynamic profiles of unknown genotypes estimated to be one of the genotypes within that class of genotypes. In one embodiment, by iteratively calculating q for different values of $x_{min}$ and $x_{max}$, one may determine values of $x_{min}$ and $x_{max}$ for which q is maximized, and thus determine the separation maximizing range.

Figure 16:
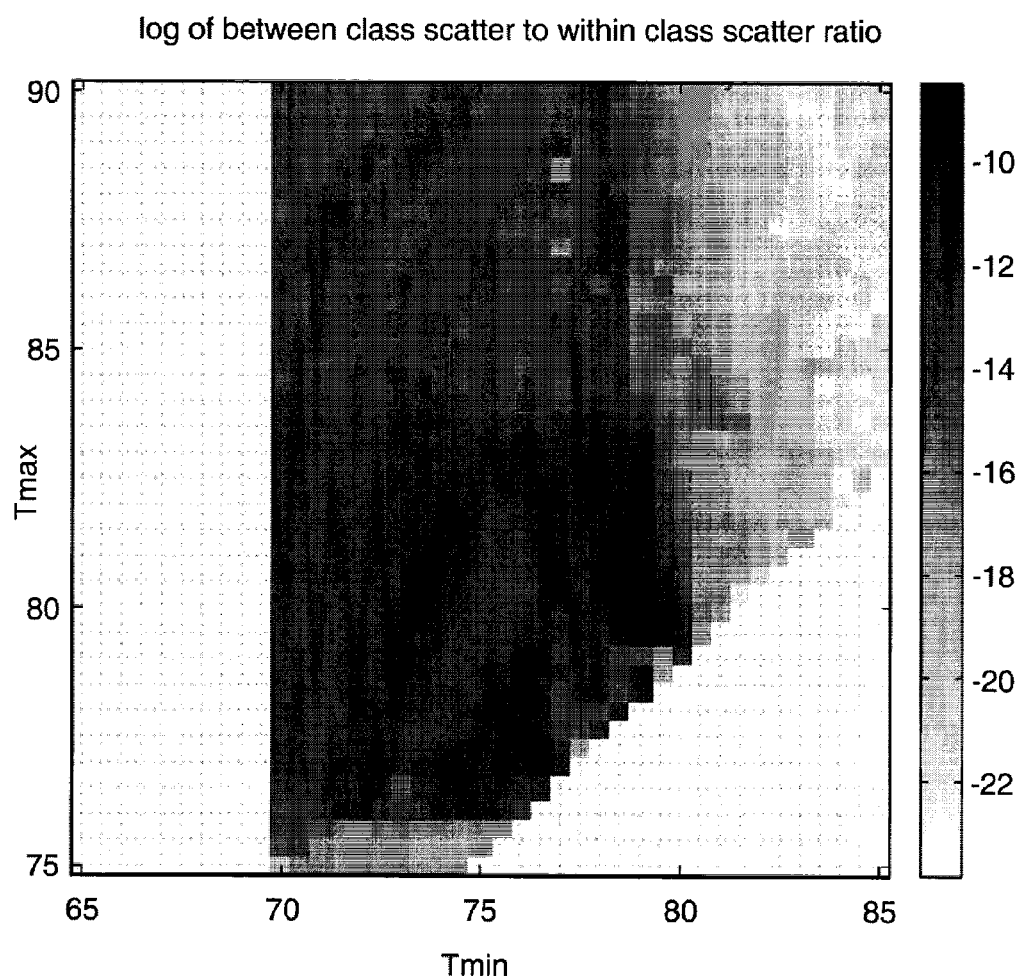
FIG. 16 illustrates a gray scale color map of the ratio of the between class scatter and within class scatter used to choose a temperature range selected to maximize the separation between the dynamic profile for different known genotypes, while minimizing the separation between dynamic profiles of the same genotype class.

FIG. 16 shows a calculation for dynamic profiles which are thermal melt curves in the Warfarin VKORC1 polymorphism class. Each square represents a temperature window between $T_{min}$ and $T_{max}$ in °C. The darkness of the shading of the square is proportional to the logarithm of q. As can be seen from the diagram, the separation of the curves is generally maximized where $T_{min}$ is between 70° and 80° C. and where $T_{max}$ is between 80° and 85° C. The optimal temperature window, from this figure, is between 79° and 82° C.

Figures 1, 17A:
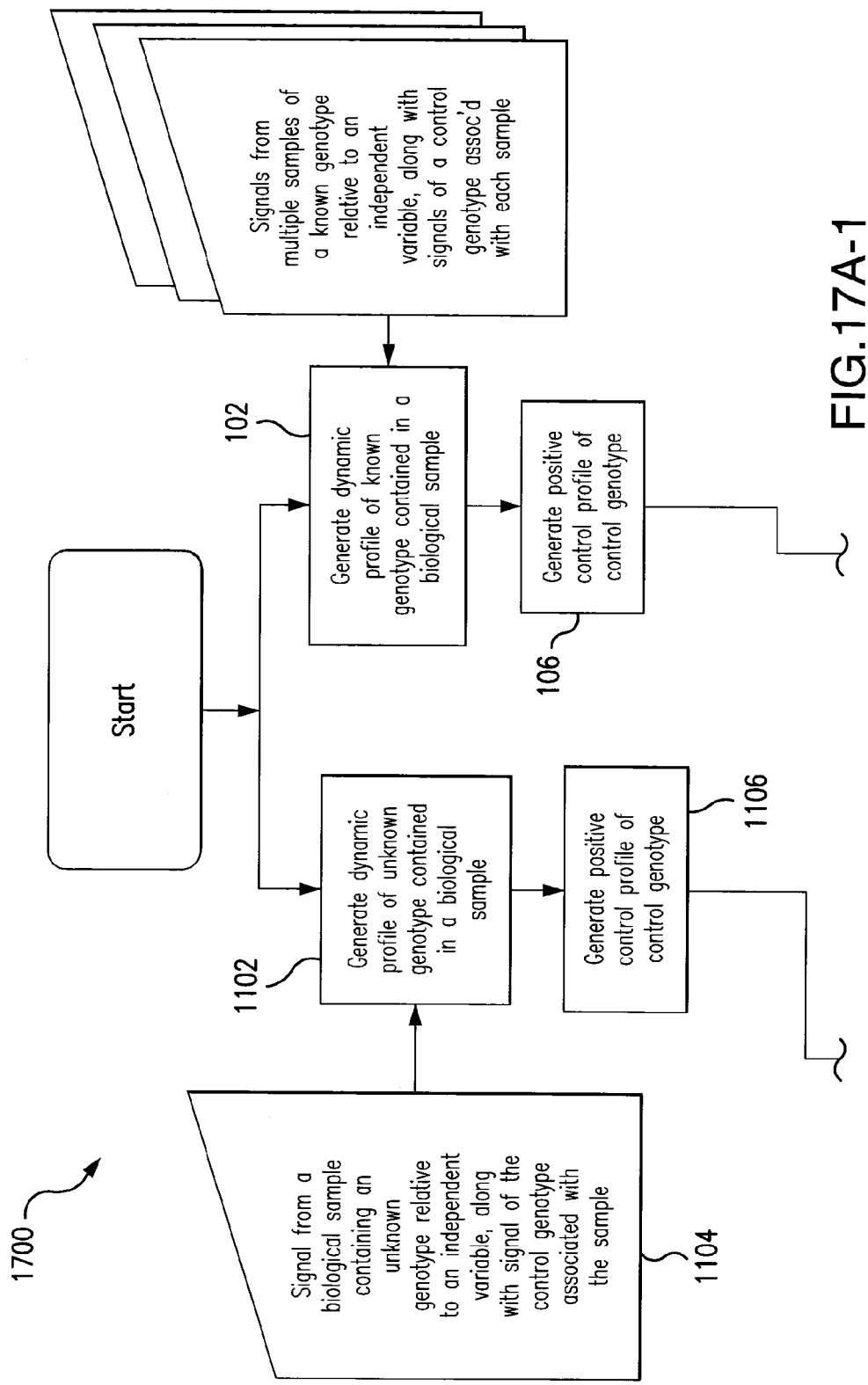
FIGS. 17A-C illustrate a flowchart showing a method of determining the identity of the genotype of a nucleic acid present in a biological sample using a training set in accordance with aspects of the present invention.
Figures 2, 17A:
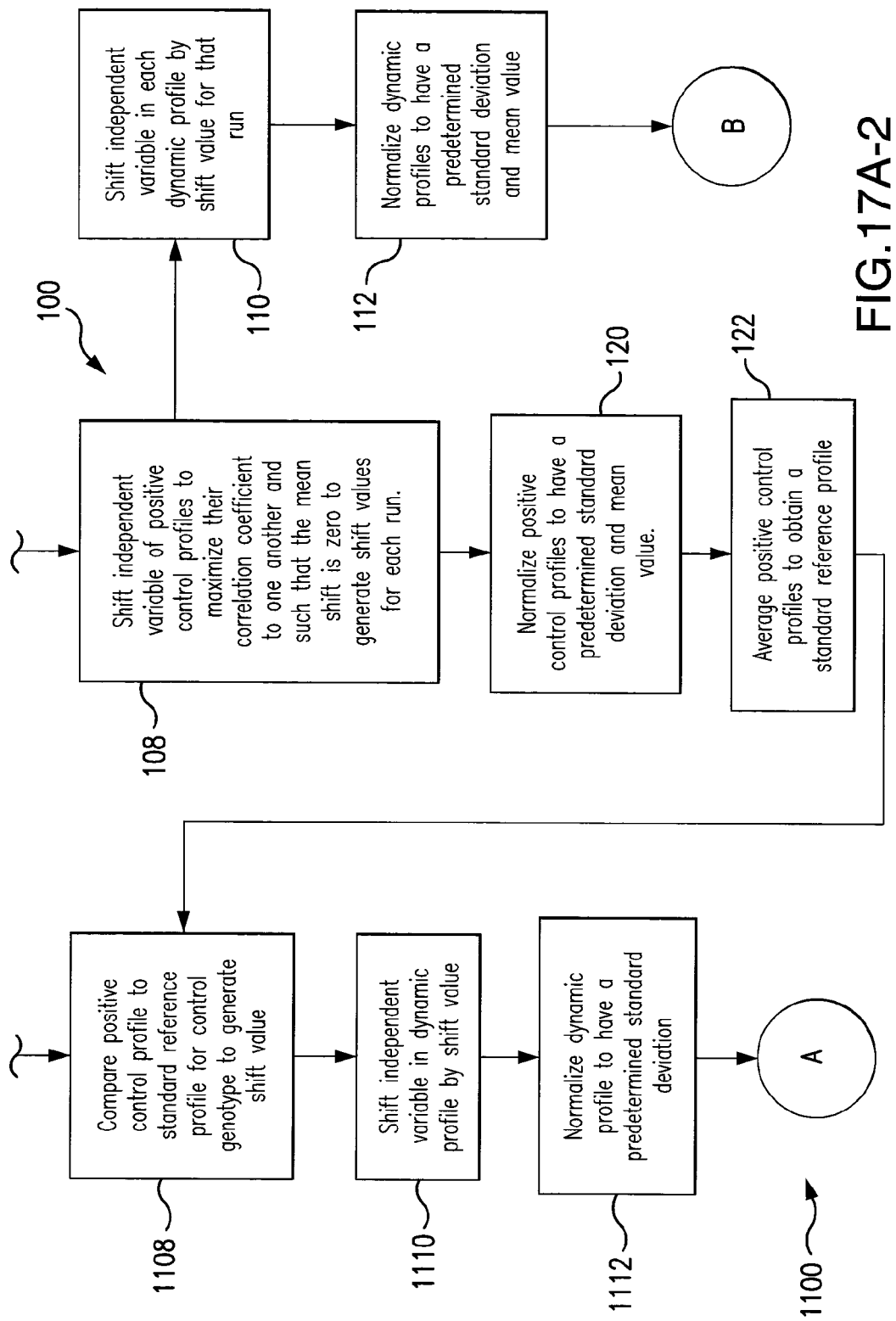
Figure 17B:
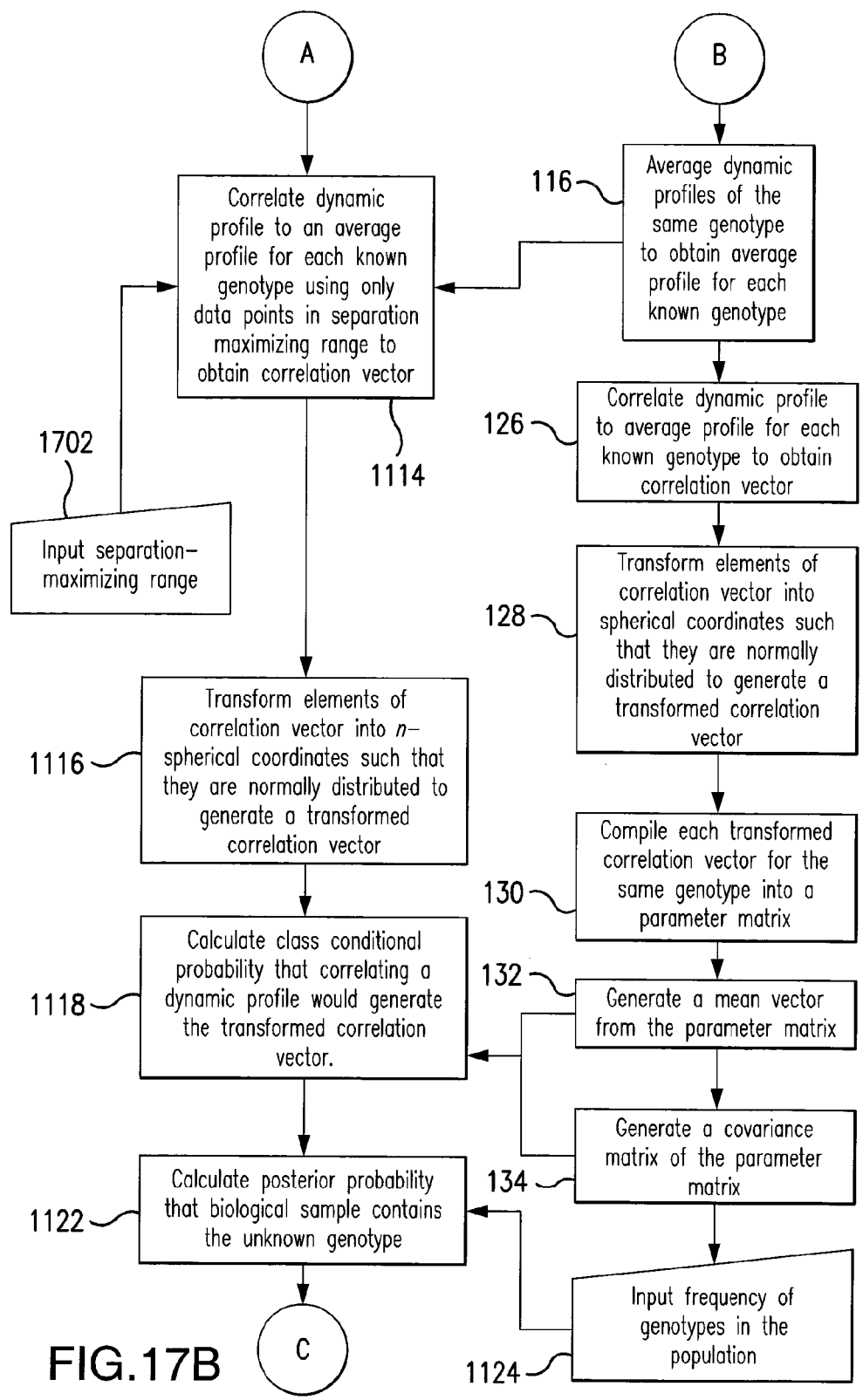
Figure 17C:
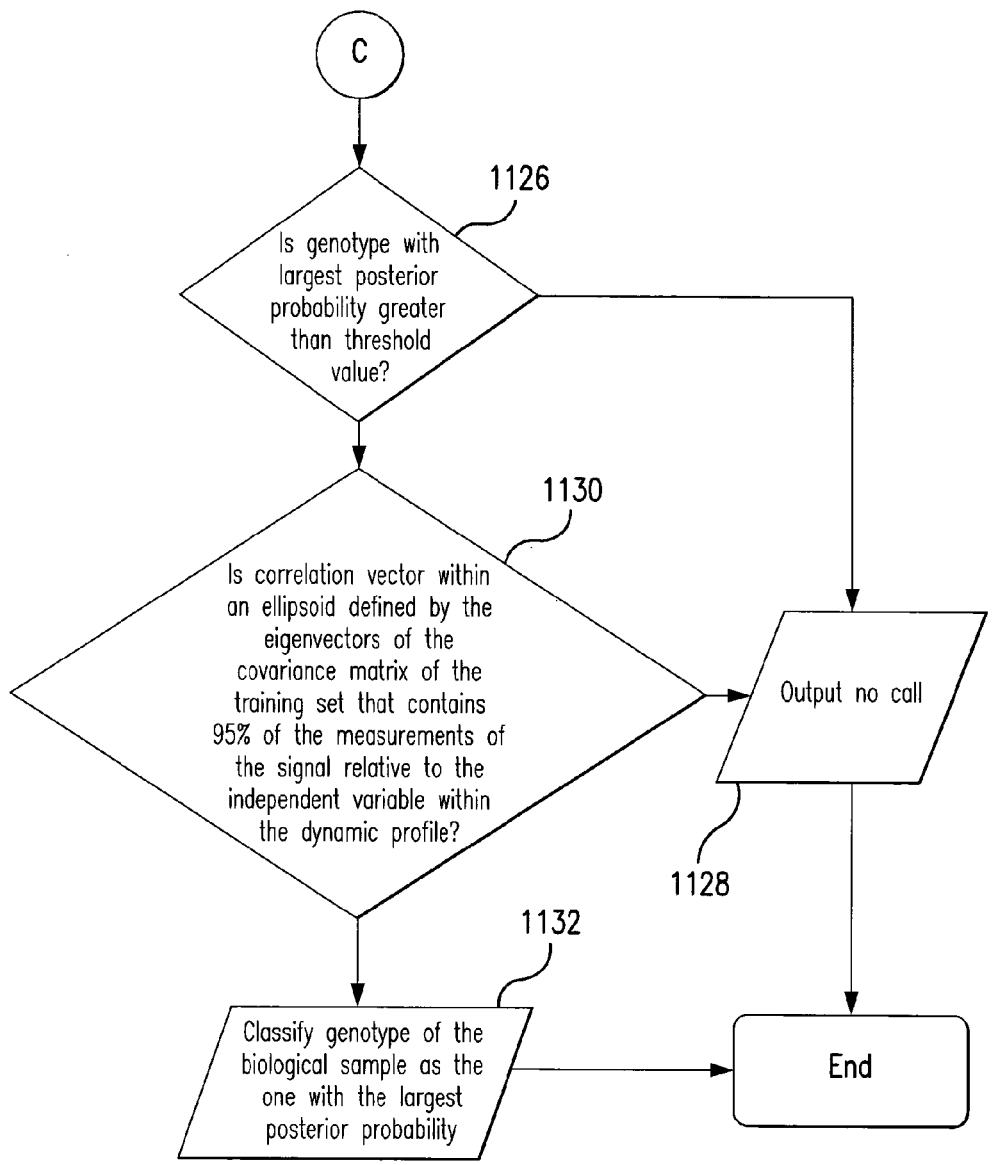

Other embodiments of the invention are illustrated in FIGS. 17A-17C. For example, FIGS. 17A-17C illustrate a flow chart showing how the method of generating the training set 100 and the method of identifying an unknown genotype 1100 may be combined into a method 1700 for determining the identity of the genotype of a nucleic acid present in a biological sample. Measurements of signals relative to an independent variable from a biological sample containing an unknown genotype are generated and input in step 1104. Likewise, measurements of signals from a plurality of samples of a known genotype relative to an independent variable, along with signals of a control genotype associated with each sample, are generated in step 104. A training set is generated first by inputting measurements of signals from multiple biological samples of a known genotype relative to an independent variable, along with measurements of signals corresponding to a control genotype associated with each sample in step 104. These signals are used to generate dynamic profiles of the known genotype in step 102, along with generating positive control dynamic profiles of the control genotype in step 106. The independent variable of the positive control dynamic profiles are shifted such that the correlation coefficient between the known positive control dynamic profile and the measured positive control dynamic profile is maximized in order to generate a shift value in step 108. The dynamic profiles of the known genotype may then be shifted by the shift value in step 110 and normalized to have a standard deviation of 1 and an average value of 0 in step 112.

The dynamic profiles for the known genotype may then be averaged together to generate an average dynamic profile for the known genotype in step 116, as illustrated in FIG. 17B.

Each dynamic profile of the known genotype may then correlated against the average dynamic profile for each known genotype in the class of genotypes in order to generate several correlation vectors r, whose elements are the correlation coefficients of a dynamic profile of a known genotype against each average dynamic profile for each known genotype, in step 126. These correlation vectors r may be transformed into n-spherical coordinates in order to ensure that the correlation coefficients for all dynamic profiles of a particular known genotype against an average dynamic profile of a known genotype are normally distributed in step 128. This step generates several transformed correlation vectors v. The transformed correlation vectors for all dynamic profiles of a particular known genotype may be grouped together in a parameter matrix V for the known genotype, which may be used to generate the mean vector $\mu$ in step 132 and the covariance matrix C for the known genotype in step 134.

FIGS. 17A-17C illustrate the use of a training set generated for a particular genotype for determining whether a genotype is present in a biological sample. A dynamic profile of a biological sample containing the unknown genotype is generated in step 1102. Concurrently, a positive control dynamic profile of a positive control genotype is generated in step 1106. The independent variable of the positive control dynamic profile is shifted such that the correlation coefficient between the known positive control dynamic profile and the measured positive control dynamic profile is maximized in step 1108 in order to generate a shift value. The dynamic profile of the unknown genotype is then shifted by the shift value in step 1110 and normalized to have a standard deviation of 1 and an average value of 0 in step 1112.

In step 1114, the dynamic profile of the unknown genotype is then correlated with one or more average dynamic profiles of a known genotype generated by the method of generating the training set in step 116. The separation-maximizing range is input at step 1702, and only measurements of the signal at independent variable values within the dynamic profile that fall within the separation-maximizing range are compared to points in the average dynamic profile that are also within the separation-maximizing range in step 1114.

Preferably, the dynamic profile of the unknown genotype is correlated with an average dynamic profile for each known genotype within the class of genotypes in order to generate a correlation vector r. This correlation vector is then transformed into n-spherical coordinates in order to force the elements of the correlation vector to be normally distributed, as shown in step 1116, to generate the transformed correlation vector v. In step 1118, the transformed correlation vector v is used, along with the mean vector $\mu$ for a known genotype generated in step 132 and the covariance matrix C for a known genotype generated in step 134, to determine the class-conditional probability $p(v|g_i)$ that a dynamic profile of the known genotype would generate the transformed correlation vector v. The frequency of the known genotype in the population $P(g_i)$ may be inputted to the method at step 1124, and the class conditional probability $p(v|g_i)$ and frequency of the known genotype in the population $P(g_i)$ may be used to calculate the posterior probability that the sample contains the known genotype $p(g_i|v)$ in step 1122. In a preferred embodiment, a posterior probability for each known genotype in the class of genotypes is calculated in this manner as well.

Generally, the unknown genotype is identical to the known genotype that generates the largest posterior probability, but to be certain within a degree of confidence, the largest posterior probability may be compared to a threshold value in step 1126. In some embodiments, if the largest posterior probability is not greater then the threshold value, then the unknown genotype may be identified as the known genotype that generated the largest posterior probability. If the largest posterior probability is greater than the threshold value, a call may be made if the correlation vector v falls within an acceptable range, which is shown as step 1130. Correlation vectors that fall within an n-ellipsoid defined along the eigenvectors of the covariance matrix C for the genotype corresponding to the largest posterior probability fall into the acceptable range. This n-ellipsoid may contain a predetermined threshold percentage of the correlation vectors compiled in the parameter matrix V of the genotype corresponding to the largest posterior probability. If the transformed correlation vector v does fall within this n-ellipsoid, then the unknown genotype may be identified as the genotype corresponding to the largest posterior probability in step 1132.

One or more steps of the embodiments shown in FIGS. 1A, 1B, 11A, 11B, 17A, 17B and 17C may be performed using a computer. Furthermore, the methods of the embodiments shown in FIGS. 1A, 1B, 11A and 11B may be automated by using a computer to perform all of the steps without any input from the user beyond inputting the measurements of the signal relative to the independent variable used to generate the dynamic profiles and the positive control profiles, as well as the probabilities of each possible genotype in the class of genotypes in the population at large. The methods of the invention are optimal for being performed on a computer or in an automated setting because they are direct and rapid solutions to the identification of the genotypes of unknown nucleic acids that require significantly less user intervention and computation than prior computational methods for identification of genotypes. Furthermore, the method takes into account the overall shape and dynamics of the dynamic profile, rather than merely attempting to identify the genotype represented by the dynamic profile from one parameter (e.g. melting temperature).

In accordance with other aspects, the present invention also provides a system for identifying a genotype in a biological sample including at least one unknown genotype. The system comprises a generation module, a correlation module, a class-conditional density module, a posterior probability module, and a determination module. The generation module is capable of generating a dynamic profile of an unknown genotype contained in a biological sample. The dynamic profile comprises measurements of a signal representing a physical change of a nucleic acid containing the unknown genotype relative to an independent variable, such as described herein.

Figure 18:
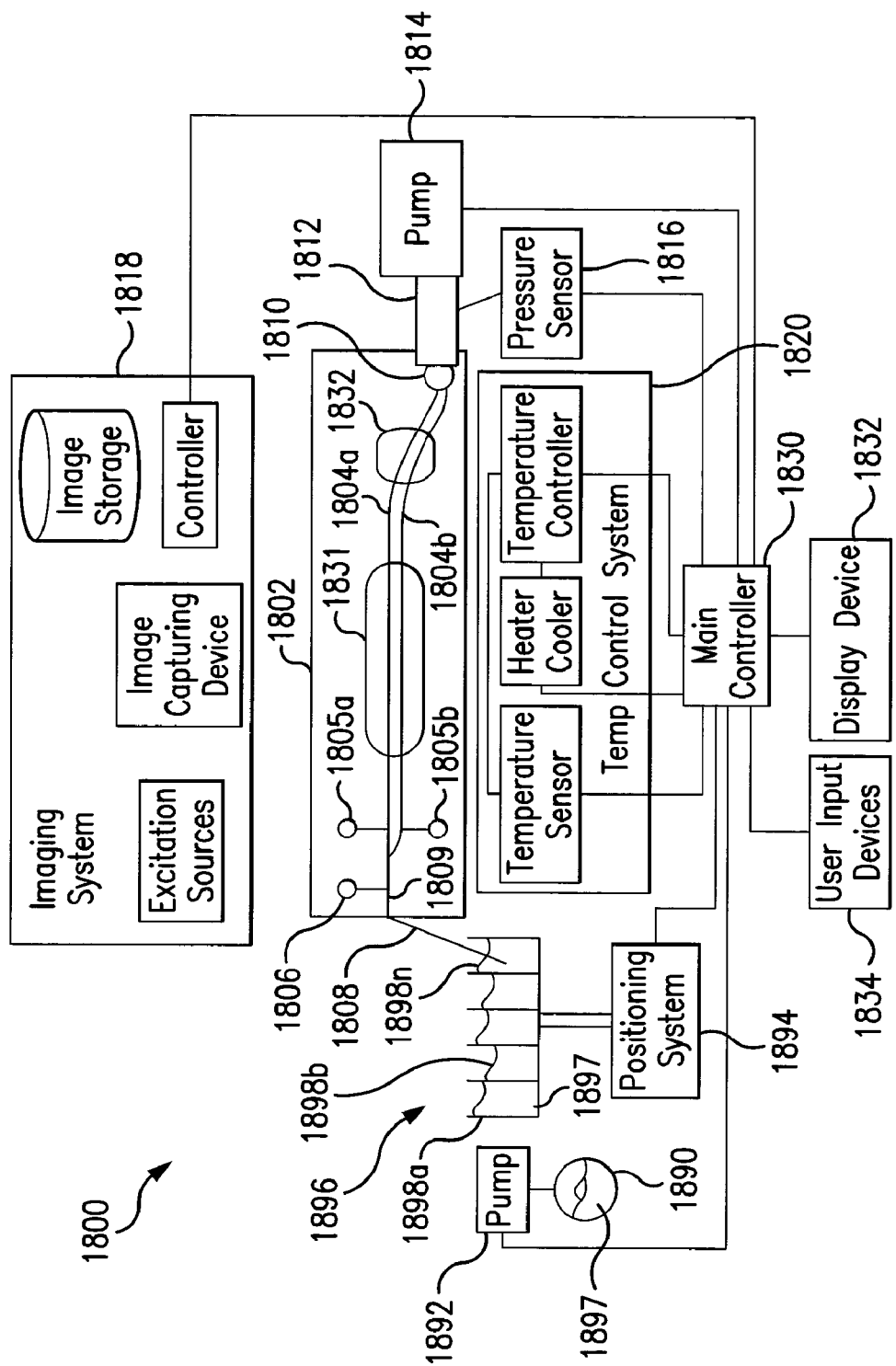
FIG. 18 illustrates a microfluidic device in accordance with some aspects of the invention.

An example of a suitable system for use in accordance with some aspects of the invention, such as generating a dynamic profile of an unknown genotype, is illustrated in connection with FIG. 18. As illustrated in FIG. 18, system 1800 may include a microfluidic device 1802. Microfluidic device 1802 may include one or more microfluidic channels 1804. In the examples shown, device 1802 includes two microfluidic channels, channel 1804a and channel 1804b. Although only two channels are shown in the exemplary embodiment, it is contemplated that device 1802 may have fewer than two or more than two channels. For example, in some embodiments, device 1802 includes eight channels 1804.

Device 1802 may include two DNA processing zones, a DNA amplification zone 1831 (a.k.a., PCR zone 1831) and a DNA melting zone 1832. A DNA sample traveling through the PCR zone 1831 may undergo PCR, and a DNA sample passing through melt zone 1832 may undergo high resolution thermal melting. As illustrated in FIG. 18, PCR zone 1831 includes a first portion of channels 1804 and melt zone 1832 includes a second portion of channels 1804, which is down stream from the first portion.

Device 1802 may also include a sipper 1808. Sipper 1808 may be in the form of a hollow tube. Sipper 1808 has a proximal end that is connected to an inlet 1809 which inlet couples the proximal end of sipper 1808 to channels 1804. Device 1802 may also include a common reagent well 1806 which is connected to inlet 1809. Device 1802 may also include a locus specific reagent well 1805 for each channel 1804. For example, in the embodiment shown, device 1802 includes a locus specific reagent well 1805a, which is connected to channel 1804a, and may include a locus specific reagent well 1805b which is connected to channel 1804b. Device 1802 may also include a waste well 1810 for each channel 1804.

The solution that is stored in the common reagent well 1806 may contain dNTPs, polymerase enzymes, salts, buffers, surface-passivating reagents, one or more non-specific fluorescent DNA detecting molecules, a fluid marker and the like. The solution that is stored in a locus specific reagent well 1805 may contain PCR primers, a sequence-specific fluorescent DNA probe or marker, salts, buffers, surface-passivating reagents and the like.

In order to introduce a sample solution into the channels 1804, system 1800 may include a well plate 1896 that includes a plurality of wells 1898, at least some of which contain a sample solution (e.g., a solution containing a DNA sample). In the embodiment shown, well plate 1896 is connected to a positioning system 1894 which is connected to a main controller 1830.

Main controller 1830 may be implemented, for example, using a PXI-8105 controller which is available from National Instruments Corporation of Austin, Tex. Positioning system 1894 may include a positioner (e.g., the MX80 positioner available from Parker Hannifin Corporation of PA ("Parker")) for positioning well plate 1896, a stepping drive (e.g., the E-AC Microstepping Drive available from Parker) for driving the positioner, and a controller (e.g., the 6K4 controller available from Parker) for controlling the stepping drive.

To introduce a sample solution into the channels 1804, the positioning system 1894 is controlled to move well plate 1896 such that the distal end of sipper 1808 is submerged in the sample solution stored in one of the wells 1898. FIG. 18 shows the distal end of 1808 being submerged within the sample solution stored in well 1898n.

In order to force the sample solution to move up the sipper and into the channels 1804, a vacuum manifold 1812 and pump 1814 may be employed. The vacuum manifold 1812 may be operably connected to a portion of device 1802 and pump 1814 may be operably connected to manifold 1812. When pump 1814 is activated, pump 1814 creates a pressure differential (e.g., pump 1814 may draw air out of a waste well 1810), and this pressure differential causes the sample solution stored in well 1898n to flow up sipper 1808 and through inlet channel 1809 into channels 1804. Additionally, this causes the reagents in wells 1806 and 1805 to flow into a channel. Accordingly, pump 1814 functions to force a sample solution and real-time PCR reagents to flow through channels 1804. As illustrated in FIG. 18, melt zone 1832 is located downstream from PCR zone 1831. Thus, a sample solution will flow first through the PCR zone and then through the melting zone.

Referring back to well plate 1896, well plate 1896 may include a buffer solution well 1898a. In one embodiment, buffer solution well 1898a holds a buffer solution 1897. Buffer solution 1897 may comprise a conventional PCR buffer, such as a conventional real-time (RT) PCR buffer. Conventional PCR buffers are available from a number of suppliers, including: Bio-Rad Laboratories, Inc., Applied Biosystems, Roche Diagnostics, and others.

In order to achieve PCR for a DNA sample flowing through the PCR zone 1831, the temperature of the sample must be cycled, as is well known in the art. Accordingly, in some embodiments, system 1800 includes a temperature control system 1820. The temperature control system 1820 may include a temperature sensor, a heater/cooler, and a temperature controller. In some embodiments, a temperature control system 1820 is interfaced with main controller 1830 so that main controller 1830 can control the temperature of the samples flowing through the PCR zone and the melting zone. Main controller 1830 may be connected to a display device for displaying a graphical user interface. Main controller 1830 may also be connected to user input devices 1834, which allow a user to input data and commands into main controller 1830.

To monitor the PCR process and the melting process that occur in PCR zone 1831 and melt zone 1832, respectively, system 1800 may include an imaging system 1818. Imaging system 1818 may include an excitation source, an image capturing device, a controller, and an image storage unit. Other aspects of a suitable system in accordance with some aspects of the invention are disclosed in U.S. Patent Application Publication No. 2008/0176230, incorporated herein by reference in its entirety.

The system 1800 further includes an appropriately controllable computer in communication with the user input devices 1834, display device 1836 and the main controller 1830. The computer receives information from, among many sources, the imaging system 1818 and temperature control system 1820 and enables the identification of an unknown genotype in a biological sample in accordance with some aspects of the invention, as well as enabling generation of a training set to allow a machine to recognize a known genotype from within a class of genotypes in accordance with another aspect of the invention.

As described above, the system in accordance with this aspect of the present invention comprises a generation module. The generation module is capable of generating a dynamic profile of an unknown genotype contained in a biological sample. The dynamic profile comprises measurements of a signal representing a physical change of a nucleic acid containing the unknown genotype relative to an independent variable. In one embodiment, the generation module is any device capable of taking measurements of a signal representing a physical change of a nucleic acid containing the unknown genotype relative to an independent variable and processing the measurements to produce the dynamic profile of the unknown genotype. In another embodiment, the generation module is the microfluidic device described above.

The system in accordance with some aspects of the present invention further comprises a correlation module capable of correlating the dynamic profile of the unknown genotype with an average dynamic profile, which may be an average normalized dynamic profile as described herein, of a known genotype for each genotype in a class of known genotypes. The correlation module is capable of generate a correlation vector whose elements include a correlation coefficient between the dynamic profile of the unknown genotype and the average normalized dynamic profile for each known genotype in the class of known genotypes. Each of the average dynamic profiles for a known genotype is the average dynamic profile of a known genotype contained in a training set for that genotype. In one embodiment, the training set for a known genotype may additionally include a mean transformed vector for the known genotype and a covariance matrix for the known genotype. In another embodiment, the correlation module is also capable of transforming the correlation vector to a transformed vector in which each element of the transformed vector is normally distributed. In accordance with one embodiment, the correlation module comprises an appropriately programmed computer or software stored on a computer readable medium, where the software is configured such that when executed by a computer, the software enables the computer to correlate the dynamic profile of the unknown genotype with the average dynamic profile of a known genotype to generate the correlation vector. The appropriately programmed computer or software may also be configured such that when executed by a computer, the software enables the computer to transform the correlation vectors to transformed vectors.

The system in accordance with some aspects of the present invention further comprises a class conditional density module. The class conditional density module is capable of calculating the likelihood of the unknown genotype being a known genotype for each of the known genotypes in the class of known genotypes using the class conditional densities of each of the known genotypes in the class of known genotypes. The class conditional densities may be calculated using mean transformed vectors and covariance matrices for each known genotype. The mean transformed vectors and covariance matrices may be obtained from a matrix comprising grouped transformed vectors for each known genotype obtained from a training set. In accordance with one embodiment, the class conditional density module comprises an appropriately programmed computer or software stored on a computer readable medium, where the software is configured such that when executed by a computer, the software enables the computer to calculate the likelihoods from the class conditional densities.

In a further embodiment, the system includes a posterior probability module. The posterior probability module is capable of calculating the posterior probability that the biological sample contains each known genotypes from the likelihoods calculated by the class-conditional density module. In one embodiment, the posterior probability can be calculated form the calculated likelihoods and Bayes' theorem. In accordance with one embodiment, the posterior probability module comprises an appropriately programmed computer or software stored on a computer readable medium, where the software is configured such that when executed by a computer, the software enables the computer to calculate the posterior probabilities.

The system may further include a determination module capable of determining whether the known genotype with the largest posterior probability falls within an acceptable threshold to determine if the unknown genotype is classified as the genotype with the largest posterior probability which thus identifies the unknown genotype. In one embodiment, the determination module is also capable of determining whether the transformed vector obtained from the correlation vector falls within an acceptable range within those determined from the training set for the genotype with the largest posterior probability which increases the confidence level that the identification of the genotype is correct. The acceptable range may be an n-ellipsoid defined by the eigenvectors of the covariance matrix of the training set that contains a predetermined percentage of the correlation vectors in the parameter matrix. In one embodiment, the acceptable range is an ellipsoid defined by the eigenvectors of the covariance matrix of the training set that contains a pre defined percentage (e.g., 99%) of the measurements of the signal relative to the independent variable within a dynamic profile. In accordance with one embodiment, the determination module comprises an appropriately programmed computer or software stored on a computer readable medium, where the software is configured such that when executed by a computer, the software enables the computer to determine the identity of the unknown genotype. The appropriately programmed computer or software may also be configured such that when executed by a computer, the software enables the computer to determine whether the transformed vector falls within the acceptable range.

In some aspects of the invention, the system may further include an error correction module. The error correction module is capable of comparing a positive control dynamic profile to a known dynamic profile for a control genotype to determine a shift value for the independent variable of the dynamic profile. The error correction module is also capable of shifting the independent variable in the dynamic profile for the unknown genotype by the shift value. In accordance with one embodiment, the error correction module comprises an appropriately programmed computer or software stored on a computer readable medium, where the software is configured such that when executed by a computer, the software enables the computer to calculate the shift value and to shift the independent variable in the dynamic profile for the unknown genotype.

In another aspect of the invention, the system includes a training set module. The training set module comprises an average dynamic profile for each known genotype in the class of known genotypes. The average dynamic profile for the known genotype may include average measurements of various dynamic profiles of each known genotype relative to an independent variable. The average dynamic profiles may be average normalized dynamic profiles as described herein. The training set module also comprises a parameter matrix. The elements of the parameter matrix are correlation vectors in which each correlation vector includes a correlation coefficient between a dynamic profile and each average dynamic profile for each known genotype in the class of known genotypes. In a further embodiment, the training set module includes a mean transformed vector. The elements of the mean transformed vector are the average values of the correlation coefficients of each dynamic profile of each known genotype against the average dynamic profiles of each known genotype in the class of genotypes. Further, the training set module may include a covariance matrix, which may be the covariance matrix of the parameter matrix. In accordance with one embodiment, the training set module comprises an appropriately programmed computer or software stored on a computer readable medium, where the software is configured such that when executed by a computer, the software enables the computer to obtain the data contained within the training set module.

In a further embodiment, the system also includes a separation-maximizing range selection module. The separation-maximizing range selection module is capable of calculating a within-class scatter matrix for the class of known genotypes, using the mean vector and the vector of correlation vector for each genotype. Additionally, the separation-maximizing range selection module is capable of calculating a between-class scatter matrix for the class of known genotypes using the mean vector and the vector of correlation vectors for each known genotype. The separation-maximizing range selection module is also capable of determining a separation ratio that is the ratio of the determinant of the within-class scatter matrix to the determinant of the between-class scatter matrix, and selecting a separation-maximizing range in order to maximize this separation ratio. In accordance with one embodiment, the separation-maximizing range selection module comprises an appropriately programmed computer or software stored on a computer readable medium, where the software is configured such that when executed by a computer, the software enables the computer to determine a separation-maximizing range for the independent variable.

The system according to the invention may further include a translation module. The translation module is capable of translating a correlation vector into n-spherical coordinates, where n is at least one fewer than the number of genotypes that make up all of the possible mutations. In accordance with one embodiment, the translation module comprises an appropriately programmed computer or software stored on a computer readable medium, where the software is configured such that when executed by a computer, the software enables the computer to translate a correlation vector into n-spherical coordinates.

The methods and system of the present invention may be understood with reference to the following examples, which are not intended to be limiting.

EXAMPLE 1

Generation of Training Sets for Warfarin VKORC1 Polymorphism

Figure 2:
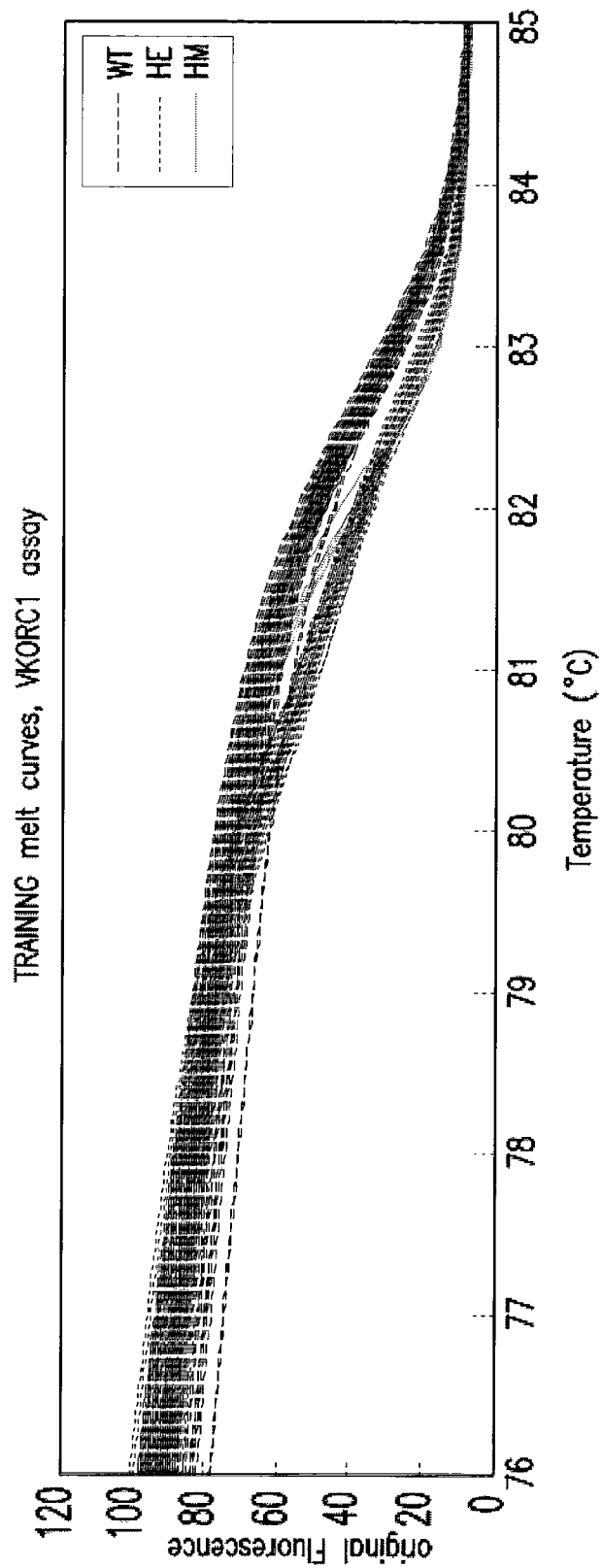
FIG. 2 illustrates fluorescence versus temperature dynamic profiles for each genotype within the Warfarin VKORC1 class.
Figure 3:
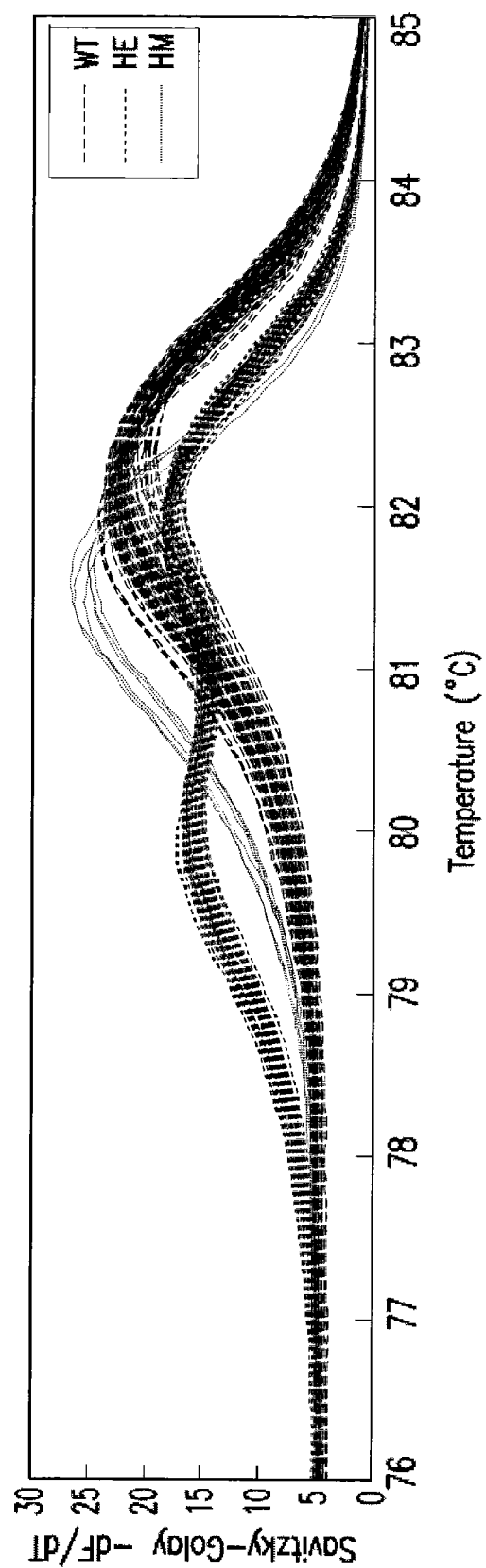
FIG. 3 illustrates a plot of the negative derivative of the fluorescence versus temperature dynamic profiles for each genotype within the Warfarin VKORC1 class.

Several thermal melt curves which include measurements of fluorescence at equally spaced temperature intervals for each of the Warfarin VKORC1 polymorphism genotypes were obtained by high resolution thermal melting from 50 to 95° C. at 0.5° C. per second using LC Green fluorescent dye following a 40 PCR cycle run on the Roche LC280 light cycler. These curves are shown in FIG. 2. −dF/dT was calculated for each of the generated curves by applying a Savitsky-Golay derivative filter, resulting in the curves shown in FIG. 3. A positive control thermal melt curve was obtained through high-resolution thermal melt analysis of a known sample containing the wild-type genotype of the Warfarin VKORC1 polymorphism, along with each thermal melt curve of each of the Warfarin VKORC1 polymorphism genotypes. Measurements of fluorescence for the positive control were averaged over several runs in order to generate a reference standard thermal melt curve for the positive control. The positive control thermal melt curve was shifted by a value Δx chosen in order to maximize the correlation coefficient between the positive control thermal melt curve and the reference standard thermal melt curve. Each thermal melt curve of each of the Warfarin VKORC1 polymorphism genotypes was normalized to have an identical standard deviation (1) and an identical average value (0). These curves are shown in FIG. 5 as the thinner lines.

The Warfarin VKORC1 polymorphism has three possible genotypes: wild-type (WT), heterozygous mutant (HE), and homozygous mutant (HM). All of the thermal melt curves corresponding to the WT genotype were averaged together to generate an average thermal melt curve for the WT genotype. Average thermal melt curves for the HE and HM genotypes were generated in a similar manner. These average thermal melt curves for the WH, HE, and HM genotypes are plotted in FIG. 5 as dark, thick lines.

Each of the thermal melt curves generated from a sample containing the WT genotype was correlated against the average thermal melt curve for the WT, HE, and HM genotypes to generate three correlation coefficients for each thermal melt curve: $r_{wt}$, $r_{sh}$, and $r_{hm}$, which represent the correlation coefficient of the thermal melt curve against the average thermal melt curves for the WT, HE, and HM genotypes, respectively.

Thus, each thermal melt curve has a correlation vector r associated with it, where the correlation vector r is $$r = \begin{bmatrix} r_{wt} \\ r_{he} \\ r_{hm} \end{bmatrix}$$

FIG. 6 shows a plot of the correlation vectors associated with the thermal melt curves for the WT, HE, and HM genotypes. From this plot, it may be seen that the correlation vectors are not normally distributed. FIG. 10 shows the same points as FIG. 6, but projected on to the plane of x+y+z=0. In this two-dimensional projection, the points are normally distributed. However, some information may be lost in this manner, because the correlation vectors are only normally distributed when projected on to a two-dimensional plane. Thus, in order to obtain a normal distribution of the correlation vectors, all of the correlation vectors for the thermal melt curves are translated into 2-spherical coordinates in order to ensure that the distribution of values of $r_{wt}$, $r_{sh}$, and $r_{hm}$ is a normal distribution, e.g. it is a Gaussian distribution. This transformation may be achieved through the following equations:

$$l = \sqrt{r_{wt}^2 + r_{he}^2 + r_{hm}^2}$$

$$a_1 = \tan^{-1}\left(\frac{r_{he}}{r_{wt}}\right)$$

$$a_2 = \tan^{-1}\left(\frac{r_{hm}}{\sqrt{(r_{wt})^2 + (r_{he})^2}}\right)$$

$$\text{Transformed vector } v = \begin{bmatrix} l \\ a_1 \\ a_2 \end{bmatrix}$$

In some embodiments, if $N_g$, the number of possible genotypes or dimensions, is greater than 3, this transformation can be extended as follows:

$$a_3 = \tan^{-1}\left(\frac{r_4}{\sqrt{(r_1)^2 + (r_2)^2 + (r_3)^2}}\right)$$

$$\text{Transformed vector: } v = \begin{bmatrix} l \\ a_1 \\ a_2 \\ a_3 \end{bmatrix}$$

and so on for other embodiments in which $N_g$ is greater than 4. By transforming the correlation vectors into spherical coordinates, a normal distribution of the correlation vectors is achieved, as can be seen in FIG. 8. Likewise, FIG. 7 shows bar graphs that indicate the correlation coefficients themselves are not normally distributed for the WT class; however, by translating the correlation vectors into spherical coordinates, a more normal distribution may be achieved, as shown in FIG. 9.

The transformed correlation vectors v associated with the WT thermal melt curves are grouped together (stacked horizontally) in a parameter matrix $V_{wt}$:

$$V_i = [v_1 v_2 \ldots v_{n_j}]$$

where $n_i$ is the number of dynamic profiles used to calculate the average normalized profile of the wild-type genotype. In $V_i$, each row is a parameter (i.e. l, $a_1$, or $a_2$), and each column is an observation for a different dynamic (melt) curve for that particular genotype. The mean of each row of $V_{wt}$ is calculated to give the mean vector $\mu_{wt}$.

$$\mu_{wt} = \begin{bmatrix} \mu(l) \\ \mu(a_1) \\ \mu(a_2) \end{bmatrix}$$

where $\mu(l)$, $\mu(a_1)$, and $\mu(a_2)$ are the average values for l, $a_1$, and $a_2$, respectively. Each element (i,j) of the covariance matrix $C_{wt}$ of $V_{wt}$ is then calculated as follows:

$$C_{WT}(i,j) = \frac{\sum_{m=1}^{N_{WT}} [(V_{WT}(i,m) - \mu_{WT}(i))(V_{WT}(j,m) - \mu_{WT}(j))]}{N_{WT} - 1}$$

The covariance matrix $C_{wt}$, the mean vector $\mu_{wt}$, and the average thermal melt curve for the WT genotype comprise the training set for the WT genotype. Similar training sets are be generated for the HE and HM, and/or any other possible genotypes through the same steps.

Quantification of the Degree of Separation Between Genotypes

In some embodiments, the separation between genotypes in the Warfarin VKORC1 polymorphism may be maximized by selecting a temperature window for data to be used in the classification analysis. The bounds of this temperature window, $T_{min}$ and $T_{max}$, are chosen in such a way as to maximize the separation factor q, which is the ratio of the determinant of the between-class scatter matrix to the determinant of the within-class scatter matrix, as is shown in the following equation:

$$q = \frac{|\tilde{S}_B|}{|\tilde{S}_W|}$$

The within-class scatter matrix may be calculated from the WT, HE, and HM training sets by the following formula:

$$\tilde{S}_W = \sum_{v \in V_{WT}} (v - \mu_{WT})(v - \mu_{WT})^T + \sum_{v \in V_{HE}} (v - \mu_{HE})(v - \mu_{HE})^T + \sum_{v \in V_{HM}} (v - \mu_{HM})(v - \mu_{HM})^T$$

wherein v is a column or element of $V_{WT}$, $V_{HE}$, or $V_{HM}$ respectively.

The between-class scatter matrix may be calculated from the following equation:

$$\tilde{S}_B = N_{WT}(\mu_{WT} - \mu)(\mu_{WTi} - \mu)^T + N_{HE}(\mu_{HE} - \mu)(\mu_{HEi} - \mu)^T + N_{HM}(\mu_{HM} - \mu)(\mu_{HMi} - \mu)^T$$

wherein $\mu$ is a vector whose elements are the mean values of $r_{wt}$, $r_{sh}$, and $r_{hm}$ for all the thermal melt curves used in creating the training sets for the Warfarin VKORC1 polymorphism, and where $N_{WT}$, $N_{HE}$, and $N_{HM}$ are the number of measurements that make up the average profile for their respective genotypes.

The separation factor q is maximized by iteratively choosing a different $T_{min}$ and $T_{max}$, calculating new between-class scatter and within-class scatter matrices, and then recording the value of q until a maximum value is found. The results of this process for the Warfarin VKORC1 polymorphism class of genotypes are shown in FIG. 16. FIG. 16 shows a plot of $T_{max}$ vs. $T_{min}$ vs. log(q). Log(q) is represented in grayscale; darker grays represent larger values of q, while lighter grays represent lower values of q. In this example, the maximum value of q was found to be when $T_{min}$ was 79° C. and $T_{max}$ was 82° C.

EXAMPLE 2

Generation of Training Sets for Coagulation Factor MTHFR677 Polymorphism.

Figure 19:
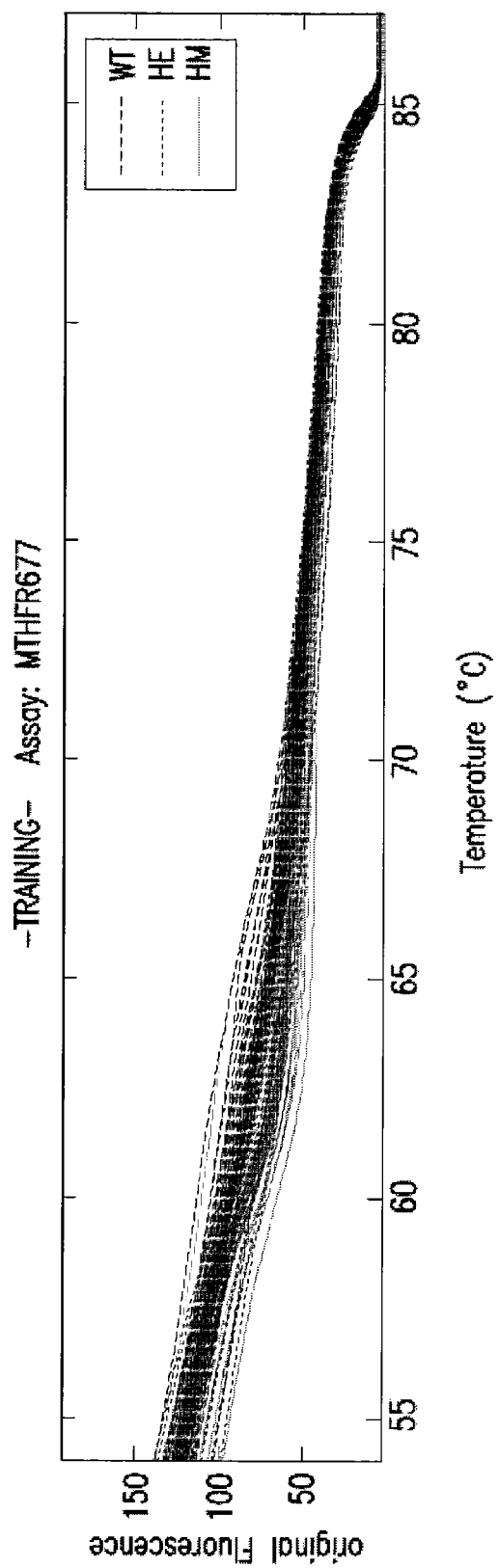
FIG. 19 illustrates fluorescence versus temperature dynamic profiles for each genotype within the MTHFR 667 polymorphism class.
Figure 21:
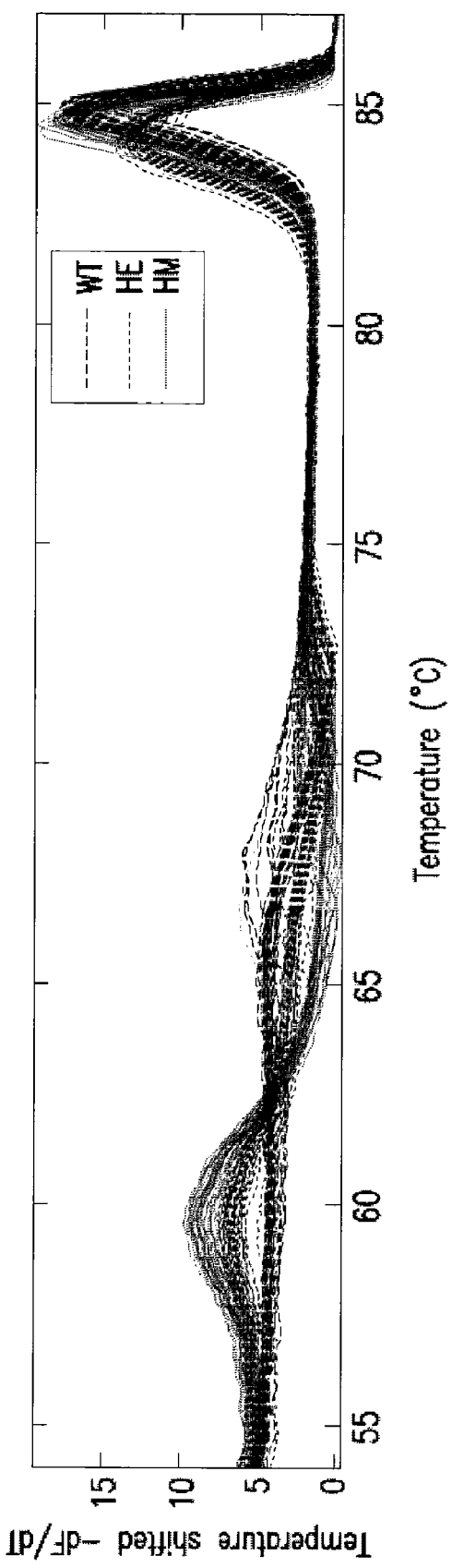
FIG. 21 illustrates the dynamic curves of FIG. 20 after having been horizontally shifted by a shift value determined by correlation of a positive control dynamic profile to a known dynamic profile for a positive control.
Figure 22:
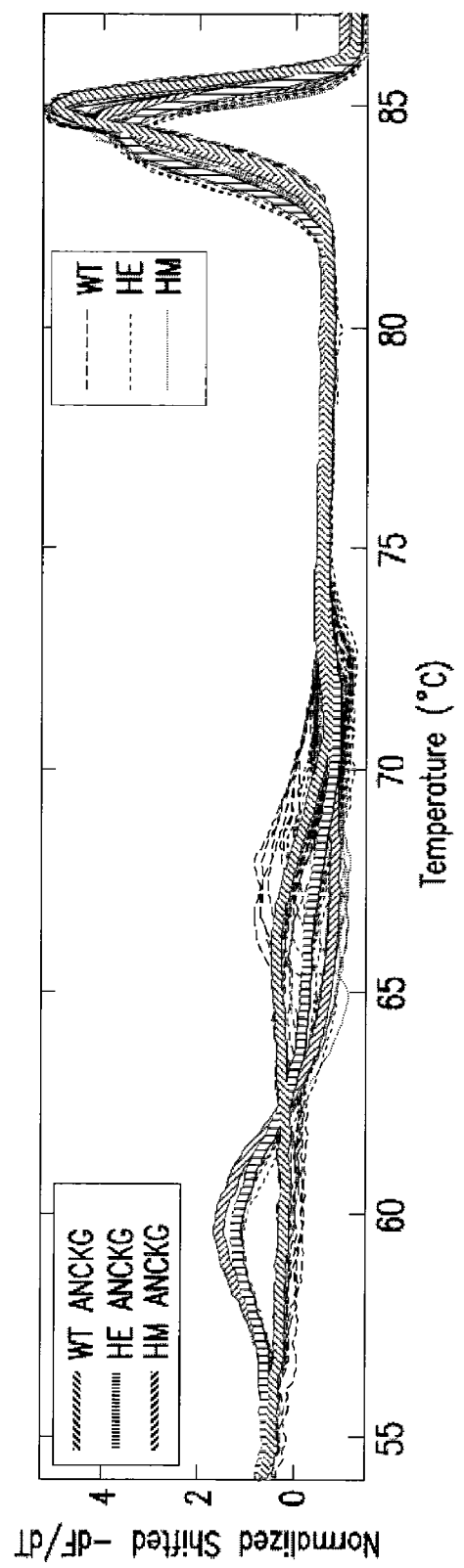
FIG. 22 illustrates the dynamic profile of FIG. 21 after normalization to a predetermined standard deviation, and the average profile of each genotype within the polymorphism class (class of known genotypes) according to one embodiment.

Several thermal melt curves which include measurements of fluorescence at equally spaced temperature intervals for each of the Coagulation Factor MTHFR677 polymorphism genotypes were obtained by high resolution thermal melting from 50 to 95° C. at 0.5° C. per second using LC Green fluorescent dye following a 40 PCR cycle run on the Roche LC480 light cycler. These curves are shown in FIG. 19. –dF/dT was calculated for each of the generated curves by applying a Savitsky-Golay Filter resulting in the curves shown in FIG. 20. The curves are temperature shifted and normalized in the same manner as was done for the thermal melt curves for the Warfarin VKORC1 polymorphism; these shifted and normalized curves are shown in FIG. 21. The Coagulation Factor MTHFR677 polymorphism has three possible genotypes: wild-type (WT), heterozygote (HE), and homozygous (HM). Average thermal melt curves for these genotypes were generated in the same manner as was done in Example 1. These average thermal melt curves for the WH, HE, and HM genotypes are plotted in FIG. 22 as dark, thick lines.

Each of the thermal melt curves generated from a sample containing the a particular genotype is analyzed in the same manner as in Example 1 in order to generate correlation coefficients for each thermal melt curve: $r_{wt}$, $r_{he}$, and $r_{hm}$. Each thermal melt curve has a correlation vector r associated with it, where the correlation vector r is $$r = \begin{bmatrix} r_{wt} \\ r_{he} \\ r_{hm} \end{bmatrix}$$

Figure 23:
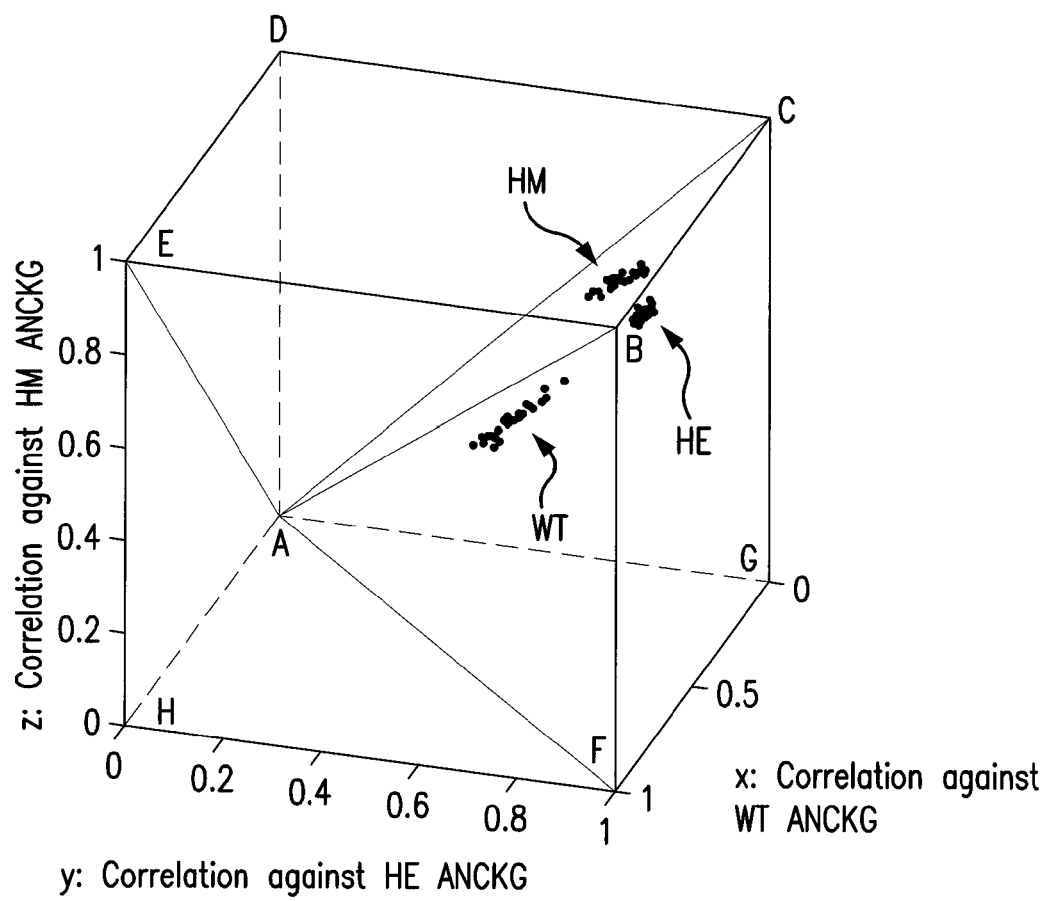
FIG. 23 illustrates a three-dimensional plot of correlation vectors for the MTHFR 667 polymorphism class in which the elements of the correlation vector are not normally distributed.
Figure 24:
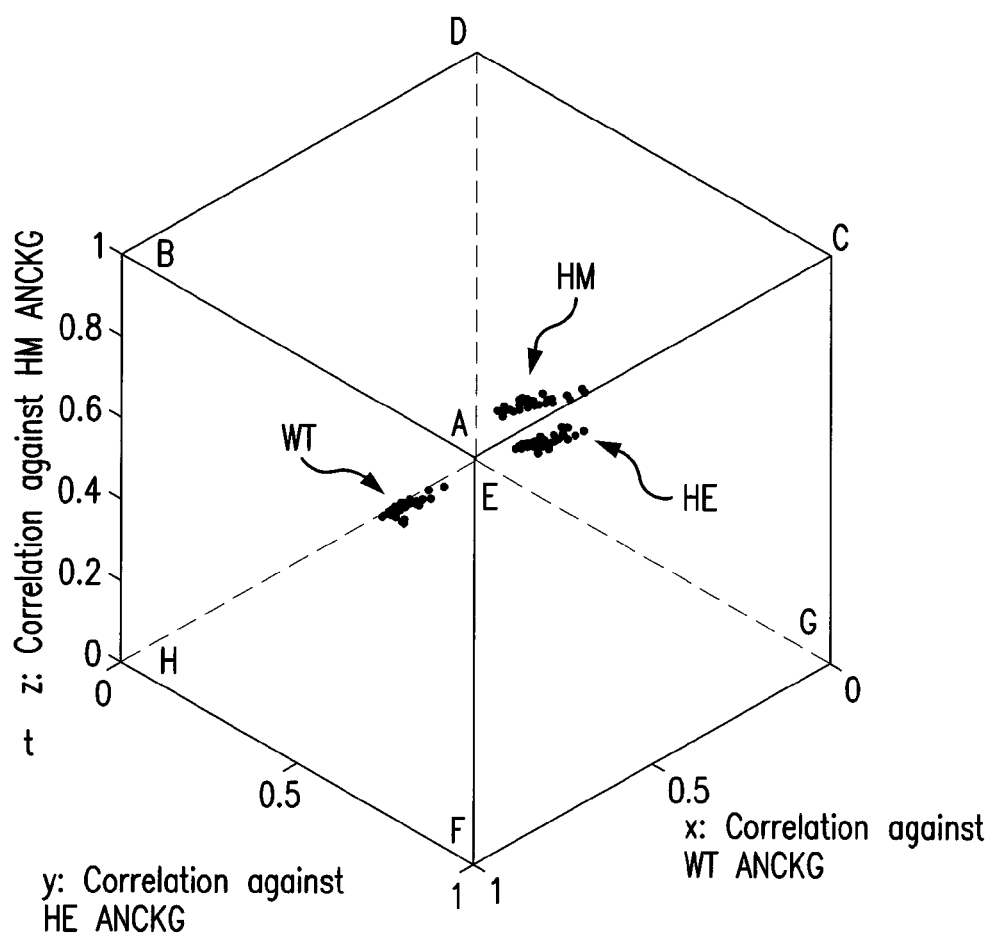
FIG. 24 illustrates a three-dimensional plot of correlation vectors for the MTHFR 667 polymorphism class projected on to the plane x+y+z=0, wherein the correlation vectors are normally distributed.

FIG. 23 shows a plot of the correlation vectors associated with the thermal melt curves for the WT, HE, and HM genotypes. From this plot, it may be seen that the correlation vectors again are not normally distributed. FIG. 24 shows the same points as FIG. 23, but projected on to the plane of x+y+z=0. In this two-dimensional projection, the points are normally distributed. However, some information may be lost in this manner, because the correlation vectors are only normally distributed when projected on to a two-dimensional plane, even though the correlation vectors have three dimensions. Thus, in order to obtain a normal distribution of the correlation vectors, all of the correlation vectors for the thermal melt curves are translated into spherical coordinates in order to ensure that the distribution of values of $r_{wt}$, $r_{sh}$, and $r_{hm}$ is a normal distribution in the same way as was done for the Warfarin VKORC1 example.

Figure 25:
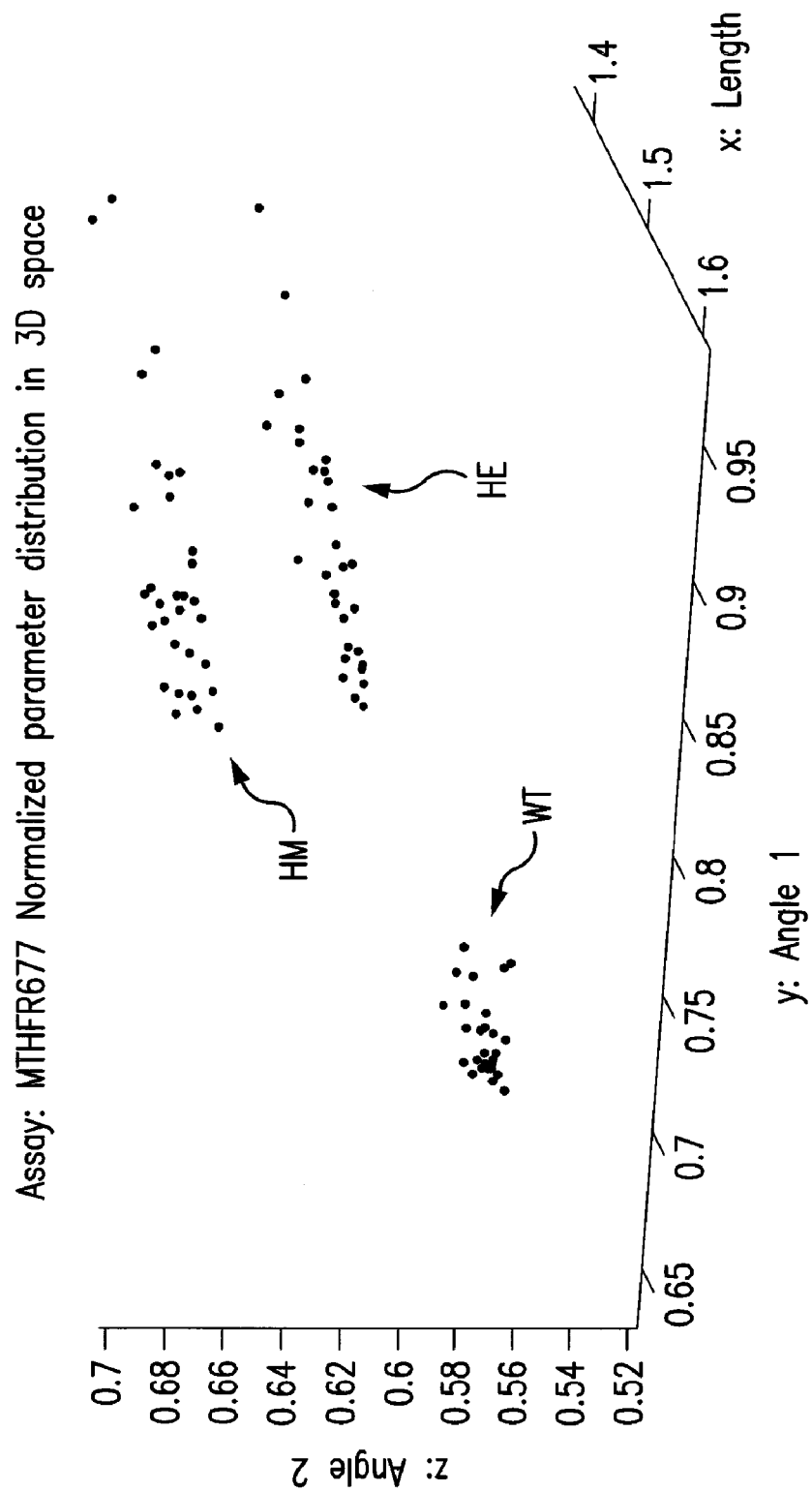
FIG. 25 illustrates a three-dimensional plot of correlation vectors for the MTHFR667 polymorphism class in which the correlation vectors have been translated into spherical coordinates and are normally distributed.

By transforming the correlation vectors into spherical coordinates, a normal distribution of the correlation vectors is achieved, as can be seen in FIG. 25. The transformed correlation vectors v associated with the WT thermal melt curves are grouped together in a parameter matrix $V_{wt}$, as was done in Example 1. Again, the mean of each column of $V_{wt}$ is calculated to give the mean vector $\mu_{wt}$. The covariance matrix $C_{wt}$ of $V_{wt}$ is then calculated as disclosed in Example 1. The covariance matrix $C_{wt}$, the mean vector $\mu_{wt}$, and the average thermal melt curve for the WT genotype comprise the training set for the WT genotype. Similar training sets are generated for the HE and HM genotypes through the same steps.

Figure 20:
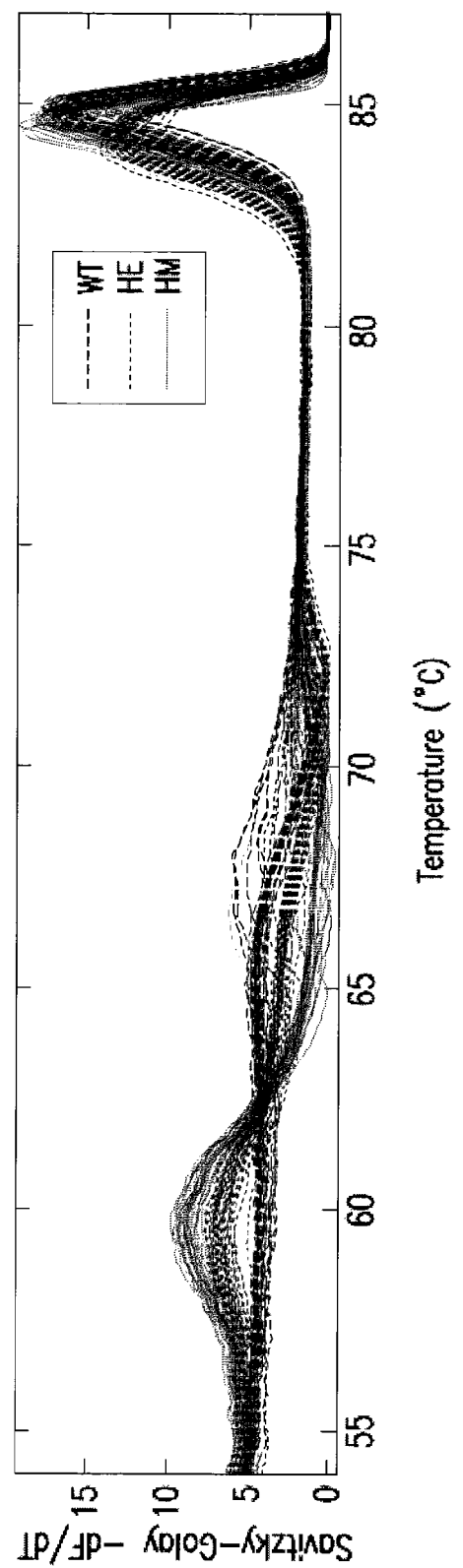
FIG. 20 illustrates a plot of the negative derivative of the fluorescence versus temperature dynamic profiles for each genotype within the MTHFR 667 polymorphism class.

Both probe melting (at lower temperatures) and amplicon melting (at higher temperatures) are observed in the thermal melt curves for the Coagulation Factor MTHFR677 Polymorphism, which is shown by the appearance of two peaks for each genotype in FIG. 20. The method does not rely on fitting the thermal melt data to any curves in order to identify the genotype, but relies exclusively on pattern-matching and statistical analysis in order to identify the genotype. As such, the present method is more versatile than prior methods for identification of a genotype from a dynamic profile.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of determining the identity of the genotype of a nucleic acid present in a biological sample, said method comprising the steps of:
   (a) providing a microfluidic device comprising one or more microfluidic channels and a controller that interfaces with the microfluidic device;
   (b) introducing a biological sample into the microfluidic device;
   (c) causing the biological sample to move through the microfluidic channel;
   (d) performing an amplification reaction on the biological sample;
   (e) causing a physical change of a nucleic acid from the biological sample;
   (f) measuring a signal representing said physical change;
   (g) causing the controller to perform the following steps:
   (i) generate a dynamic profile of an unknown genotype contained in the biological sample, wherein the dynamic profile comprises the measurements of the signal representing a physical change of the nucleic acid containing the unknown genotype relative to an independent variable;
   (ii) correlate the dynamic profile of the unknown genotype with an average dynamic profile of each known genotype in a class of known genotypes to generate a correlation vector, wherein the average dynamic profile of each known genotype comprises average measurements of a signal representing the physical change of a nucleic acid containing the known genotype relative to the independent variable and wherein the correlation vector comprises correlation coefficients between the dynamic profile of the unknown genotype and the average dynamic profile for each known genotype in the class of known genotypes; and
   (iii) determine whether the correlation vector or a transformation thereof falls within an acceptable range to classify the unknown genotype as one of the known genotypes in the class of known genotypes, whereby the identity of the genotype of the nucleic acid in the biological sample is determined.

2. The method of claim 1, wherein the average dynamic profiles for the known genotypes are obtained from a training set.

3. The method of claim 1, wherein the independent variable is temperature.

4. The method of claim 1, wherein the physical change is denaturation of the nucleic acid.

5. The method of claim 4, wherein the signal representing denaturation of the nucleic acid is fluorescence.

6. The method of claim 1, wherein the independent variable is electric potential.

7. The method of claim 1, wherein the physical change is oxidation of a redox-active molecule in the biological sample.

8. The method of claim 7, wherein the signal representing oxidation of the redox-active molecule is current.

9. The method of claim 1, wherein the controller is an appropriately programmed computer.

10. The method of claim 1, wherein the method is automated.

11. The method of claim 1, wherein a posterior probability that the unknown genotype is a known genotype is calculated for each known genotype from the correlation coefficients.

12. The method of claim 11, wherein step (iii) comprises determining whether the largest posterior probability and the correlation coefficient against the average dynamic profile for the corresponding known genotype fall within acceptable predefined thresholds to classify the unknown genotype.

13. The method of claim 11, wherein said correlating step (ii) further comprises:
   (1) calculating a likelihood of the unknown genotype being a known genotype for each of the known genotypes in the class of known genotypes using class conditional densities of each known genotype; and (2) calculating the posterior probability that the biological sample contains each known genotype from the calculated likelihoods.

14. The method of claim 13, wherein the posterior probability is calculated using Bayes' theorem.

15. The method of claim 13, wherein the class conditional densities are calculated using mean transformed vectors and covariance matrices for each genotype.

16. The method of claim 15, wherein the mean transformed vectors and covariance matrices are obtained from a matrix comprising grouped transformed vectors for each genotype obtained from a training set.

17. The method of claim 13, wherein the correlation vector is transformed to a vector wherein each element of the transformed vector is normally distributed.

18. The method of claim 17, wherein the elements of the transformed vector are expressed as spherical coordinates.

19. The method of claim 1, wherein the dynamic profile is normalized to have a predetermined mean and standard deviation.

20. The method of claim 1, further comprising the steps of:
(iv) generating a positive control dynamic profile of a control genotype, wherein the positive control dynamic profile comprises measurements of a signal representing a physical change of a nucleic acid containing the control genotype relative to an independent variable taken concurrently with the measurements that comprise the dynamic profile of the unknown genotype;
(v) comparing the positive control dynamic profile to a standard positive control dynamic profile for the control genotype to determine a shift value for the independent variable; and
(vi) shifting the independent variable of the dynamic profile of the positive control and the dynamic profile of the unknown genotype by the shift value.

21. A method of generating a training set to allow a machine to recognize a known genotype from a class of known genotypes, comprising:
(a) obtaining dynamic profiles according to the method of claim 1;
(b) causing the controller to perform the following steps:
(i) grouping multiple dynamic profiles of the same genotype for each known genotype in a class of known genotypes, wherein each dynamic profile comprises measurements of a signal representing a physical change of a nucleic acid containing the known genotype relative to an independent variable;
(ii) normalizing each of the dynamic profiles;
(iii) averaging the normalized dynamic profiles of the same genotype to obtain an average normalized dynamic profile for each known genotype in the class of known genotypes;
(iv) correlating each dynamic profile with the average normalized dynamic profile of each known genotype in the class of known genotypes to generate a correlation vector for each dynamic profile, wherein each correlation vector comprises correlation coefficients for the dynamic profile against each average normalized dynamic profile of each known genotype in the class of known genotypes;
(v) transforming the correlation vectors such that when grouped together by genotype, each of the elements of the transformed vector are normally distributed;
(vi) compiling each transformed vector into a matrix of transformed vectors, such that there is one matrix for each known genotype in the class of known genotypes;
(vii) generating a mean transformed vector whose elements include an averaged transformed vector for each known genotype where the transformed vector is the average of each compiled matrix; and
(viii) calculating a covariance matrix for the known genotypes by calculating the covariance matrix of each of the compiled matrices,
wherein the training set comprises the average normalized dynamic profile for each known genotype, a mean transformed vector for each known genotype and a covariance matrix for each known genotype.

22. The method of claim 21, further comprising the steps of:
(ix) generating a positive control dynamic profile of a control genotype, wherein the positive control dynamic profile comprises measurements of a signal representing a physical change of a nucleic acid containing the control genotype relative to an independent variable taken concurrently with the measurements that comprise the dynamic profile of the unknown genotype;
(x) comparing the positive control dynamic profile to a standard positive control dynamic profile for the control genotype to determine a shift value for the independent variable; and
(xi) shifting the independent variable of the dynamic profile of the positive control and the dynamic profiles of the known genotypes by the shift value.

23. The method of claim 22, further comprising the step of scaling the independent variable of the dynamic profile of the positive control and the dynamic profiles of the known genotypes by a scale value.

24. The method of claim 21, wherein each dynamic profile is normalized to have a predetermined mean and standard deviation.

25. The method of claim 21, further comprising the step of translating each correlation vector into n-spherical coordinates, wherein n is less than or equal to the number of known genotypes in the class of known genotypes.

26. The method of claim 21, wherein each dynamic profile comprises measurements of a signal representing a physical change of each nucleic acid containing each known genotype relative to an independent variable measured over a range selected to maximize the separation between dynamic profiles for different known genotypes within the class of known genotypes, while minimizing the separation between dynamic profiles of the same known genotype.

27. A method of determining the identity of the genotype of a nucleic acid present in a biological sample, said method comprising the steps of:
(a) providing a microfluidic device comprising one or more microfluidic channels and a controller that interfaces with the microfluidic device;
(b) introducing a biological sample into the microfluidic device;
(c) causing the biological sample to move through the microfluidic channel;
(d) performing an amplification reaction on the biological sample;
(e) causing a physical change of a nucleic acid from the biological sample;
(f) measuring a signal representing said physical change;
(g) causing the controller to perform the following steps:
(i) generate a dynamic profile of an unknown genotype contained in a biological sample, wherein the dynamic profile comprises measurements of a signal representing a physical change of a nucleic acid containing the unknown genotype relative to an independent variable;

(ii) correlate the dynamic profile of the unknown genotype with an average dynamic profile of each known genotype in a class of known genotypes to generate a correlation vector, wherein the average dynamic profile of each known genotype is provided in a training set and comprises average measurements of a signal representing the physical change of a nucleic acid containing the known genotype relative to the independent variable and wherein the correlation vector comprises correlation coefficients between the dynamic profile of the unknown genotype and the average dynamic profile for each known genotype in the class of known genotypes;

(iii) calculate a likelihood of the unknown genotype being a known genotype for each of the known genotypes in the class of known genotypes using class conditional densities of each known genotype, wherein the class conditional densities are calculated using mean transformed vectors and covariance matrices for each genotype and wherein the mean transformed vectors and covariance matrices are obtained from a matrix comprising grouped transformed vectors for each genotype obtained from the training set;

(iv) calculate the posterior probability that the biological sample contains each known genotype from the calculated likelihoods; and (v) determine whether the posterior probability that the biological sample contains a genotype falls within an acceptable threshold to determine if the unknown genotype is classified as one of the known genotypes, whereby the identity of the genotype of the nucleic acid in the biological sample is determined.

28. The method of claim 27, wherein the posterior probability is calculated using Bayes' theorem.

29. The method of claim 27, further comprising the steps of:

(vi) generating a positive control dynamic profile of a control genotype, wherein the positive control dynamic profile comprises measurements of a signal representing a physical change of a nucleic acid containing the control genotype relative to an independent variable taken concurrently with the measurements that comprise the dynamic profile of the unknown genotype;

(vii) comparing the positive control dynamic profile to a standard positive control dynamic profile for the control genotype to determine a shift value for the independent variable; and (viii) shifting the independent variable of the dynamic profile of the positive control and the dynamic profile of the unknown genotype by the shift value.

30. The method of claim 27, wherein each dynamic profile is normalized to have a predetermined mean and standard deviation.

31. The method of claim 27, wherein the training set is prepared by a method comprising:

(a) grouping multiple dynamic profiles of the same genotype for each known genotype in a class of known genotypes, wherein each dynamic profile comprises measurements of a signal representing a physical change of a nucleic acid containing the known genotype relative to an independent variable;

(b) normalizing each of the dynamic profiles;

(c) averaging the normalized dynamic profiles of the same genotype to obtain an average normalized dynamic profile for each known genotype in the class of known genotypes;

(d) correlating each dynamic profile with the average normalized dynamic profile of each known genotype in the class of known genotypes to generate a correlation vector for each dynamic profile, wherein each correlation vector comprises correlation coefficients for the dynamic profile against each average normalized dynamic profile of each known genotype in the class of known genotypes;

(e) transforming the correlation vectors such that when grouped together by genotype, each of the elements of the transformed vector are normally distributed;

(f) compiling each transformed vector into a matrix of transformed vectors, such that there is one matrix for each known genotype in the class of known genotypes;

(g) generating a mean transformed vector whose elements include an average transformed vector for each known genotype where the transformed vector is the average of each compiled matrix; and (h) calculating a covariance matrix for the known genotypes by calculating the covariance matrix of each of the compiled matrices, wherein the training set comprises the average normalized dynamic profile for each known genotype, a mean transformed vector for each known genotype and a covariance matrix for each known genotype.

32. The method of claim 31, wherein each dynamic profile is normalized to have a predetermined mean and standard deviation.

33. The method of claim 31, wherein the method of preparing the training set further comprises the steps of:

(i) generating a positive control dynamic profile of a control genotype, wherein the positive control dynamic profile comprises measurements of a signal representing a physical change of a nucleic acid containing the control genotype relative to an independent variable taken concurrently with the measurements that comprise the dynamic profile of the unknown genotype;

(ii) comparing the positive control dynamic profile to a standard positive control dynamic profile for the control genotype to determine a shift value for the independent variable; and (iii) shifting the independent variable of the dynamic profile of the positive control and the dynamic profile of the unknown genotype by the shift value.

34. The method of claim 33, further comprising the step of scaling the independent variable of the dynamic profile of the positive control and the dynamic profile of the unknown genotype by a scale value.

35. The method of claim 33, wherein the posterior probabilities that fall within the acceptable threshold are greater than 95%.

36. The method of claim 33, further comprising the step of determining whether the correlation vector falls within an acceptable range to determine if one of the known genotypes is identical to the unknown genotype present in the biological sample.

37. The method of claim 36, wherein the acceptable range is an ellipsoid defined by the eigenvectors of the covariance matrix of the training set that contains a predefined threshold percentage of the measurements of the signal relative to the independent variable within the dynamic profile.

38. The method of claim 27, wherein the elements of the correlation vector are transformed to a vector with the same number of elements where each element is normally distributed.

39. The method of claim 27, further comprising the step of translating each correlation vector into n-spherical coordinates, wherein n is one fewer than the number of genotypes in the class of known genotypes.

40. The method of claim 27, further comprising the step of translating each correlation vector into a vector of spherical coordinates, with the same number of elements as the correlation vector.

41. The method of claim 31, further comprising the steps of:
(a) calculating a within-class scatter matrix for the class of known genotypes using the mean transformed vector and the parameter matrix for each genotype;
(b) calculating a between-class scatter matrix for the class of known genotypes using the mean transformed vector and the parameter matrix for each genotype;
(c) determining a separation ratio that is the ratio of the determinant of the within-class scatter matrix to the determinant of the between-class scatter matrix; and
(d) determining a separation-maximizing range for the independent variable, wherein the separation-maximizing range is selected to maximize the separation ratio;
wherein each dynamic profile comprises measurements of a signal representing a physical change of each nucleic acid containing each known genotype relative to an independent variable measured over the separation-maximizing range.

42. A system for determining the identity of the genotype of a nucleic acid present in a biological sample, said system comprising:
(a) a generation module capable of generating a dynamic profile of an unknown genotype contained in a biological sample, wherein the dynamic profile comprises measurements of a signal representing a physical change of a nucleic acid containing the unknown genotype relative to an independent variable;
(b) a correlation module capable of correlating the dynamic profile of the unknown genotype with an average dynamic profile for each known genotype in a class of known genotypes to generate a correlation vector, wherein the average dynamic profile of each known genotype is provided in a training set and comprises average measurements of a signal representing the physical change of a nucleic acid containing the known genotype relative to the independent variable and wherein the correlation vector comprises correlation coefficients between the dynamic profile of the unknown genotype and the average dynamic profile for each known genotype in the class of known genotypes;
(c) a class-conditional density module capable of calculating the likelihood of the unknown genotype being a known genotype for each of the known genotypes in the class of known genotypes using the class conditional densities of each of the known genotypes, wherein the class conditional densities are calculated using mean transformed vectors and covariance matrices for each known genotype and wherein the mean transformed vectors and covariance matrices are obtained from a matrix comprising grouped transformed vectors for each known genotype obtained from the training set;
(d) a posterior probability module capable of calculating the posterior probability that the biological sample contains each known genotype from the calculated likelihoods; and
(e) a determination module capable of determining whether the known genotype with the largest posterior probability falls within an acceptable threshold to determine if the unknown genotype is classified as the genotype with the largest posterior probability, whereby the identity of the genotype in the biological sample is determined.

43. The system of claim 42, wherein the posterior probability module uses Bayes' theorem to calculate the posterior probability.

44. The system of claim 42, further comprising an error correction module capable of comparing a positive control dynamic profile to a known dynamic profile for a control genotype to determine a shift value for the independent variable and shifting the independent variable in the dynamic profile for the unknown genotype by the shift value.

45. The system of claim 42, further comprising a training set module comprising an average dynamic profile for each known genotype in the class of known genotypes, and a parameter matrix, wherein the elements of the parameter matrix are correlation vectors, wherein each correlation vector includes a correlation coefficient between a dynamic profile and each average dynamic profile for each known genotype in the class of known genotypes.

46. The system of claim 45, wherein the average dynamic profile is an average normalized dynamic profile.

47. The system of claim 45, wherein the training set module further comprises a mean transformed vector and a covariance matrix, wherein the elements of the mean transformed vector comprise average values of the correlation coefficients of each dynamic profile of each known genotype against the average dynamic profiles for each known genotype in the class of known genotypes, and wherein the covariance matrix for the known genotypes is obtained by calculating the covariance matrix of the parameter matrix.

48. The system of claim 47, wherein the average dynamic profile is an average normalized dynamic profile.

49. The system of claim 42, wherein the correlation module is further cable of transforming each correlation vector to a transformed vector in which each element of the transformed vector is normally distributed.

50. The system of claim 49, wherein the determination module is further capable of determining whether the transformed vector falls within an acceptable threshold within those obtained from the training set for the genotype with the largest posterior probability.

51. The system of claim 50, wherein the acceptable range is an ellipsoid defined by the eigenvectors of the covariance matrix of the training set that contains a predefined threshold percentage of the measurements of the signal relative to the independent variable within a dynamic profile.

52. The system of claim 42, further comprising a translation module capable of translating a correlation vector into n-spherical coordinates, wherein n is one fewer than the number of genotypes in the class of known genotypes.

53. The system of claim 47, further comprising a separation-maximizing range selection module capable of:
(a) calculating a within-class scatter matrix for the class of known genotypes using the mean transformed vector and the parameter matrix for each genotype;
(b) calculating a between-class scatter matrix for the class of known genotypes using the mean transformed vector and the parameter matrix for each genotype;
(c) determining a separation ratio that is the ratio of the determinant of the within-class scatter matrix to the determinant of the between-class scatter matrix; and
(d) determining a separation-maximizing range for the independent variable, wherein the separation-maximizing range is selected to maximize the separation ratio.

* * * * *